United States Patent
Rioux et al.

(10) Patent No.: US 11,284,622 B2
(45) Date of Patent: Mar. 29, 2022

(54) METHYLOBACTERIUM COMPOSITIONS FOR FUNGAL DISEASE CONTROL

(71) Applicant: NEWLEAF SYMBIOTICS, INC., St. Louis, MO (US)

(72) Inventors: Renée A. Rioux, Morrisville, NC (US); Charles Michael McFatrich, Washington, MO (US); Kishore Nannapaneni, St. Louis, MO (US)

(73) Assignee: NewLeaf Symbiotics, Inc., St. Louis, MO (US)

( * ) Notice: Subject to any disclaimer, the term of this patent is extended or adjusted under 35 U.S.C. 154(b) by 0 days.

(21) Appl. No.: 16/467,384

(22) PCT Filed: Dec. 7, 2017

(86) PCT No.: PCT/US2017/065081
§ 371 (c)(1),
(2) Date: Jun. 6, 2019

(87) PCT Pub. No.: WO2018/106899
PCT Pub. Date: Jun. 14, 2018

(65) Prior Publication Data
US 2019/0364905 A1 Dec. 5, 2019

Related U.S. Application Data

(60) Provisional application No. 62/431,927, filed on Dec. 9, 2016.

(51) Int. Cl.
| | | |
|---|---|---|
| *A01N 63/20* | (2020.01) | |
| *A01N 25/04* | (2006.01) | |
| *A01N 33/24* | (2006.01) | |
| *A01N 37/18* | (2006.01) | |
| *A01N 43/54* | (2006.01) | |
| *A01N 43/56* | (2006.01) | |
| *A01N 43/78* | (2006.01) | |
| *A01N 43/80* | (2006.01) | |
| *A01N 43/88* | (2006.01) | |

(52) U.S. Cl.
CPC ............ *A01N 63/20* (2020.01); *A01N 25/04* (2013.01); *A01N 33/24* (2013.01); *A01N 37/18* (2013.01); *A01N 43/54* (2013.01); *A01N 43/56* (2013.01); *A01N 43/78* (2013.01); *A01N 43/80* (2013.01); *A01N 43/88* (2013.01)

(58) Field of Classification Search
CPC ........ A01N 25/04; A01N 63/00; A01N 63/20; A01N 33/24; A01N 37/18; A01N 43/54; A01N 43/56; A01N 43/78; A01N 43/80; A01N 43/88
USPC ....................................................... 424/9.31
See application file for complete search history.

(56) References Cited

U.S. PATENT DOCUMENTS

| | | |
|---|---|---|
| 6,014,451 A | 1/2000 | Berry et al. |
| 6,133,196 A | 10/2000 | Ocamb et al. |
| 9,181,541 B2 | 11/2015 | Bogosian |
| 9,845,462 B2 | 12/2017 | Bogosian |
| 10,098,353 B2 | 10/2018 | Breakfield et al. |
| 10,111,438 B2 | 10/2018 | Floro et al. |
| 10,212,939 B2 | 2/2019 | Floro et al. |
| 10,287,544 B2 | 5/2019 | Bogosian |
| 10,368,547 B2 | 8/2019 | Floro et al. |
| 10,448,645 B2 | 10/2019 | Breakfield et al. |
| 10,450,556 B2 | 10/2019 | Bogosian |
| 10,716,307 B2 | 7/2020 | Breakfield et al. |
| 10,757,946 B2 | 9/2020 | Allen et al. |
| 2008/0148432 A1 | 6/2008 | Abad |
| 2011/0053771 A1 | 3/2011 | Goodwin |
| 2014/0147425 A1 | 5/2014 | Henn et al. |
| 2015/0337256 A1 | 11/2015 | Bogosian |
| 2016/0073641 A1 | 3/2016 | Allen et al. |
| 2016/0120188 A1 | 5/2016 | Bogosian |
| 2016/0295868 A1 | 10/2016 | Jones et al. |
| 2016/0302423 A1 | 10/2016 | Jones et al. |
| 2016/0302424 A1 | 10/2016 | DiDonato et al. |
| 2016/0302425 A1 | 10/2016 | DiDonato et al. |
| 2017/0086464 A1 | 3/2017 | Floro et al. |
| 2017/0135352 A1 | 5/2017 | Breakfield et al. |
| 2017/0164618 A1 | 6/2017 | Breakfield et al. |
| 2017/0238553 A1 | 8/2017 | Jones et al. |
| 2018/0142230 A1 | 5/2018 | Bogosian |
| 2018/0295841 A1 | 10/2018 | Rioux |
| 2019/0021334 A1 | 1/2019 | DiDonato Floro et al. |
| 2019/0116803 A1 | 4/2019 | DiDonato Floro et al. |
| 2019/0241865 A1 | 8/2019 | Bogosian |
| 2019/0297895 A1 | 10/2019 | Floro et al. |
| 2019/0364905 A1 | 12/2019 | Rioux et al. |

FOREIGN PATENT DOCUMENTS

| | | | |
|---|---|---|---|
| BE | WO 2011/154159 | * | 12/2011 |
| CA | 2183275 A1 | | 2/1998 |
| CN | 101028008 A | | 9/2007 |

(Continued)

OTHER PUBLICATIONS

International Search Report and Written Opinion for PCT/US2016/36968 dated Dec. 7, 2016.

(Continued)

*Primary Examiner* — Jennifer M. H. Tichy
(74) *Attorney, Agent, or Firm* — Stinson LLP

(57) ABSTRACT

Compositions comprising *Methylobacterium* with anti-fungal activity, methods for controlling plant pathogenic fungi, and methods of making the compositions are provided.

20 Claims, 4 Drawing Sheets

Specification includes a Sequence Listing.

(56) References Cited

FOREIGN PATENT DOCUMENTS

| CN | 104508118 A | 4/2015 |
|---|---|---|
| WO | 2013181610 A1 | 12/2013 |
| WO | 2015/085063 A1 | 6/2015 |
| WO | 2015085117 A1 | 6/2015 |
| WO | 2015/142393 A1 | 9/2015 |
| WO | 2015/200902 A2 | 12/2015 |
| WO | 2016/069564 A1 | 5/2016 |
| WO | 2016/201284 A2 | 12/2016 |
| WO | 2018106899 A1 | 6/2018 |
| WO | 2020117689 A1 | 6/2020 |
| WO | 2020117690 A1 | 6/2020 |

OTHER PUBLICATIONS

International Search Report and Written Opinion for PCT/US2017/065081 dated Mar. 12, 2018.

Madhaiyan et al., "Growth Promotion and Induction of Systemic Resistance in Rice Cultivar Co-47 (*Oryza sativa* L.) by *Methylobacterium* spp.", Bot. Bull. Acad. Sin., 2004, pp. 315-324, vol. 45.

Madhaiyan et al., "Pink Pigmented Facultative Methylotrophic Bacteria (PPFMs): Introduction to Current Concepts", Korean J. Soil Sci. Fert., 2004, pp. 266-287, vol. 37, No. 4.

Madhaiyan et al., "Plant Growth-Promoting Methylobacterium Induces Defense Responses in Groundnut (*Arachis hypogaea* L.) Compared with Rot Pathogens", Current Microbiology, 2006, pp. 270-276, vol. 53.

Menpara et al., "Endophytic Bacteria-Unexplored Reservoir of Antimicrobials for Combating Microbial Pathogens", Microbial Pathogens and Strategies for Combating them: Science, Technology and Education, Dec. 1, 2013, pp. 1095-1103, vol. 2.

Nascimento et al., "Endophytic Bacteria from Piper Tuberculatum Jacq.: Isolation, Molecular Characterization, and in Vitro Screening for the Control of *Fusarium Solani* f. sp. piperis, the Casual Agent of Root Rot Disease in Black Pepper (*Piper nigrum* L.)", Genetics and Molecular Research, Jan. 1, 2015, pp. 7567-7577, vol. 14, No. 3.

Poorniammal et al., "In Vitro Biocontrol Activity of Methylobacterium Extorquens Against Fungal Pathogens", International Journal of Plant Protection, 2009, pp. 59-62, vol. 2, No. 1.

Savitha, "Studies on Pink Pigmented Facultative Methylotrophs of Major Chilli Growing Areas of North Karnataka", Jun. 1, 2015, pp. 1-139, retrieved from: http://krishikosh.egranth.ac.in/bitstream/69836/1/th10680.pdf.

Schlaeppi et al., "The Plant Microbiome at Work", MPMI vol. 28, No. 3, 2015, pp. 217-217; http://dx.doi.org/10.1094/MPMI-10-14-0334-FI.

Tani et al., "High-Throughput Identification and Screening of Novel *Methylobacterium* Species Using Whole-Cell MALDI-TOF/MS Analysis", PLoS ONE, Jul. 12, 2012, pp. 1-13, vol. 7, No. 7.

Ardanov et al., "Effects of *Methylobacterium* sp. on emergence, yield, and disease prevalence in three cultivars of potato (*Solanum tuberosum* L.) were associated with the Shift in Endophytic Microbial Community", Plant and Soil, Way 2015, pp. 299-310, vol. 405, No. 1, Kluwer Academic Publishers.

Extended European Search Report for EP17877804.9 dated Jun. 26, 2020.

\* cited by examiner

METHYLOBACTERIUM COMPOSITIONS FOR FUNGAL DISEASE CONTROL

CROSS-REFERENCE TO RELATED APPLICATIONS

This is a U.S. National Phase application of PCT Application Serial No. PCT/US2017/065081, filed on Dec. 7, 2017, which claims the benefit of U.S. Provisional Application Ser. No. 62/431,927, filed Dec. 9, 2016, each of which are incorporated herein by reference in their entireties.

SEQUENCE LISTING STATEMENT

A sequence listing containing the file named "53907-171478_ST25.txt" which is 32768 bytes (measured in MS-Windows®) and created on Dec. 1, 2017, contains 60 nucleotide sequences, is provided herewith via the USPTO's EFS system, and is incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase that incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

Biotic pressures—the combined effects of pathogens, animals, insects, and weeds—result in an annual loss of 20-40% crop productivity. Additional costs of pest control, reduced crop quality, and funding research to combat these pressures, among other factors, make it difficult to precisely quantify losses due to crop pests and diseases (Savary et al. 2012, Food Sec. DOI: 10.1007/s12571-012-0200-5). Agricultural biologicals present a novel, exciting, and rapidly emerging option to combat crop pests and diseases in a manner that complements and preserves current crop germplasm resistance traits, chemical control options, and cultural practices (Schlaeppi and Bulgarelli 2015, MPMI 28(3): 212-217. DOI: 10.1094/MPMI-10-14-0334-FI).

Fungal diseases are a major cause of yield and quality loss to agronomically important row crops, including corn, soybeans, wheat, cotton, and canola. Among these diseases, species of ascomycete fungi in the genera *Cercospora, Colletotrichum, Fusarium*, and *Septoria* are particularly widespread and contribute to significant crop losses. *Fusarium* species alone caused an estimated 36.2 million bushels/year loss in soybeans from the years 1994-2010 (Wrather et al. 2010). These species cause a range of foliar, seedling, and stalk maladies, and, unlike rusts or other diseases caused by obligate biotrophic pathogens, there is no complete genetic resistance to these diseases. Further, chemical controls often must be applied at very precise times to successfully stymie disease progress while maximizing profits and protecting plant health. The narrow thresholds and windows for control can result in incomplete or failed crop protection. Microbial inoculants, which can colonize from the seed and persist on plants and in soil for the full duration of the growing season, offer extended windows of protection, can compensate for chemical control insufficiencies, and extend the benefits of fungicide through resistance management.

SUMMARY

Provided herein are compositions comprising *Methylobacterium* that inhibit growth of a plant pathogenic fungus, methods of using the compositions to control fungal infections of plants, plant parts, and plants derived therefrom, and methods of making the compositions. Such *Methylobacterium* that inhibit growth of a plant pathogenic fungus are in certain instances referred to herein as "*Methylobacterium* that inhibit plant pathogenic fungi" or, in certain contexts, as simply "*Methylobacterium*". In certain embodiments, *Methylobacterium* that inhibit growth of a plant pathogenic fungus can be distinguished from other *Methylobacterium* that do not inhibit plant pathogenic fungi by assaying for the ability of the *Methylobacterium* to inhibit fungal disease in a plant or on an isolated plant part.

Provided herein are compositions comprising a mono- or co-culture of *Methylobacterium* that inhibit growth of a plant pathogenic fungus and an agriculturally acceptable excipient and/or an agriculturally acceptable adjuvant. In certain embodiments, the *Methylobacterium* has at least one gene that encodes a 16S RNA having at least 97%, 98%, 99%, 99.5%, or 100% sequence identity to SEQ ID NO: 8; or the *Methylobacterium* is NLS0109 or a derivative thereof. In certain embodiments, the *Methylobacterium* has in its genome one or more polynucleotide marker fragments of at least 50, 60, 100, 120, 180, 200, 240, or 300 nucleotides of SEQ ID NOS: 9-11. In certain embodiments, the *Methylobacterium* has in its genome one or more marker fragments comprising a sequence having at least 98%, 99%, or 99.5% sequence identity across the entire length of SEQ ID NOS: 9-11. In certain embodiments, the *Methylobacterium* is not *M. radiotolerans* or *M. oryzae*. In certain embodiments, the plant pathogenic fungus is selected from the group consisting of a *Blumeria* sp., a *Cercospora* sp., a *Cochliobolus* sp., a *Colletotrichum* sp., a *Diplodia* sp., an *Exserohilum* sp., a *Fusarium* sp., a *Gaeumanomyces* sp., a *Macrophomina* sp., a *Magnaporthe* sp., a *Microdochium* sp., a *Peronospora* sp., a *Phakopsora* sp., a *Phialophora* sp., a *Phoma* sp., a *Phymatotrichum* sp., a *Phytophthora* sp., a *Pyrenophora* sp., a *Pyricularia* sp, a *Pythium* sp., a *Rhizoctonia* sp., a *Sclerophthora*, a *Sclerospora* sp., a *Sclerotium* sp., a *Sclerotinia* sp., a *Septoria* sp., a *Stagonospora* sp., a *Stenocarpella* sp. and a *Verticillium* sp. In certain embodiments, the *Fusarium* sp. is selected from the group consisting of *Fusarium graminearum, Fusarium verticillioides, Fusarium oxysporum, Fusarium virguliforme*, and *Fusarium solani*. In certain embodiments of any of the aforementioned compositions, the composition comprises a solid substance wherein a mono-culture or co-culture of *Methylobacterium* is adhered thereto. In certain embodiments, the plant pathogenic fungus is a *Rhizoctonia* sp. or a *Sclerotinia* sp. In certain embodiments, the *Rhizoctonia* sp. is *Rhizoctonia solani* or *Rhizoctonia cerealis*. In certain embodiments, the *Sclerotinia* sp. is *Sclerotinia sclerotiorum* or *Sclerotinia homoeocarpa*. In certain embodiments, the composition comprises a colloid formed by the solid substance wherein a mono-culture or co-culture of *Methylobacterium* is adhered thereto and a liquid. In certain embodiments, the colloid is a gel. In certain embodiments of any of the aforementioned compositions, the composition is an emulsion. In certain embodiments of any of the aforementioned compositions, the *Methylobacterium* is NLS0109, a derivative thereof, or a *Methylobacterium* related to NLS0109. In certain embodiments of any of the aforementioned compositions, the composition further comprises a second *Methylobacterium* strain selected from NLS0017, NLS0020, NLS0021, NLS0042, NLS0064, NLS0066, NLS0089, a derivative thereof, or a *Methylobacterium* sp. related thereto. In certain embodiments, derivatives of *Methylobacterium* strains NLS0017, NLS0020, NLS0089 and NL0109 or a *Methylobacterium* sp. related thereto can be identified in by the presence of one or more marker fragments selected from the group consisting of SEQ ID NO: 9-11, 21-24, 37-39, or 49-51, and can be distinguished from other related *Methylobacterium* by PCR analysis using specific DNA detection assays that include, but are not limited to, DNA primer and probe combinations provided herein. Use of any of the aforementioned compositions for coating or partially coating a plant part (e.g., a seed) to inhibit growth of any of the aforementioned plant pathogenic fungi is also provided herein.

In certain embodiments of any of the aforementioned compositions, the *Methylobacterium* is NLS0109 or a derivative thereof. In certain embodiments, the *Methylobacterium* is NLS0109, a derivative thereof, or a *Methylobacterium* related to NLS0109 and the plant pathogenic fungus is a *Rhizoctonia* sp. or a *Sclerotinia* sp. In certain embodiments, the *Methylobacterium* is NLS0109, a derivative thereof, or a *Methylobacterium* related to NLS0109 and the plant pathogenic fungus is *Fusarium graminearum, Cercospora zeae-maydis*, or *Colletotrichum graminicola*. In certain embodiments, the *Methylobacterium* is NLS0109, a derivative thereof, or a *Methylobacterium* related to NLS0109 and the plant pathogenic fungus is *Septoria tritici, Stagonospora nodorum, Pythium* spp., *Rhizoctonia solani*, a *Fusarium* spp., *Magnaportha grisea, Pyrenophora tritici-repentis, Microdochium nivale, Sclerotinia sclerotiorum, Cercospora sojina, Cercospora kikuchii, Fusarium* spp., *Rhizoctonia solani, Fusarium virguliforme, Pythium* spp., *Rhizoctonia solani, Gibberella zeae*, or a *Pythium* spp. In any of the aforementioned embodiments, the plant pathogenic fungus that is inhibited can be in its anamorphic form, its teleomorphic form, or in both its anamorphic form and its teleomorphic forms. In any of the aforementioned embodiments, the composition can comprise a fungal inhibitory concentration of the mono- or co-culture of *Methylobacterium*. Use of any of the aforementioned compositions for coating or partially coating a plant part (e.g., a seed) to inhibit growth of any of the aforementioned plant pathogenic fungi is also provided herein.

In certain embodiments, the *Methylobacterium* is NLS0109, a derivative thereof, or a *Methylobacterium* related to NLS0109 and the plant pathogenic fungus is a *Rhizoctonia* sp. or a *Fusarium* sp. and the plant is corn or soybean. In certain embodiments of the methods, the *Fusarium* sp. is one or more species selected from *Fusarium graminearum, Fusarium verticillioides, Fusarium oxysporum, Fusarium virguliforme*, and *Fusarium solani*, and the *Rhizoctonia* is *Rhizoctonia solani*. In some embodiments, *Methylobacterium* sp. control of fungal infections by *Fusarium* and *Rhizoctonia* is evidenced by improved germination and emergence of seed following application of the *Methylobacterium*. In certain embodiments, the *Methylobacterium* is NLS0109, a derivative thereof, or a *Methylobacterium* related to NLS0109 and the plant pathogenic fungus is a *Pythium* sp. and the plant is corn or soybean. In certain embodiments of the methods, the *Pythium* sp. is one or more species selected from *Pythium torulosum, Pythium oopapillum, Pythium sylvaticum* and *Pythium lutarium*.

In any of the aforementioned embodiments, the composition can further comprise an antifungal compound. In certain embodiments, the antifungal compound can be an azole, a dithiocarbamate, a strobilurin, a phenylamide, a thiazole-carboxamide, a piperidinyl thiazole isoxazoline or a benzimidazole. In certain embodiments, the azole is ipconazole, tebuconazole, triticonazole, metconazole, prothioconazole, triadimenfon, propiconazole and imazalil. In certain embodiments, the composition further comprises a strobilurin fungicide. In certain embodiments, the strobilurin fungicide is selected from the group consisting of azoxystrobin, pyraclostrobin, fluoxastrobin, and trifloxystrobin. In certain embodiments, the strobilurin fungicide is pyraclostrobin. Use of any of the aforementioned compositions for coating or partially coating a plant part (e.g., a seed) to inhibit growth of any of the aforementioned plant pathogenic fungi is also provided herein. In certain embodiments of any of the aforementioned compositions or uses, the combination of *Methylobacterium*, crop, pathogen, disease, and/or antifungal compounds is as set forth in Table 4.

Also provided are plants or plant parts that are at least partially coated with any of the aforementioned compositions comprising a mono- or co-culture of *Methylobacterium*. In certain embodiments, the *Methylobacterium* has at least one gene that encodes a 16S RNA having at least 97%, 98%, 99%, 99.5%, or 100% sequence identity to SEQ ID NO: 8; or the *Methylobacterium* is NLS0109 or a derivative thereof. In certain embodiments, the *Methylobacterium* has in its genome one or more polynucleotide marker fragments of at least 50, 60, 100, 120, 180, 200, 240, or 300 nucleotides of SEQ ID NOS: 9-11. In certain embodiments, the *Methylobacterium* has in its genome one or more marker fragments comprising a sequence having at least 98%, 99%, or 99.5% sequence identity across the entire length of SEQ ID NOS: 9-11. In certain embodiments, the at least partially coated plant or plant part is a cereal plant or cereal plant part. In certain embodiments, the at least partially coated cereal plant is selected from the group consisting of a rice, wheat, corn, barley, millet, sorghum, oat, and rye plant. In certain embodiments, the at least partially coated cereal plant part is selected from the group consisting of a rice, wheat, corn, barley, millet, sorghum, oat, and rye plant part. In certain embodiments, the at least partially coated plant or plant part is a dicot plant part. In certain embodiments, the dicot plant or plant part is a soybean, peanut, or tomato plant part. In certain embodiments of any of the aforementioned plants or plant parts, the *Methylobacterium* in the composition was obtained from a plant genus, plant species, plant sub-species, or plant cultivar that is distinct from the genus, species, sub-species, or cultivar of the plant or plant part that is coated with the composition. Also provided are processed plant products that comprise a detectable amount of any of the *Methylobacterium* of any of the aforementioned compositions.

Also provided herein are methods of identifying compositions including, but not limited to, soil samples, plant parts, including plant seeds, or processed plant products, comprising or coated with *Methylobacterium* sp. NLS0109, NL0020, NLS0017 or NLS0089 by assaying for the presence of nucleic acid fragments comprising at least 40, 50, 60, 100, 120, 180, 200, 240, or 300 nucleotides of SEQ ID NO: 9-11, 21-24, 37-39, or 49-51 in the compositions. In certain embodiments, such methods can comprise subjecting a sample suspected of containing *Methylobacterium* sp. NLS0109, NL0020, NLS0017 or NLS0089 to a nucleic acid analysis technique and determining that the sample contains one or more nucleic acid containing a sequence of at least about 50, 100, 200, or 300 nucleotides that is identical to a contiguous sequence in SEQ ID NO: 9-11, 21-24, 37-39, or 49-51, wherein the presence of a sequence that is identical to a contiguous sequence in SEQ ID NO: 9-11, 21-24, 37-39, or 49-51 is indicative of the presence of NLS0109 (SEQ ID NO: 9-11), NL0020 (SEQ ID NO: 21-24) NLS0017 (SEQ ID NO: 37-39) or NLS0089 (SEQ ID NO: 49-51) in the sample. Such nucleic acid analyses include, but are not limited to, techniques based on nucleic acid hybridization, polymerase chain reactions, mass spectroscopy, nanopore based detection, branched DNA analyses, combinations thereof, and the like. One example of such a nucleic acid analysis is a qPCR Locked Nucleic Acid (LNA) based assay described herein. Such analysis can be used to detect *Methylobacterium* strains present at a concentration (CFU/gm of sample) of $10^3$, $10^4$, $10^5$, $10^6$ or more.

Also provided herein are methods of identifying and/or isolating *Methylobacterium* sp. that can inhibit growth of a plant pathogenic fungus by assaying for the presence of nucleic acid sequences contained in SEQ ID NO: SEQ ID NO: 9-11, 21-24, 37-39, or 49-51 in the *Methylobacterium* sp. In certain embodiments, such methods can comprise subjecting a candidate *Methylobacterium* sp. to a nucleic acid analysis technique and determining that the sample contains one or more nucleic acid containing a sequence of at least about 50, 100, 200, or 300 nucleotides that is identical to a contiguous sequence in SEQ ID NO: 9-11, 21-24, 37-39, or 49-51, wherein the presence of a sequence that is identical to a contiguous sequence in SEQ ID NO: 9-11, 21-24, 37-39, or 49-51 indicates that the candidate *Methylobacterium* sp. that can inhibit growth of a plant pathogenic fungus. Such nucleic acid analyses include, but are not limited to, techniques based on nucleic acid hybridization, polymerase chain reactions, mass spectroscopy, nanopore based detection, branched DNA analyses, combinations thereof, and the like.

In certain embodiments, a *Methylobacterium* that is NLS0109, a derivative thereof, or a *Methylobacterium* related to NLS0109, is used in any of the aforementioned compositions, uses thereof, or methods to inhibit growth of a plant pathogenic fungus, where the use and/or method comprises control of any of the pathogens or diseases, in any of the crops, through any of the modes of application set forth in Table 3. In certain embodiments of any of the aforementioned compositions, uses thereof, or methods, the *Methylobacterium* is NLS0109, a derivative thereof, or a *Methylobacterium* related to NLS0109, the plant pathogenic fungus that is inhibited is *Fusarium graminearum, Septoria tritici, Stagonospora nodorum, Rhizoctonia solani*, a *Fusarium* spp., *Magnaportha grisea, Pyrenophora tritici-repentis, Microdochium nivale, Blumeria graminis* f. sp. *tritici*, or a *Pythium* sp., and the plant or plant part is a wheat plant or plant part. In certain embodiments of any of the aforementioned compositions, uses thereof, or methods, the *Methylobacterium* is NLS0109, a derivative thereof, or a *Methylobacterium* related to NLS0109, the plant pathogenic fungus that is inhibited is *Cercospora zeae-maydis, Colletotrichum graminicola, Fusarium graminearum, Fusarium verticillioides, Gibberella zeae, Rhizoctonia solani, Stenocarpella maydis*, a *Pythium* sp., *Sclerospora graminicola* or *Sclerophthora macrospora*, and the plant or plant part is a corn plant or corn plant part. In certain embodiments of any of the aforementioned compositions, uses thereof, or methods, the *Methylobacterium* is NLS0109, a derivative thereof, or a *Methylobacterium* related to NLS0109, the plant pathogenic fungus that is inhibited is *Sclerotinia sclerotiorum, Cercospora sojina, Cercospora kikuchii, Fusarium* spp., *Rhizoctonia solani, Septoria glycines, Fusarium virguliforme, Pythium* spp., *Peronospora manshurica*, or *Phytophthora sojae*, and the plant or plant part is a soybean plant or soybean plant part.

In certain embodiments of any of the aforementioned compositions, uses thereof, or methods, the *Methylobacterium* is NLS0109, a derivative thereof, or a *Methylobacterium* related thereto and a second *Methylobacterium* selected from NLS0020, NLS0017, NLS0089, a derivative thereof, or a *Methylobacterium* related thereto, is included in the composition. In certain embodiments, the combination of NLS0109 with a second *Methylobacterium* selected from NLS0020, NLS0017, NLS0089, a derivative thereof, or a *Methylobacterium* related thereto that is used in any of the aforementioned compositions, uses thereof, or methods comprises any of the combinations of *Methylobacterium*, crops, pathogens, diseases, and/or modes of application set forth in Table 3. For example, in certain embodiments set forth in Table 3, the *Methylobacterium* is NLS0109, a derivative thereof, or a *Methylobacterium* related thereto and a second *Methylobacterium* is NLS0020, a derivative thereof, or a *Methylobacterium* related thereto, the crop is wheat, the pathogen is *Fusarium graminearum, Septoria tritici; Stagonospora nodorum*, a *Pythium* spp., *Rhizoctonia solani*, a *Fusarium* spp., *Blumeria graminis* f sp. *tritici, Magnaporthe grisea, Pyrenophora tritici-repentis*, or *Microdochium nival*, and application is to a seed in-furrow; foliar; or any combination thereof, where isolates are used alone or in combination for any treatment, including NLS0020 applied in-furrow and NLS0109 applied foliar. In certain embodiments, the *Methylobacterium* is NLS0109, a derivative thereof, or a *Methylobacterium* related thereto and a second *Methylobacterium* selected from NLS0020, NLS0017, NLS0089, a derivative thereof, or a *Methylobacterium* related thereto, the plant pathogenic fungus that is inhibited is *Fusarium graminearum, Septoria tritici, Stagonospora nodorum, Rhizoctonia solani*, a *Fusarium* spp., *Magnaportha grisea, Pyrenophora tritici-repentis, Microdochium nivale, Blumeria graminis* f. sp. *tritici*, or a *Pythium* sp., and the plant or plant part is a wheat plant or plant part. In certain embodiments, the *Methylobacterium* is NLS0109, a derivative thereof, or a *Methylobacterium* related thereto and a second *Methylobacterium* selected from NLS0020, NLS0021, NLS0017, NLS0089, a derivative thereof, or a *Methylobacterium* related thereto, the plant pathogenic fungus that is inhibited is *Cercospora zeae-maydis, Colletotrichum graminicola, Fusarium graminearum, Fusarium verticillioides, Gibberella zeae, Rhizoctonia solani, Stenocarpella maydis,* a *Pythium* sp., *Sclerospora graminicola* or *Sclerophthora macrospora*, and the plant or plant part is a corn plant or corn plant part. In certain embodiments, the *Methylobacterium* is NLS0109, a derivative thereof, or a *Methylobacterium* related thereto and a second *Methylobacterium* selected from NLS0020, NLS0064, NLS0017, NLS0089, a derivative thereof, or a *Methylobacterium* related thereto, the plant pathogenic fungus that is inhibited is *Sclerotinia sclerotiorum, Cercospora sojina, Cercospora kikuchii, Fusarium* spp., *Rhizoctonia solani, Septoria glycines, Fusarium virguliforme, Pythium* spp., *Peronospora manshurica,* or *Phytophthora sojae,* and the plant or plant part is a soybean plant or soybean plant part In certain embodiments of any of the aforementioned compositions, uses thereof, or methods, the plant or plant part comprises a fungal inhibitory amount of the *Methylobacterium*. In certain embodiments, a fungal inhibitory amount of the *Methylobacterium* applied to a plant part (e.g., a seed) is about $1.0 \times 10^3$, $1.0 \times 10^4$, or $1.0 \times 10^5$ to about $1.0 \times 10^7$ or $1.0 \times 10^8$ CFUs of PPFM bacteria/plant part (e.g., a seed). In certain embodiments, the *Methylobacterium* is heterologous to the plant or plant part. In certain embodiments of any of the aforementioned plant parts, the plant part is a leaf, a stem, a flower, a root, a tuber, or a seed.

Also provided are methods of making any of the aforementioned compositions containing the *Methylobacterium* that inhibit growth of a plant pathogenic fungus that comprise combining a *Methylobacterium* that inhibit growth of a plant pathogenic fungus with an agriculturally acceptable excipient and/or with an agriculturally acceptable adjuvant. In certain embodiments, the *Methylobacterium* has: (i) at least one gene that encodes a 16S RNA having at least 97%, 98%, 99%, 99.5%, or 100% sequence identity to SEQ ID NO: 8; (ii) has in its genome one or more polynucleotide marker fragments of at least 50, 60, 100, 120, 180, 200, 240, or 300 nucleotides of SEQ ID NOS: 9-11; or (iii) has in its genome one or more marker fragments comprising a sequence having at least 98%, 99%, or 99.5% sequence identity across the entire length of SEQ ID NOS: 9-11; or the *Methylobacterium* is NLS0109 or a derivative thereof. In certain embodiments of the methods, the *Methylobacterium* sp. is selected from the group consisting of *M. aminovorans, M. extorquens, M. fujisawaense, M. mesophilicum, M. radiotolerans, M. rhodesianum, M. nodulans, M. phyllosphaerae, M. thiocyanatum,* and *M. oryzae*. In certain embodiments of the methods, the *Methylobacterium* is not *M. radiotolerans* or *M. oryzae*. In certain embodiments of the methods, the *Methylobacterium* is NLS0109, a derivative thereof, or a *Methylobacterium* related to NLS0109. In certain embodiments of any of the aforementioned methods, the composition further comprises *Methylobacterium* strain NLS0017, NLS0020, NLS0021, NLS0042, NLS0064, NLS0066, NLS0089, a derivative thereof, or a *Methylobacterium* sp. related thereto. In certain embodiments of any of the aforementioned methods, the *Methylobacterium* is NLS0109, a derivative thereof, or a *Methylobacterium* related to NLS0109. In certain embodiments, the plant or plant part is a soybean plant or soybean plant part. In certain embodiments, the plant or plant part is selected from the group consisting of a rice, wheat, corn, barley, millet, sorghum, oat, and rye plant or plant part. In certain embodiments of the methods, the plant pathogenic fungus is selected from the group consisting of a *Blumeria* sp., a *Cercospora* sp., a *Cochliobolus* sp., a *Colletotrichum* sp., a *Diplodia* sp., an *Exserohilum* sp., a *Fusarium* sp., a *Gaeumanomyces* sp., a *Macrophomina* sp., a *Magnaporthe* sp., a *Microdochium* sp., a *Peronospora* sp., a *Phakopsora* sp., a *Phialophora* sp., a *Phoma* sp., a *Phymatotrichum* sp., a *Phytophthora* sp., a *Pyrenophora* sp., a *Pyricularia* sp, a *Pythium* sp., a *Rhizoctonia* sp., a *Sclerophthora,* a *Sclerospora* sp., a *Sclerotium* sp., a *Sclerotinia* sp., a *Septoria* sp., a *Stagonospora* sp., a *Stenocarpella* sp. and a *Verticillium* sp.

In certain embodiments of any of the aforementioned compositions, uses thereof, or methods, the mono- or co-culture of *Methylobacterium* is adhered to a solid substance. In certain embodiments of the methods, the *Methylobacterium* that is adhered to the solid substance is combined with a liquid to form a composition that is a colloid. In certain embodiments of the methods, the colloid is a gel. In certain embodiments of the methods, the mono- or co-culture of *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion. In any of the aforementioned embodiments, the plant pathogenic fungus that is inhibited can be in its anamorphic form, its teleomorphic form, or in both its anamorphic and teleomorphic forms. In any of the aforementioned embodiments, the composition can further comprise an antifungal compound selected from the group consisting of an azole, dithiocarbamate, strobilurin, and benzimidazole. In certain embodiments, the azole is ipconazole.

Also provided are methods for controlling a plant pathogenic fungus that comprise applying any of the aforementioned compositions as a first composition that contains one or more *Methylobacterium* that inhibit growth of a plant pathogenic fungus to a plant or a plant part, to soil where a plant is grown, to soil where a plant part such as a seed is deposited, or any combination thereof, in an amount that provides for inhibition of infection by the plant pathogenic fungus in the plant, plant part, or a plant obtained therefrom relative to infection of a control plant, plant part, or plant obtained therefrom that had not received an application of the composition or been grown in soil treated with the composition. In certain embodiments, the *Methylobacterium*: (i) has at least one gene that encodes a 16S RNA having at least 97%, 98%, 99%, 99.5%, or 100% sequence identity to SEQ ID NO: 8; (ii) has in its genome one or more polynucleotide marker fragments of at least 50, 60, 100, 120, 180, 200, 240, or 300 nucleotides of SEQ ID NOS: 9-11; or (iii) has in its genome one or more marker fragments comprising a sequence having at least 98%, 99%, or 99.5% sequence identity across the entire length of SEQ ID NOS: 9-11; or the *Methylobacterium* is NLS0109, a derivative thereof, or is a *Methylobacterium* related to NLS0109. In certain embodiments, the *Methylobacterium* contains in its genome one or more marker fragments having a sequence of SEQ ID NOS: 9-11.

In certain embodiments of any of the aforementioned methods or uses, the application of the composition provides for at least 40%, 50%, 75%, at least 85%, or at least 95% inhibition of a plant pathogenic fungal infection in the plant, plant part, or a plant derived therefrom relative to infection of the control plant, plant part, or plant obtained therefrom. In certain embodiments of the methods, the plant part is selected from the group consisting of a leaf, a stem, a flower, a root, a tuber, and a seed. In certain embodiments of the methods, the method further comprises the step of harvesting at least one plant part selected from the group consisting of a leaf, a stem, a flower, a root, a tuber, or a seed from the plant or plant part. In certain embodiments of the methods, the mycotoxin levels in the plant part are reduced by at least 50%, at least 75%, at least 85%, or at least 95% relative to a plant part obtained from the control plant, plant part, or plant obtained therefrom. In certain embodiments of the aforementioned methods, the method further comprises obtaining a processed food or feed composition from the plant or plant part. In certain embodiments of the aforementioned methods, the mycotoxin levels in the processed food or feed composition are reduced by at least 50%, at least 75%, at least 85%, or at least 95% relative to a processed food or feed composition obtained from the control plant, plant part, or plant obtained therefrom. In certain embodiments, a fungal inhibitory amount of the *Methylobacterium* is applied to the plant part. In certain embodiments, the fungal inhibitory amount of the *Methylobacterium* applied to a plant part (e.g., a seed) is about $1.0 \times 10^3$, $1.0 \times 10^4$, or $1.0 \times 10^5$ to about $1.0 \times 10^7$, $1.0 \times 10^8$, $1.0 \times 10^9$, or $1.0 \times 10^{10}$ CFUs of *Methylobacterium*/plant part (e.g., a seed). In certain embodiments, the *Methylobacterium* is heterologous to the plant or plant part. In certain embodiments of any of the aforementioned methods, the plant part is a leaf, a stem, a flower, a root, a tuber, or a seed. In certain embodiments of the methods, the *Methylobacterium* is NLS0109, a derivative thereof, or a *Methylobacterium* related to NLS0109. In certain embodiments of any of the aforementioned methods, the composition further comprises *Methylobacterium* strain NLS0017, NLS0020, NLS0021, NLS0042, NLS0064, NLS0066, NLS0089, a derivative thereof, or a *Methylobacterium* sp. related thereto. In certain embodiments, a derivative of NLS0020, NLS0017, or NLS0089, or a *Methylobacterium* sp. related to NLS0020, NLS0017, or NLS0089, can be identified by the presence of one or more marker fragments having a sequence of SEQ ID NO:21-24, 37-39, or 49-51. In certain embodiments of any of the aforementioned methods, the *Methylobacterium* is NLS0109 or a derivative thereof. In certain embodiments, the plant or plant part is a soybean plant or soybean plant part, or a peanut plant or peanut plant part. In certain embodiments, the plant or plant part is selected from the group consisting of a rice, wheat, corn, barley, millet, sorghum, oat, and rye plant or plant part.

In certain embodiments, the methods can further comprise applying a second composition to soil where the plant is grown, wherein the second composition comprises *Methylobacterium* strain NLS0017, NLS0020, NLS0021, NLS0042, NLS0064, NLS0066, NLS0089, a derivative thereof, or a *Methylobacterium* sp. related thereto. In certain embodiments, the second composition is applied to the soil in furrow with the plant part or with a seed from which the plant is grown. In certain embodiments, the first composition is applied to foliage of the plant after application of the second composition to the soil. In certain embodiments, the first composition comprises NLS0109, a derivative thereof, or a *Methylobacterium* sp. related thereto; and the second composition comprises *Methylobacterium* strain NLS0020, NLS0021, NLS0017, a derivative thereof, or a *Methylobacterium* sp. related thereto. In certain embodiments, the first composition comprises NLS0109, a derivative thereof, or a *Methylobacterium* sp. related thereto and a strobilurin fungicide; and the second composition comprises *Methylobacterium* strain NLS0020, NLS0021, NLS0017, a derivative thereof, or a *Methylobacterium* sp. related thereto.

In certain embodiments, the methods can further comprise applying a fungicide to a plant, plant part or soil. In such embodiments, the fungicide can be applied simultaneously with one or more of the *Methylobacterium* sp. or may be applied as a separate composition to a plant or plant part. In certain embodiments, the fungicide is a strobilurin, a phenylamide, a thiazole-carboxamide, or a piperidinyl thiazole isoxazoline fungicide. In certain embodiments, the strobilurin fungicide is selected from the group consisting of azoxystrobin, pyraclostrobin, fluoxystrobin, and trifloxystrobin. In certain embodiments, the strobilurin fungicide is pyraclostrobin. In certain embodiments, the fungicide is metalaxyl, mefenoxam, ethaboxam or oxathiapiprolin. In certain embodiments of any of the aforementioned methods, the combination of *Methylobacterium*, crop, pathogen, disease, and/or antifungal compounds is as set forth in Table 4. In certain embodiments, the compositions provided herein or the plants or plant parts treated with the compositions can further comprise one or more of the aforementioned fungicides.

In certain embodiments, the *Methylobacterium* is NLS0109, a derivative thereof, or a *Methylobacterium* related to NLS0109 and the plant pathogenic fungus is a *Fusarium* sp., a *Rhizoctonia* sp., a *Colletotrichum* sp., a *Cercospora* sp., a *Septoria* sp., a *Pythium* sp., a *Puccinia* sp. or a *Sclerotinia* sp. In certain embodiments, the *Methylobacterium* is NLS0109, a derivative thereof, or a *Methylobacterium* related to NLS0109, the plant pathogenic fungus that is inhibited is *Fusarium graminearum, Septoria tritici, Stagonospora nodorum, Rhizoctonia solani*, a *Fusarium* spp., *Magnaportha grisea, Pyrenophora tritici-repentis, Microdochium nivale, Blumeria graminis* f. sp. *tritici*, or a *Pythium* sp., and the plant or plant part is a wheat plant or plant part. In certain embodiments, the *Methylobacterium* is NLS0109, a derivative thereof, or a *Methylobacterium* related to NLS0109, the plant pathogenic fungus that is inhibited is *Cercospora zeae-maydis, Colletotrichum graminicola, Fusarium graminearum, Fusarium verticillioides, Gibberella zeae, Rhizoctonia solani, Stenocarpella maydis*, a *Pythium* sp., *Sclerospora graminicola* or *Sclerophthora macrospora*, and the plant or plant part is a corn plant or corn plant part. In certain embodiments, the *Methylobacterium* is NLS0109, a derivative thereof, or a *Methylobacterium* related to NLS0109, the plant pathogenic fungus that is inhibited is *Sclerotinia sclerotiorum, Cercospora sojina, Cercospora kikuchii, Fusarium* spp., *Rhizoctonia solani, Septoria glycines, Fusarium virguliforme, Pythium* spp., *Peronospora manshurica*, or *Phytophthora sojae*, and the plant or plant part is a soybean plant or soybean plant part.

Also provided are isolated *Methylobacterium* that inhibit growth of a plant pathogenic fungus. In certain embodiments, the *Methylobacterium* sp. that inhibits growth of a plant pathogenic fungus has a 16S nucleic acid sequence having at least 97%, 98%, 99%, 99.5%, or 100% sequence identity to SEQ ID NO: 8; or the *Methylobacterium* is NLS0109 or a derivative thereof. In certain embodiments, the isolated *Methylobacterium* has in its genome one or more polynucleotide marker fragments of at least 50, 60, 100, 120, 180, 200, 240, or 300 nucleotides of SEQ ID NOS: 9-11. In certain embodiments, the isolated *Methylobacterium* has in its genome one or more marker fragments comprising a sequence having at least 98%, 99%, or 99.5% sequence identity across the entire length of SEQ ID NOS: 9-11. In certain embodiments, the plant pathogenic fungus is selected from the group consisting of a *Blumeria* sp., a *Cercospora* sp., a *Cochliobolus* sp., a *Colletotrichum* sp., a Diplodia sp., an Exserohilum sp., a Fusarium sp., a Gaeumanomyces sp., a Macrophomina sp., a Magnaporthe sp., a Microdochium sp., a Peronospora sp., a Phakopsora sp., a Phialophora sp., a Phoma sp., a Phymatotrichum sp., a Phytophthora sp., a Pyrenophora sp., a Pyricularia sp, a Pythium sp., a Rhizoctonia sp., a Sclerophthora, a Sclerospora sp., a Sclerotium sp., a Sclerotinia sp., a Septoria sp., a Stagonospora sp., a Stenocarpella sp. and a Verticillium sp.

In any of the aforementioned embodiments, the plant pathogenic fungi that is inhibited can be in its anamorphic form, its teleomorphic form, or in both its anamorphic and teleomorphic forms. The use of any of the aforementioned isolated Methylobacterium to inhibit growth of any one of the aforementioned plant pathogenic fungi is also provided herein

BRIEF DESCRIPTION OF THE DRAWINGS

The accompanying drawings, which are incorporated in and form a part of the specification, illustrate certain embodiments of the present disclosure. In the drawings.

DESCRIPTION

Definitions

Figure 1:
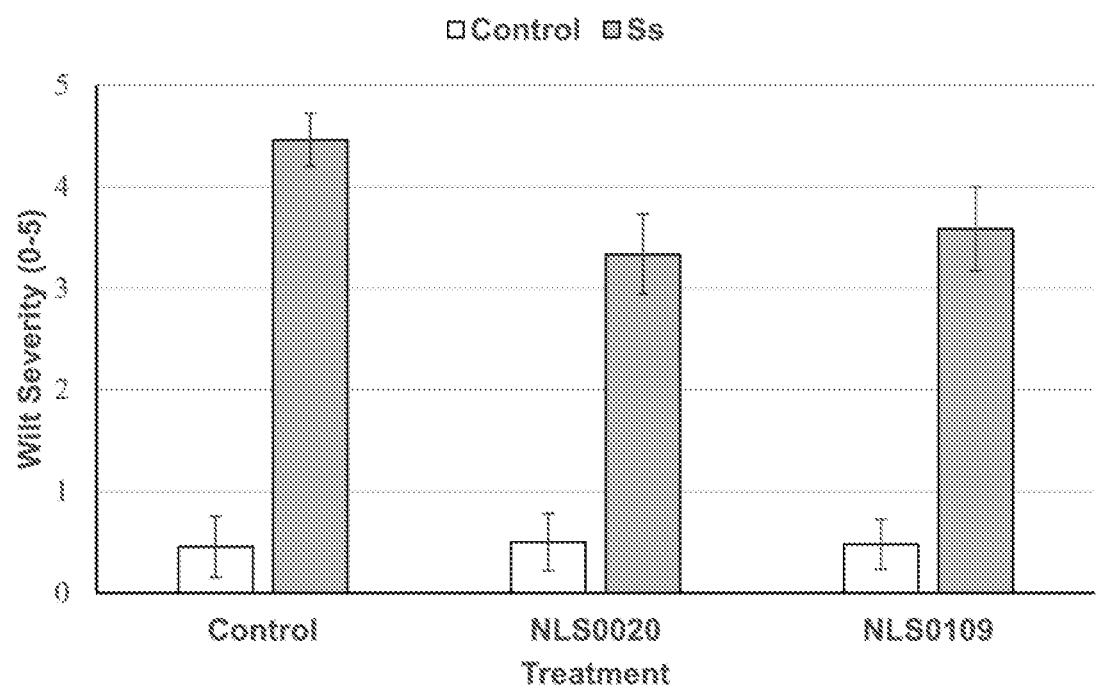
FIG. 1 is a bar chart showing suppression of soybean white mold wilt symptom severity by NLS0109. White bars represent the mean for mock-inoculated controls; gray bars represent the mean for all inoculated plants within each treatment group. Means are calculated from three independent experiments with eight replicated pots per experiment (n=24). Errors bars represent ±one SEM. Severity was rated on a 0-5 scale, with 0=no symptom development and 5=dead plant.
Figure 2:
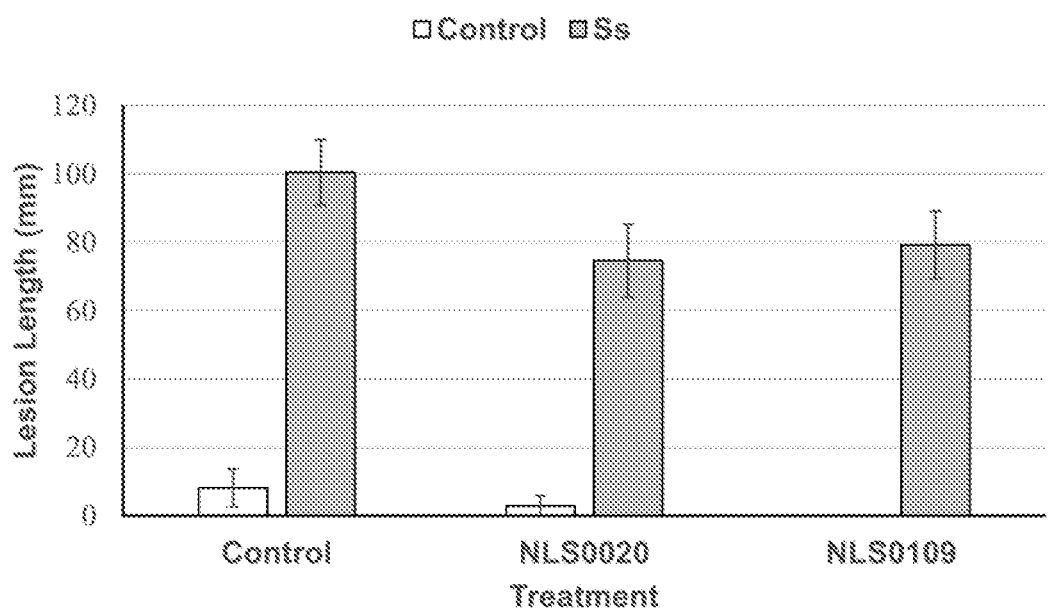
FIG. 2 is a bar chart showing suppression of soybean white mold lesion length development by NLS0109. White bars represent the mean for mock-inoculated controls; gray bars represent the mean for all inoculated plants within each treatment group. Means are calculated from three independent experiments with eight replicated pots per experiment (n=24). Errors bars represent ±one SEM. Lesion length was measured to the nearest millimeter using a ruler held against the infected plant.
Figure 3:
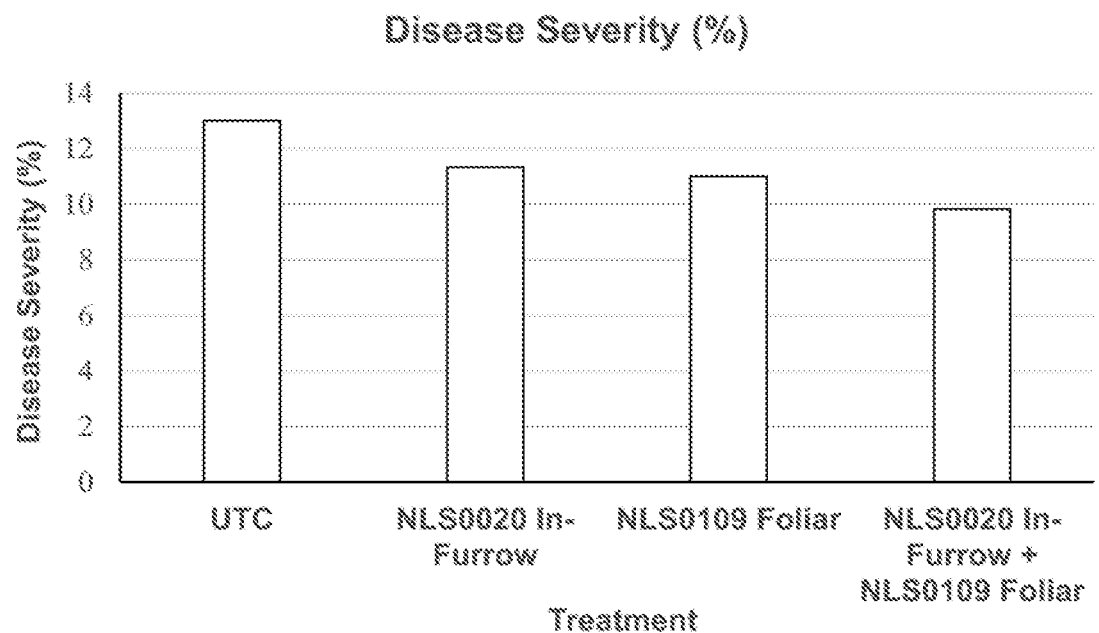
FIG. 3 is a bar chart showing the additive effect on reduction of late gray leaf spot disease severity in corn of NLS0020 in-furrow application followed by NL0109 foliar application. Applications were made during the 2015 field season at a trial site in Bethel, Mo. NLS0020 was applied in-furrow at a rate of 1,250 mL/A and NLS0109 was applied at a foliar rate of 5,000 mL/A.

As used herein, the phrases "adhered thereto" and "adherent" refer to Methylobacterium that are associated with a solid substance by growing, or having been grown, on a solid substance.

As used herein, the phrase "agriculturally acceptable adjuvant" refers to a substance that enhances the performance of an active agent in a composition comprising a mono-culture or co-culture of Methylobacterium for treatment of plants and/or plant parts.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of Methylobacterium.

As used herein, the phrase "derivatives thereof", when used in the context of a Methylobacterium strain, or isolate refers to any strain or isolate that is obtained from a given Methylobacterium strain. Derivatives of a Methylobacterium strain include, but are not limited to, variants of the strain obtained by selection, variants of the strain selected by mutagenesis and selection, variants of the strains resulting from unselected mutations resulting from growth in culture over one or more generations, and genetically transformed strains obtained from a Methylobacterium strain.

As used herein, the term "Methylobacterium" refers to bacteria that are facultative methylotrophs of the genus Methylobacterium. The term Methylobacterium, as used herein, thus does not encompass includes species in the genera Methylobacter, Methylomonas, Methylomicrobium, Methylococcus, Methylosinus, Methylocystis, Methylosphaera, Methylocaldum, and Methylocella, which are obligate methanotrophs.

As used herein, the phrase "co-culture of Methylobacterium" refers to a Methylobacterium culture comprising at least two strains of Methylobacterium or at least two species of Methylobacterium.

As used herein, the term "cultivar" refers to any plant known only in cultivation and includes asexually propagated plants, sexually propagated plants, inbred lines, and hybrids.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired Methylobacterium or other desired microorganisms of pre-determined identity.

As used herein, the phrase "a fungal inhibitory concentration of the mono- or co-culture of Methylobacterium" is a concentration that provides for at least a 40%, 50%, 75%, at least 85%, or at least 95% inhibition of a plant pathogenic fungal infection in a plant, plant part, or a plant derived therefrom relative to infection of the control plant or plant part.

As used herein, the term "heterologous", when used in the context of Methylobacterium that at least partially coats a plant or plant part, refers to a Methylobacterium that is not naturally associated with a plant or plant part of the same species as the plant or plant part that is at least partially coated with the Methylobacterium. In certain embodiments, the heterologous *Methylobacterium* that is used to at least partially coat a plant or plant part of a first plant species is a *Methylobacterium* that was isolated, or can be isolated, from a second and distinct plant species.

As used herein, the phrase "inanimate solid substance" refers to a substance which is insoluble or partially soluble in water or aqueous solutions and which is either non-living or which is not a part of a still-living organism from which it was derived.

As used herein, the phrase "a *Methylobacterium* related to NLS0109" can refer to a *Methylobacterium* that: (i) has at least one gene that encodes a 16S RNA having at least 97%, 98%, 99%, 99.5%, or 100% sequence identity to SEQ ID NO: 8; (ii) has in its genome one or more polynucleotide marker fragments of at least 50, 60, 100, 120, 180, 200, 240, or 300 nucleotides of SEQ ID NOS: 9-11; or (iii) has in its genome one or more marker fragments comprising a sequence having at least 98%, 99%, or 99.5% sequence identity across the entire length of SEQ ID NOS: 9-11.

As used herein, the phrase "mono-culture of *Methylobacterium*" refers to a *Methylobacterium* culture consisting of a single strain of *Methylobacterium*.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of the *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

*Methylobacterium* that Inhibit Plant Pathogenic Fungi, Compositions Comprising *Methylobacterium* that Inhibit Plant Pathogenic Fungi, Methods of their Use, and Methods of Making Various *Methylobacterium* that inhibit plant pathogenic fungi, compositions comprising these *Methylobacterium*, methods of using the compositions to inhibit plant pathogenic fungi, and methods of making the compositions are provided herein. As used herein, inhibition of the growth of a plant pathogenic fungus includes any measurable decrease in fungal growth, where fungal growth includes but is not limited to any measurable decrease in the numbers and/or extent of fungal cells, spores, conidia, or mycelia. As used herein, inhibition of infection by a plant pathogenic fungus and/or inhibition of the growth of a plant pathogenic fungus are also understood to include any measurable decrease in the adverse effects caused by fungal growth in a plant. Adverse effects of fungal growth in a plant include, but are not limited to, any type of plant tissue damage or necrosis, any type of plant yield reduction, any reduction in the value of the crop plant product, and/or production of undesirable fungal metabolites or fungal growth by-products including, but not limited to, mycotoxins. Plant pathogenic fungi that are inhibited by the compositions and *Methylobacterium* provided herein can be in their anamorphic form, their teleomorphic form, or in both their anamorphic and teleomorphic forms.

*Methylobacterium* and compositions comprising the same that inhibit growth of a plant pathogenic fungus are provided herein. In certain embodiments, the *Methylobacterium* or composition provides for at least about 25%, at least about 40%, at least about 50%, or at least about 75% inhibition of plant pathogenic fungal growth in comparison to a control treatment upon exposure to a plant pathogenic fungus. In certain embodiments, the plant pathogenic fungus that is inhibited is selected from the group consisting of a *Blumeria* sp., a *Cercospora* sp., a *Cochliobolus* sp., a *Colletotrichum* sp., a *Diplodia* sp., an *Exserohilum* sp., a *Fusarium* sp., a *Gaeumanomyces* sp., a *Macrophomina* sp., a *Magnaporthe* sp., a *Microdochium* sp., a *Peronospora* sp., a *Phakopsora* sp., a *Phialophora* sp., a *Phoma* sp., a *Phymatotrichum* sp., a *Phytophthora* sp., a *Pyrenophora* sp., a *Pyricularia* sp, a *Pythium* sp., a *Rhizoctonia* sp., a *Sclerophthora* sp., a *Sclerospora* sp., a *Sclerotium* sp., a *Sclerotinia* sp., a *Septoria* sp., a *Stagonospora* sp., a *Stenocarpella* sp. and a *Verticillium* sp.

In certain embodiments, the plant pathogenic fungus that is inhibited is a *Fusarium* sp. In certain embodiments, the *Fusarium* sp. that is inhibited is selected from the group consisting of *Fusarium graminearum*, *Fusarium verticillioides*, *Fusarium oxysporum*, *Fusarium virguliforme*, and *Fusarium solani*. In certain embodiments, the isolated *Methylobacterium* is NLS0109, a derivative thereof, or a *Methylobacterium* related to NLS0109. In certain embodiments, *Methylobacterium* related to NLS0109 include, but are not limited to, (i) *Methylobacterium* sp. that inhibit growth of a plant pathogenic fungus and that have a gene encoding a 16S RNA sequence that has at least 97%, 98%, 99%, 99.5%, or 100% sequence identity to SEQ ID NO:8; (ii) a *Methylobacterium* has in its genome one or more polynucleotide marker fragments of at least 50, 60, 100, 120, 180, 200, 240, or 300 nucleotides of SEQ ID NOS: 9-11; or (iii) is a *Methylobacterium* that has in its genome one or more marker fragments comprising a sequence having at least 98%, 99%, or 99.5% sequence identity across the entire length of SEQ ID NOS: 9-11. In certain embodiments, the composition further comprises *Methylobacterium* strain NLS0017, NLS0020, NLS0021, NLS0042, NLS0064, NLS0066, NLS0089, a derivative thereof, or a *Methylobacterium* sp. related thereto. Plant pathogenic fungi that are inhibited by the compositions and *Methylobacterium* provided herein can be in their anamorphic form, their teleomorphic form, or in both their anamorphic and teleomorphic forms.

Also provided are compositions that comprise *Methylobacterium* that inhibit growth of a plant pathogenic fungus. In certain embodiments, the compositions further comprise an agriculturally acceptable excipient and/or an agriculturally acceptable adjuvant. In certain embodiments, the composition provides for at least about 25%, about 50%, or about 75% inhibition of plant pathogenic fungal growth in comparison to a control treatment upon exposure to a plant pathogenic fungus. In certain embodiments, the plant pathogenic fungus that is inhibited is selected from the group consisting of a *Blumeria* sp., a *Cercospora* sp., a *Cochliobolus* sp., a *Colletotrichum* sp., a *Diplodia* sp., an *Exserohilum* sp., a *Fusarium* sp., a *Gaeumanomyces* sp., a *Macrophomina* sp., a *Magnaporthe* sp., a *Microdochium* sp., a *Peronospora* sp., a *Phakopsora* sp., a *Phialophora* sp., a *Phoma* sp., a *Phymatotrichum* sp., a *Phytophthora* sp., a *Pyrenophora* sp., a *Pyricularia* sp, a *Pythium* sp., a *Rhizoctonia* sp., a *Sclerophthora*, a *Sclerospora* sp., a *Sclerotium* sp., a *Sclerotinia* sp., a *Septoria* sp., a *Stagonospora* sp., a *Stenocarpella* sp. and a *Verticillium* sp.

In certain embodiments, the plant pathogenic fungus that is inhibited is a *Fusarium* sp. In certain embodiments, the *Fusarium* sp., which is inhibited is selected from the group consisting of *Fusarium graminearum, Fusarium verticillioides, Fusarium oxysporum, Fusarium virguliforme,* and *Fusarium solani*. In certain embodiments of any of the aforementioned compositions, the composition comprises a solid substance wherein a mono-culture or co-culture of *Methylobacterium* is adhered thereto. In certain embodiments where the *Methylobacterium* is adhered to a solid substance, the composition comprises a colloid formed by the solid substance wherein a mono-culture or co-culture of *Methylobacterium* is adhered thereto and a liquid. In certain embodiments, the colloid is a gel. In certain embodiments of certain aforementioned compositions, composition is an emulsion that does not contain a solid substance. In certain embodiments of any of the aforementioned compositions, the *Methylobacterium* sp. that inhibits growth of a plant pathogenic fungus has a gene encoding a 16S RNA sequence that has at least 97%, 98%, 99%, 99.5%, or 100% sequence identity to SEQ ID NO:8. In certain embodiments of any of the aforementioned compositions, the *Methylobacterium* is NLS0109, a derivative thereof, or a *Methylobacterium* related to NLS0109. In certain embodiments of any of the aforementioned compositions, the composition further comprises *Methylobacterium* strain NLS0017, NLS0020, NLS0021, NLS0042, NLS0064, NLS0066, NLS0089, a derivative thereof, or a *Methylobacterium* sp. related thereto. In any of the aforementioned embodiments, the plant pathogenic fungi that are inhibited can be in their anamorphic form, their teleomorphic form, or in both their anamorphic and teleomorphic forms.

In certain embodiments, the *Methylobacterium* sp. that inhibit plant pathogenic fungi can be identified by testing newly isolated candidate *Methylobacterium* sp. for the presence of polymorphic nucleic acid, orthologous gene, or gene sequences that are present in *Methylobacterium* sp. provided herein that inhibit certain plant pathogenic fungi.

Various *Methylobacterium* sp. isolates provided herein are disclosed in Table 1.

TABLE 1

*Methylobacterium* sp. isolates

| NLS | Origin | USDA ARS NRRL No.[1] |
|---|---|---|
| NLS0017 | Obtained from a peppermint plant grown in Saint Louis County, Missouri, USA | NRRL B-50931 |
| NLS0020 | Obtained from a horse nettle plant grown in Saint Louis County, Missouri, USA | NRRL B-50930 |
| NLS0021 | Obtained from a lettuce plant grown in Saint Louis Country, Missouri, USA | NRRL B-50939 |
| NLS0042 | Obtained from a soybean plant grown in Saint Louis Country, Missouri, USA | NRRL B-50932 |
| NLS0064 | Obtained from a corn plant grown in Saint Louis Country, Missouri, USA | NRRL B-50938 |
| NLS0066 | Obtained from the corn hybrid "MC534" (Masters Choice 3010 State Route 146 East Anna, IL 62906) | NRRL B-50940 |
| NLS0089 | Obtained from a broccoli plant grown in Saint Louis County, Missouri, USA | NRRL B-50933 |
| NLS0109 | Obtained from a *Yucca filamentosa* plant in Saint Louis Country, Missouri, USA | NRRL B-67340 |

[1]Deposit number for strain deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Also provided herein are methods for controlling a plant pathogenic fungus that comprise applying any of the aforementioned compositions comprising the *Methylobacterium* that are provided herein to a plant or a plant part in an amount that provides for inhibition of infection by the plant pathogenic fungus in the plant, plant part, or a plant obtained therefrom relative to infection of a control plant, plant part, or plant obtained therefrom that had not received an application of the composition. In certain embodiments, application of the composition provides for at least about 40%, at least about 50%, at least about 75%, at least about 85%, or at least about 95% inhibition of a plant pathogenic fungal infection in the plant, plant part, or a plant derived therefrom relative to infection of the control plant, plant part, or plant obtained therefrom. In certain embodiments, the plant part is selected from the group consisting of a leaf, a stem, a flower, a root, a tuber, and a seed. In certain embodiments, the method further comprises the step of harvesting at least one plant part selected from the group consisting of a leaf, a stem, a flower, a root, a tuber, or a seed from the plant or plant part. In certain embodiments of any of the aforementioned methods, the mycotoxin levels in the plant part are reduced by at least 50%, at least 75%, at least 85%, or at least 95% relative to a plant part obtained from the control plant, plant part, or plant obtained therefrom. In certain embodiments of any of the aforementioned methods, the methods further comprise obtaining a processed food or feed composition from the plant or plant part. In certain embodiments of the aforementioned methods, mycotoxin levels in the processed food or feed composition are reduced by at least 50%, at least 75%, at least 85%, or at least 95% relative to a processed food or feed composition obtained from the control plant, plant part, or plant obtained therefrom. In certain embodiments of any of the aforementioned methods, the composition comprises the *Methylobacterium* isolate NLS0109, a derivative thereof, or a *Methylobacterium* related to NLS0109. In certain embodiments of any of the aforementioned methods, the composition further comprises

*Methylobacterium* strain NLS0017, NLS0020, NLS0021, NLS0042, NLS0064, NLS0066, NLS0089, a derivative thereof, or a *Methylobacterium* sp. related thereto. In certain embodiments of any of the aforementioned methods, the composition comprises a *Methylobacterium* sp. related to NLS0109 that: (i) has at least one gene encoding a 16S RNA that has at least 97%, 98%, 99%, 99.5%, or 100% sequence identity to SEQ ID NO: 8; (ii) has in its genome one or more polynucleotide marker fragments of at least 50, 60, 100, 120, 180, 200, 240, or 300 nucleotides of SEQ ID NOS: 9-11; or (iii) has in its genome one or more marker fragments comprising a sequence having at least 98%, 99%, or 99.5% sequence identity across the entire length of SEQ ID NOS: 9-11. In certain embodiments of any of the aforementioned methods, the composition comprises a *Methylobacterium* sp. related to NLS0017, NLS0020, NLS0021, NLS0042, NLS0064, NLS0066, or NLS0089 that has at least one gene encoding a 16S RNA that has at least 97%, 98%, 99%, 99.5%, or 100% sequence identity to SEQ ID NO:1, 2, 3, 4, 5, 6, or 7, respectively.

TABLE 2

16S RNA Sequences of *Methylobacterium* strains

| NLS | SEQ ID NO | 16S RNA encoding DNA sequence |
|---|---|---|
| NLS0017 | 1 | ggtgatccagccgcaggttcccctacggctaccttgttacgactt caccccagtcgctgaccctaccgtggtcgcctgcctccttgcggt tggcgcagcgccgtcgggtaagaccaactcccatggtgtgacggg cggtgtgtacaaggcccgggaacgtattcaccgtggcatgctgat ccacgattactagcgattccgccttcatgcactcgagttgcagag tgcaatccgaactgagacggcttttggggatttgctccagatcgc tccttcgcctcccactgtcaccgccattgtagcacgtgtgtagcc catcccgtaagggccatgaggacttgacgtcatccacaccttcct cgcggcttatcaccggcagtctccctagagtgcccaactgaatga tggcaactaaggacgtgggttgcgctcgttgcgggacttaaccca acatctcacgacacgagctgacgacagccatgcagcacctgtgtg cgcgccaccgaagtggaccccaaatctctctgggtaacacgccat gtcaaaggatggtaaggttctgcgcgttgcttcgaattaaaccac atgctccaccgcttgtgcgggccccgtcaattcctttgagtttt aatcttgcgaccgtactccccaggcggaatgctcaaagcgttagc tgcgctactgcggtgcaagcacccaacagctggcattcatcgtt tacggcgtggactaccagggtatctaatcctgtttgctccccacg ctttcgcgcctcagcgtcagtaatggtccagttggccgccttcgc caccggtgttcttgcgaatatctacgaatttcacctctacactcg cagttccaccaacctctaccatactcaagcgtcccagtatcgaag gccattctgtggttgagccacaggctttcaccccgacttaaaac gccgcctacgcgcccttacgcccagtgattccgagcaacgctag ccccttcgtattaccgcggctgctggcacgaagttagccggggc ttattcctccggtaccgtcattatcgtcccggataaaagagcttt acaaccctaaggccttcatcactcacgcggcatggctggatcagg cttgcgcccattgtccaatattccccactgctgcctcccgtagga gtctgggccgtgtctcagtcccagtgtggctgatcatcctctcag accagctactgatcgtcgccttggtaggccgttaccccaccaact agctaatcagacgcgggccgatcttccggcagtaaaaccttccccc aaaagggcgtatccggtattagccctagtttcccagggttattcc gaaccagaaggcacgttcccacgcgttactcaccgtccgccgct gacccccgaaaggcccgctcgacttgcatgtgttaagcctgccgcc agcgttcgctctgagccaggatcaaactctc |
| NLS0020 | 2 | ggtgatccagccgcaggttcccctacggctaccttgttacgactt caccccagtcgctgaccctaccgtggtcgcctgcctccttgcggt tggcgcagcgccgtcgggtaagaccaactcccatggtgtgacggg cggtgtgtacaaggcccgggaacgtattcaccgtggcatgctgat ccacgattactagcgattccgccttcatgcactcgagttgcagag tgcaatccgaactgagacggcttttggggatttgctccagatcgc tccttcgcgtcccactgtcaccgccattgtagcacgtgtgtagcc catcccgtaagggccatgaggacttgacgtcatccacaccttcct cgcggcttatcaccggcagtctccctagagtgcccaactgaatga tggcaactaaggacgtgggttgcgctcgttgcgggacttaaccca acatctcacgacacgagctgacgacagccatgcagcacctgtgtg cgcgccaccgaagtggaccccaaatctctctgggtaacacgccat gtcaaaggatggtaaggttctgcgcgttgcttcgaattaaaccac atgctccaccgcttgtgcgggccccgtcaattcctttgagtttt aatcttgcgaccgtactccccaggcggaatgctcaaagcgttagc tgcgctactgcggtgcaagcacccaacagctggcattcatcgtt tacggcgtggactaccagggtatctaatcctgtttgctccccacg ctttcgcgcctcagcgtcagtaatggtccagttggccgccttcgc caccggtgttcttgcgaatatctacgaatttcacctctacactcg cagttccaccaacctctaccatactcaagcgtcccagtatcgaag gccattctgtggttgagccacaggctttcaccccgacttaaaac gccgcctacgcgcccttacgcccagtgattccgagcaacgctag ccccttcgtattaccgcggctgctggcacgaagttagccggggc ttattcctccggtaccgtcattatcgtcccggataaaagagcttt acaaccctaaggccttcatcactcacgcggcatggctggatcagg cttgcgcccattgtccaatattccccactgctgcctcccgtagga gtctgggccgtgtctcagtcccagtgtggctgatcatcctctcag |

TABLE 2-continued

16S RNA Sequences of *Methylobacterium* strains

| NLS | SEQ ID NO | 16S RNA encoding DNA sequence |
|---|---|---|
| | | accagctactgatcgtcgccttggtaggccgttaccccaccaact agctaatcagacgcgggccgatcttccggcagtaaacctttcccc aaaagggcgtatccggtattagcccctagtttcccagggttattcc gaaccagaaggcacgttcccacgcgttactcaccgtccgccgct gaccccgaagggcccgctcgacttgcatgtgttaagcctgccgcc agcgttcgctctgagccaggatcaaactctc |
| NLS0021 | 3 | gagtttgatcctggctcagagcgaacgctggcggcaggcttaaca catgcaagtcgaacgggcttcttcggaagtcagtggcagacgggt gagtaacacgtgggaacgtgcccttcggttcggaataactcaggg aaacttgagctaataccggatacgccttatggggaaaggtttac tgccgaaggatcggcccgcgtctgattagcttgttggtgggtaa cggcctaccaaggcgacgatcagtagctggtctgagaggatgatc agccacactgggactgagacacggcccagactcctacgggaggca gcagtggggaatattggacaatgggcgcaagcctgatccagccat gccgcgtgagtgatgaaggccttagggttgtaaagctcttttgtc cgggacgataatgacggtaccggaagaataagccccggctaactt cgtgccagcagccgcggtaatacgaaggggctagcgttgctcgg aatcactgggcgtaaagggcgcgtaggcggccgattaagtcgggg gtgaaagcctgtggctcaaccacagaattgccttcgatactggtt ggcttgagaccggaagaggacagcggaactgcgagtgtagaggtg aaattcgtagatattcgcaagaacaccagtggcgaaggcggctgt ctggtccggttctgacgctgaggcgcgaaagcgtggggagcaaac aggattagataccctggtagtccacgccgtaaacgatgaatgcca gccgttggtctgcttgcaggtcagtggcgccgctaacgcattaag cattccgcctggggagtacggtcgcaagattaaaactcaaaggaa ttgacggggcccgcacaagcggtggagcatgtggtttaattcga agcaacgcgcagaaccttaccatcccttgacatggcatgttacct cgagagatcgggatcctcttcggaggcgtgcacacaggtgctgc atggctgtcgtcagctcgtgtcgtgagatgttgggttaagtcccg caacgagcgcaacccacgtccttagttgccatcattcagttgggc actctaggagactgccggtgataagccgcgaggaaggtgtggat gacgtcaagtcctcatggcccttacgggatgggctacacacgtgc tacaatggcggtgacagtgggacgcgaaaccgcgaggttgagcaa atccccaaaagccgtctcagttcggattgcactctgcaactcggg tgcatgaaggcggaatcgctagtaatcgtggatcagcacgccacg gtgaatacgttcccgggccttgtacacaccgcccgtcacaccatg ggagttggtcttacccgacggcgctgcgccaaccgcaaggggca ggcgaccacggtagggtcagcgactggggtgaagtcgtaacaagg tagccgtaggggaacctgcggctggatcacct |
| NLS0042 | 4 | ggtgatccagccgcaggttcccctacggctaccttgttacgactt cacccccagtcgctgaccctaccgtggtcgcctgcctccttgcggt tggcgcagcgccgtcgggtaagaccaactcccatggtgtgacggg cggtgtgtacaagggcccgggaacgtattcaccgtggcgtgctgat ccacgattactagcgattccgccttcatgcacccgagttgcagag tgcaatccgaactgagacggtttttggggatttgctccacctcgc ggcttcgcgtcccactgtcaccgccattgtagcacgtgtgtagcc catcccgtaagggccatgaggacttgacgtcatccacaccttcct cgcggcttatcaccggcagtctccctagagtgcccaactgaatga tggcaactaaggacgtgggttgcgctcgttgcgggacttaaccca acatctcacgacacgagctgacgacagccatgcagcacctgtgtg cacgcctccgaagaggatccccgatctctcgaggtaacatgccat gtcaagggatggtaaggttctgcgcgttgcttcgaattaaaccac atgctccaccgcttgtgcgggcccccgtcaattcctttgagttttt aatcttgcgaccgtactccccaggcggaatgcttaatgcgttagc ggcgcactgacctgcaagcaggccaacggctggcattcatcgtt tacggcgtggactaccagggtatctaatcctgtttgctccccacg ctttcgcgcctcagcgtcagaaccggaccagacagccgccttcgc cactggtgttcttgcgaatatctacgaatttcacctctacactcg cagttccgctgtcctcttccggtctcaagcaaccagtatcgaag gcaattctgtggttgagccacaggctttcaccccccgacttaatcg gccgcctacgcgcccttacgcccagtgattccgagcaacgctag ccccccttcgtattaccgcggctgctggcacgaagttagccgggc ttattcttccggtaccgtcattatcgtcccggacaaaagagcttt acaaccctaaggccttcatcactcacgcggcatggctggatcagg cttgcgcccattgtccaatattccccactgctgcctcccgtagga gtctgggccgtgtctcagtcccagtgtggctgatcatcctctcag accagctactgatcgtcgccttggtaggccgttaccccaccaaca agctaatcagacgcgggccgatcttcggcagtaaacctttcccc aaaagggcgtatccggtattagctcaagtttccctgagttattcc gaaccgaagggtacgttcccacgtgttactcaccgtctgccact gacacccgaaggtgcccgttcgacttgcatgtgttaagcctgccg ccagcgttcgctctgagccaggatcaaactctc |

TABLE 2-continued

16S RNA Sequences of *Methylobacterium* strains

| NLS | SEQ ID NO | 16S RNA encoding DNA sequence |
|---|---|---|
| NLS0064 | 5 | ggtgatccagccgcaggttcccctacggctaccttgttacgactt cacccccagtcgctgaccctaccgtggtcgcctgcctccagtcgag caagctcgatttggttggcgcagcgccgtcgggtaagaccaactc ccatggtgtgacgggcggtgtgtacaaggcccgggaacgtattca ccgtggcatgctgatccacgattactagcgattccgccttcatgc acgcgagttgcagcgtgcaatccgaactgagacggcttttggaga ttggctccgggtcacccctttcgcgtcccactgtcaccgccattgt agcacgtgtgtagcccatcccgtaagggccatgaggacttgacgt catccacaccttcctcgcggcttatcaccggcagtctcctagag tgcccaaccaaatgatggcaactaaggacgtgggttgcgctcgtt gcgggacttaacccaacatctcacgacacgagctgacgacagcca tgcagcacctgtgtgcgcgcccccgaaggggacctggaatctctc ccagtaacacgccatgtcaaaggatggtaaggttctgcgcgttgc ttcgaattaaaccacatgctccaccgcttgtgcgggcccccgtca attcctttgagttttaatcttgcgaccgtactccccaggcggaat gcttaatgcgttagctgcgctactgcggtgcatgcaccccaacag ctagcattcatcgtttacggcgtggactaccagggtatctaatcc tgtttgctccccacgctttcgcgcctcagcgtcagtaatggtcca gttggccgccttcgccaccggtgttcttgcgaatatctacgaatt tcacctctacactcgcagttccaccaacctctaccatactcaagc gtcccagtatcgaaggccattctgtggttgagccacaggctttca cccccgacttaaaacgccgcctacgcgccctttacgcccagtgat tccgagcaacgctagccccttcgtattaccgcggctgctggcac gaagttagccggggcttattcctccggtaccgtcattatcgtccc ggagaaaagagctttacaaccctaaggccgtcatcactcacgcgg catggctggatcaggcttgcgccattgtccaatattccccactg ctgcctcccgtaggagtctgggccgtgtctcagtcccagtgtggc tgatcatcctctcagaccagctactgatcgtcgccttggtaggcc gttaccccaccaacaagctaatcagacgcgggccgatcctccggc agtaaacctttctgccaaagcacgtatccggtattagccctagtt tcccagggttatcccagaccggagggcacgttcccacgtgttact caccccgtctgccactcaccttgcggtgcgttcgacttgcatgtgt taagcctgccgccagcgttcgctctgagccaggatcaaactctc |
| NLS0066 | 6 | gagtttgatcctggctcagagcgaacgctggcggcaggcttaaca catgcaagtcgaacgcaccgcaaggtgagtggcagacgggtgagt aacacgtgggaacgtgcccteeggtctgggataaccctgggaaac tagggctaataccggatacgtgctttggcagaaaggtttactgcc ggaggatcggcccgcgtctgattagcttgttggtggggtaacggc ctaccaaggcgacgatcagtagctggtctgagaggatgatcagcc acactgggactgagacacggcccagactcctacgggaggcagcag tggggaatattggacaatgggcgcaagcctgatccagccatgccg cgtgagtgatgacggccttagggttgtaaagctcttttctccggg acgataatgacggtaccggaggaataagccccggctaacttcgtg ccagcagccgcggtaatacgaaggggcgtagcgttgctcggaatc actgggcgtaaagggcgcgtaggcggcgttttaagtcggggtga aagcctgtggctcaaccacagaatggccttcgatactgggacgct tgagtatggtagaggttggtggaactgcgagtgtagaggtgaaat tcgtagatattcgcaagaacaccggtggcgaaggcggccaactgg accattactgacgctgaggcgcgaaagcgtggggagcaaacagga ttagataccctggtagtccacgccgtaaacgatgaatgctagctg ttggggtgcatgcaccgcagtagcgcagctaacgcattaagcatt ccgcctggggagtacggtcgcaagattaaaactcaaaggaattga cgggggcccgcacaagcggtggagcatgtggtttaattcgaagca acgcgcagaaccttaccatcctttgacatggcgtgttactgggag agattccaggtcccctteggggggcgcgcacacaggtgctgcatg ctgtcgtcagctcgtgtcgtgagatgttgggttaagtcccgcaac gagcgcaacccacgtccttagttgccatcatttggttgggcactc tagggagactgccggtgataagccgcgaggaaggtgtggatgacg tcaagtcctcatggcccttacgggatgggctacacacgtgctaca atggcggtgacagtgggacgcgaaggggtgacccggagccaatct ccaaaaagccgtctcagttcggattgcacgctgcaactcgcgtgca tgaaggcggaatcgctagtaatcgtggatcagcatgccacggtga atacgttcccgggccttgtacacaccgcccgtcacaccatgggga ttggtcttacccgacggcgctgcgccaaccaaatcgagcttgctc gactggaggcaggcgaccacggtagggtcagcgactgggtgaag tcgtaacaaggtagccgtaggggaacctgcggctggatcacctc |
| NLS0089 | 7 | gagtttgatcctggctcagagcgaacgctggcggcaggcttaaca catgcaagtcgaacgggcttcttcggaagtcagtggcagacgggt gagtaacacgtgggaacgtgcccttcggttcggaataactcaggg aaacttgagctaataccggatacgcccttacggggaaaggtttac tgccgaaggatcggcccgcgtctgattagcttgttggtggggtaa |

TABLE 2-continued

16S RNA Sequences of *Methylobacterium* strains

| NLS | SEQ ID NO | 16S RNA encoding DNA sequence |
|---|---|---|
| | | cggcctaccaaggcgacgatcagtagctggtctgagaggatgatc<br>agccacactgggactgagacacggcccagactcctacgggaggca<br>gcagtggggaatattggacaatgggcgcaagcctgatccagccat<br>gccgcgtgagtgatgaaggccttaggg ttgtaaagctcttttgtc<br>cgggacgataatgacggtaccggaagaataagccccggctaactt<br>cgtgccagcagccgcggtaatacgaaggggg ctagcgttgctcgg<br>aatcactgggcgtaaagggcgcgtaggcggccgattaagtcgggg<br>gtgaaagcctgtggctcaaccacagaattgccttcgatactggtt<br>ggcttgagaccggaagaggacagcggaactgcgagtgtagaggtg<br>aaattcgtagatattcgcaagaacaccagtggcgaaggcggctgt<br>ctggtccggttctgacgctgaggcgcgaaagcgtggggagcaaac<br>aggattagataccctggtagtccacgccgtaaacgatgaatgcca<br>gccgttggtctgcttgcaggtcagtggcgccgctaacgcattaag<br>cattccgcctggggagtacggtcgcaagattaaaactcaaaggaa<br>ttgacggggg cccgcacaagcggtggagcatgtggtttaattcga<br>agcaacgcgcagaaccttaccatcccttgacatggcatgttacct<br>cgagagatcggggatcctcttcggaggcgtgcacacaggtgctgc<br>atggctgtcgtcagctcgtgtcgtgagatgttgggttaagtcccg<br>caacgagcgcaacccacgtccttagttgccatcattcagttgggc<br>actctaggg agactgccggtgataagccgcgaggaaggtgtggat<br>gacgtcaagtcctcatggcccttacgggatgggctacacacgtgc<br>tacaatggcggtgacagtgggacgcgaaaccgcgaggttgagcaa<br>atccccaaaagccgtctcagttcggattgcactctgcaactcggg<br>tgcatgaaggcggaatcgctagtaatcgtggatcagcacgccacg<br>gtgaatacgttcccgggccttgtacacaccgcccgtcacaccatg<br>ggagttggtcttacccgacggcgctgcgccaaccgcaagggggca<br>ggcgaccacggtagggtcagcgactggggtgaagtcgtaacaagg<br>tagccgtaggggaacctgcggctggatcacct |
| NLS0109 | 8 | ggtgatccagccgcaggttccc ctacggctaccttgttacgactt<br>caccccagtcgctgaccctaccgtggtcgcctgctcccc ttgcgg<br>gtcggcgcagcgccgtcgggtaagaccaactcccatggtgtgacg<br>ggcggtgtgtacaaggcccgggaacgtattcaccgtggcatgctg<br>atccacgattactagcgattccgccttcatgcactcgagttgcag<br>agtgcaatccgaactgagacggcttttggagatttgcttgccctc<br>gcgggttcgcgtcccactgtcaccgccattgtagcacgtgtgtag<br>cccatcccgtaagggccatgaggacttgacgtcatccacaccttc<br>ctcgcggcttatcaccggcagtctccccagagtgcccaactgaat<br>gatggcaactgaggacgtgggttgcgctcgttgcgggacttaacc<br>caacatctcacgacacgagctgacgacagccatgcagcacctgtg<br>tgcgcgctcccgaaggagaccgtggatctctccacgtaacacgcc<br>atgtcaaaggatggtaaggttctgcgcgttgcttcgaattaaacc<br>acatgctccaccgcttgtgcgggcccccgtcaattcctttgagtt<br>ttaatcttgcgaccgtactccccaggcggaatgctcaaagcgtta<br>gctgcgccactgagaggcaagcccccc aacggctggcattcatcg<br>tttacggcgtggactaccagggtatctaatcctgtttgctcccca<br>cgctttcgcgcctcagcgtcagtgtcggaccagttggccgccttc<br>gccaccggtgttcttgcgaatatctacgaatttcacctctacact<br>cgcagttccaccaacctcttccgaactcaagtctcccagtatcga<br>aggcaattctgtggttgagccacaggctttcaccccgacttaaa<br>agaccgcctacgcgccctttacgcccagtgattccgagcaacgct<br>agccccctt cgtattaccgcggctgctggcacgaagttagccggg<br>gcttattcctccggtaccgtcattatcgtcccggataaaagagct<br>ttacaaccctaaggccttcatcactcacgcggcatggctggatca<br>ggcttgcgcccattgtccaatattccccactgctgcctcccgtag<br>gagtctgggccgtgtctcagtcccagtgtggctgatcatcctctc<br>agaccagctactgatcgtcgccttggtaggccgttaccccaccaa<br>ctagctaatcagacgcgggccgatcttccggcagtaaacctttcc<br>ccaaaaggcgtatccggtattagctcaagtttccctgagttatt<br>ccgaaccagaaggcacgttcccacgcgttactcaccc gtccgccg<br>ctgacaccgaagtgcccgctcgacttgcatgtgttaagcctgccg<br>ccagcgttcgctctgagccaggatcaaactctc |

Also provided are methods of making the compositions useful for controlling plant pathogenic fungi that comprise combining a *Methylobacterium* that inhibit growth of a plant pathogenic fungus with an agriculturally acceptable excipient and/or with an agriculturally acceptable adjuvant. In certain embodiments of the methods, the *Methylobacterium* is not *M. radiotolerans* or *M. oryzae*. In certain embodiments of any of the aforementioned methods, the composition comprises a *Methylobacterium* sp. related to NLS0109 that has; (i) at least one gene encoding a 16S RNA that has at least 97%, 98%, 99%, 99.5%, or 100% sequence identity to SEQ ID NO: 8; (ii) in its genome one or more polynucleotide marker fragments of at least 50, 60, 100, 120, 180, 200, 240, or 300 nucleotides of SEQ ID NOS: 9-11; or (iii) in its genome one or more marker fragments comprising a sequence having at least 98%, 99%, or 99.5% sequence identity across the entire length of SEQ ID NOS: 9-11. In certain embodiments of any of the aforementioned methods, the composition comprises the *Methylobacterium* isolate NLS0109, a derivative thereof, or a *Methylobacterium* related to NLS0109. In certain embodiments of any of the aforementioned methods, the composition further comprises *Methylobacterium* strain NLS0017, NLS0020, NLS0021, NLS0042, NLS0064, NLS0066, NLS0089, a derivative thereof, or a *Methylobacterium* sp. related thereto. In certain embodiments of the methods, the compositions provide for at least about 25%, at least about 50%, or at least about 75% inhibition of plant pathogenic fungal growth in comparison to a control composition that lacks *Methylobacterium* that inhibit a plant pathogenic fungus upon exposure to the plant pathogenic fungus. In certain embodiments of the methods, the plant pathogenic fungus is selected from the group consisting of a *Blumeria* sp., a *Cercospora* sp., a *Cochliobolus* sp., a *Colletotrichum* sp., a *Diplodia* sp., an *Exserohilum* sp., a *Fusarium* sp., a *Gaeumanomyces* sp., a *Macrophomina* sp., a *Magnaporthe* sp., a *Microdochium* sp., a *Peronospora* sp., a *Phakopsora* sp., a *Phialophora* sp., a *Phoma* sp., a *Phymatotrichum* sp., a *Phytophthora* sp., a *Pyrenophora* sp., a *Pyricularia* sp, a *Pythium* sp., a *Rhizoctonia* sp., a *Sclerophthora*, a *Sclerospora* sp., a *Sclerotium* sp., a *Sclerotinia* sp., a *Septoria* sp., a *Stagonospora* sp., a *Stenocarpella* sp. and a *Verticillium* sp.

In certain embodiments of the methods, the *Fusarium* sp. is selected from the group consisting of *Fusarium graminearum, Fusarium verticillioides, Fusarium oxysporum*, and *Fusarium solani*. In certain embodiments of the methods, the *Methylobacterium* is adhered to a solid substance. In certain embodiments of the methods, the *Methylobacterium* adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion. In certain embodiments of any of the aforementioned methods, the plant pathogenic fungus is a *Fusarium* sp. and/or the plant is a cereal plant. In certain embodiments of any of the aforementioned methods, the plant pathogenic fungus is a *Fusarium* sp. and the plant is a cereal plant selected from the group consisting of a rice, wheat, corn, barley, millet, sorghum, oat, and rye plant. In certain embodiments of any of the aforementioned methods, the plant pathogenic fungus is *Fusarium graminearum* and the plant is a cereal plant selected from the group consisting of a rice, wheat, corn, barley, millet, sorghum, oat, and rye plant. In any of the aforementioned embodiments, the plant pathogenic fungi that is inhibited can be in its anamorphic form, its teleomorphic form, or in both its anamorphic and teleomorphic forms.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5 carbons and sterols; (4) an animal oil, microbial oil, synthetic oil, plant oil, or combination thereof; and/or, (5) a plant oil selected from the group consisting of corn, soybean, cotton, peanut, sunflower, olive, flax, coconut, palm, rapeseed, sesame seed, safflower, and combinations thereof. In certain embodiments, the immiscible or partially immiscible liquid can comprise at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned US Patent Application Publication No. 20130324407, which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the *Methylobacterium* in an emulsion under conditions that provide for *Methylobacterium* growth. Medias comprising the emulsion and *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5, 6, or 7 carbons and sterols; (4) an animal oil, microbial oil, synthetic oil, plant oil, or combination thereof; and/or, (5) a plant oil selected from the group consisting of corn, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned U.S. patent application Ser. No. 14/894,568, filed May 30, 2014, which is incorporated herein by reference in its entirety.

In certain embodiments, the fermentation broth, fermentation broth product, or compositions that comprise *Methylobacterium* that inhibit plant pathogenic fungi can further comprise one or more introduced microorganisms of predetermined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp., as well as bioinoculants for improved nitrogen fixation, including *rhizobia* species such as from *Rhizobium* or *Bradyrhizobium*, Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma vixens*, and *Streptomyces lydicus* strains. Other microorganisms that are added can be genetically engineered or isolates that are available as pure cultures. In certain embodiments, it is anticipated that the bacterial or fungal microorganism can be provided in the fermentation broth, fermentation broth product, or composition in the form of a spore.

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Examples of liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

Fermentation products and compositions with a mono- or co-culture of *Methylobacterium* that inhibit plant pathogenic fungi at a titer of greater than about $5\times10^7$ colony-forming units per milliliter, at a titer of greater than about $1\times10^8$ colony-forming units per milliliter, at a titer of greater than about $5\times10^8$ colony-forming units per milliliter, at a titer of greater than about $1\times10^9$ colony-forming units per milliliter, at a titer of greater than about $1\times10^{10}$ colony-forming units per milliliter, at a titer of at least about $3\times10^{10}$ colony-forming units per milliliter are provided herein. In certain embodiments, fermentation products and compositions provided herein can comprise *Methylobacterium* that inhibit plant pathogenic fungi at a titer of at least about $5\times10^7$, $1\times10^8$, or $5\times10^8$ colony-forming units per milliliter to at least about $3\times10^{10}$ colony-forming units per milliliter, at least about $5\times10^8$ colony-forming units per milliliter to at least about $4\times10^{10}$ colony-forming units per milliliter, or at least about $5\times10^8$ colony-forming units per milliliter to at least about $6\times10^{10}$ colony-forming units per milliliter. In certain embodiments, fermentation products and compositions provided herein can comprise *Methylobacterium* that inhibit plant pathogenic fungi at a titer of at least about $1\times10^9$ colony-forming units per milliliter to at least about $3\times10^{10}$ colony-forming units per milliliter, at least about $1\times10^9$ colony-forming units per milliliter to at least about $4\times10^{10}$ colony-forming units per milliliter, or at least about $1\times10^9$ colony-forming units per milliliter to at least about $6\times10^{10}$ colony-forming units per milliliter. In certain embodiments, fermentation products and compositions provided herein will comprise *Methylobacterium* that inhibit plant pathogenic fungi at a titer of at least about $1\times10^{10}$ colony-forming units per milliliter to at least about $3\times10^{10}$ colony-forming units per milliliter, at least about $1\times10^{10}$ colony-forming units per milliliter to at least about $4\times10^{10}$ colony-forming units per milliliter, or at least about $1\times10^{10}$ colony-forming units per milliliter to at least about $6\times10^{10}$ colony-forming units per milliliter. In certain embodiments, fermentation products and compositions provided herein will comprise *Methylobacterium* that inhibit plant pathogenic fungi at a titer of, at least about $3\times10^{10}$ colony-forming units per milliliter to at least about $4\times10^{10}$ colony-forming units per milliliter, or at least about $3\times10^{10}$ colony-forming units per milliliter to at least about $6\times10^{10}$ colony-forming units per milliliter. In any of the aforementioned fermentation products or compositions, the indicated concentrations can be fungal inhibitory concentrations. In any of the aforementioned fermentation products or compositions, the fermentation products or compositions can be essentially free of contaminating microorganisms, can comprise *Methylobacterium* that are adhered to and/or associated with materials that the *Methylobacterium* are not are adhered to and/or associated with in nature, or any combination thereof.

Fermentation products and compositions with *Methylobacterium* that inhibit plant pathogenic fungi at a titer of greater than about $5 \times 10^7$, $1 \times 10^8$, or $5 \times 10^8$ colony-forming units per gram, at a titer of greater than about $1 \times 10^9$ colony-forming units per gram, at a titer of greater than about $1 \times 10^{10}$ colony-forming units per gram, at a titer of at least about $3 \times 10^{10}$ colony-forming units per gram are provided herein. In certain embodiments, fermentation products and compositions provided herein can comprise *Methylobacterium* that inhibit plant pathogenic fungi at a titer of at least about $5 \times 10^7$, $1 \times 10^8$, or $5 \times 10^8$ colony-forming units per gram to at least about $3 \times 10^{10}$ colony-forming units per gram, at least about $5 \times 10^7$, $1 \times 10^8$, or $5 \times 10^8$ colony-forming units per gram to at least about $4 \times 10^{10}$ colony-forming units per gram, or at least about $5 \times 10^7$, $1 \times 10^8$, or $5 \times 10^8$ colony-forming units per gram to at least about $6 \times 10^{10}$ colony-forming units per gram. In certain embodiments, fermentation products and compositions provided herein can comprise *Methylobacterium* that inhibit plant pathogenic fungi at a titer of at least about $1 \times 10^9$ colony-forming units per gram to at least about $3 \times 10^{10}$ colony-forming units per gram, at least about $1 \times 10^9$ colony-forming units per gram to at least about $4 \times 10^{10}$ colony-forming units per gram, or at least about $1 \times 10^9$ colony-forming units per gram to at least about $6 \times 10^{10}$ colony-forming units per gram. In certain embodiments, fermentation products and compositions provided herein will comprise *Methylobacterium* that inhibit plant pathogenic fungi at a titer of at least about $1 \times 10^{10}$ colony-forming units per gram to at least about $3 \times 10^{10}$ colony-forming units per gram, at least about $1 \times 10^{10}$ colony-forming units per gram to at least about $4 \times 10^{10}$ colony-forming units per gram, or at least about $1 \times 10^{10}$ colony-forming units per gram to at least about $6 \times 10^{10}$ colony-forming units per gram. In certain embodiments, fermentation products and compositions provided herein will comprise *Methylobacterium* that inhibit plant pathogenic fungi at a titer of, at least about $3 \times 10^{10}$ colony-forming units per gram to at least about $4 \times 10^{10}$ colony-forming units per gram, or at least about $3 \times 10^{10}$ colony-forming units per gram to at least about $6 \times 10^{10}$, $1 \times 10^{11}$, $1 \times 10^{12}$, $1 \times 10^{13}$, or $5 \times 10^{13}$ colony-forming units per gram. In any of the aforementioned fermentation products or compositions, the fermentation or composition can comprise a mono- or co-culture of *Methylobacterium* that is adhered to a solid substance. In any of the aforementioned fermentation products or compositions, the indicated concentrations can be fungal inhibitory concentrations. In any of the aforementioned fermentation products or compositions, the indicated concentrations can be fungal inhibitory concentrations. In any of the aforementioned fermentation products or compositions, the fermentation products or compositions can be essentially free of contaminating microorganisms, can comprise *Methylobacterium* that are adhered to and/or associated with materials that the *Methylobacterium* are not are adhered to and/or associated with in nature, or any combination thereof.

*Methylobacterium* that inhibit plant pathogenic fungi can be obtained as fermentation products can be used to make various compositions useful for treating plants or plant parts to inhibit infection by plant pathogenic fungi. Alternatively, compositions provided herein comprising solid substances with *Methylobacterium* that inhibit plant pathogenic fungi or adherent *Methylobacterium* that inhibit plant pathogenic fungi can be used to treat plants or plant parts. Plants, plant parts, and, in particular, plant seeds that have been at least partially coated with the fermentation broth products or compositions comprising *Methylobacterium* that inhibit plant pathogenic fungi are thus provided. Also provided are processed plant products that contain the fermentation broth products or compositions with *Methylobacterium* that inhibit plant pathogenic fungi or adherent *Methylobacterium* that inhibit plant pathogenic fungi. *Methylobacterium* that inhibit plant pathogenic fungi can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the fermentation product or composition that at least partially coats the plant, plant part, or plant seed or that is contained in the processed plant, plant part, or seed product comprises a *Methylobacterium* that inhibit plant pathogenic fungi that can be readily identified by comparing a treated and an untreated plant, plant part, plant seed, or processed product thereof. In certain embodiments, the identification is performed by determining if the fermentation product or composition that at least partially coats the plant, plant part, or plant seed or that is contained in the processed plant, plant part, or seed product comprises a *Methylobacterium* sp. related to NLS0109 that: (i) has at least one gene encoding a 16S RNA that has at least 97%, 98%, 99%, 99.5%, or 100% sequence identity to SEQ ID NO: 8; (ii) has in its genome one or more polynucleotide marker fragments of at least 50, 60, 100, 120, 180, 200, 240, or 300 nucleotides of SEQ ID NOS: 9-11; or (iii) has in its genome one or more marker fragments comprising a sequence having at least 98%, 99%, or 99.5% sequence identity across the entire length of SEQ ID NOS: 9-11. Similar 16S RNA sequence analyses can be conducted to determine if the fermentation product or composition that at least partially coats the plant, plant part, or plant seed or that is contained in the processed plant, plant part, or seed product further comprises NLS0017, NLS0020, NLS0021, NLS0042, NLS0064, NLS0066, NLS0089, a derivative thereof, or a *Methylobacterium* sp. related thereto.

Compositions useful for treating plants or plant parts that comprise *Methylobacterium* that inhibit plant pathogenic fungi or a solid substance with adherent *Methylobacterium* that inhibit plant pathogenic fungi, emulsions containing the *Methylobacterium* that inhibit plant pathogenic fungi or combinations thereof can also comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension.

Agriculturally acceptable adjuvants used in the compositions that comprise *Methylobacterium* that inhibit plant pathogenic fungi, emulsions containing the *Methylobacterium* that inhibit plant pathogenic fungi, or combinations thereof include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants, extenders, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions comprising *Methylobacterium* that inhibit plant pathogenic fungi, or combinations thereof are also provided herein. Treated plants, and treated plant parts obtained therefrom, include, but are not limited to, corn, *Brassica* sp. (e.g., *B. napus, B. rapa, B. juncea*), alfalfa, rice, rye, sorghum, millet (e.g., pearl millet (*Pennisetum glaucum*)), proso millet (*Panicum miliaceum*), foxtail millet (*Setaria italica*), finger millet (*Eleusine coracana*), sunflower, safflower, soybean, tobacco, potato, peanuts, cotton, sweet potato (*Ipomoea batatas*), cassava, coffee, coconut, pineapple, citrus trees, cocoa, tea, banana, avocado, fig, guava, mango, olive, *papaya*, cashew, macadamia, almond, sugar beets, sugarcane, oats, barley, tomatoes, lettuce, green beans, lima beans, peas, cucurbits such as cucumber, cantaloupe, and musk melon, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, *hydrangea*, hibiscus, roses, tulips, daffodils, petunias, carnation, poinsettia, and *chrysanthemum*. Conifer plants and plant parts that can be treated include, but are not limited to, pines such as loblolly pine, slash pine, ponderosa pine, lodge pole pine, and Monterey pine; Douglas-fir; Western hemlock; Sitka spruce; redwood; true firs such as silver fir and balsam fir; and cedars such as Western red cedar and Alaska yellow-cedar. Turfgrass plants and plant parts that can be treated include, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and *zoysia* grass. In certain embodiments, the treated plant or plant part is a cereal plant or plant part selected from the group consisting of a rice, wheat, corn, barley, millet, sorghum, oat, and rye plant or plant part. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions that comprise *Methylobacterium* that inhibit plant pathogenic fungi, or combinations thereof as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with *Methylobacterium* that inhibit plant pathogenic fungi adhered thereto are also provided herein. Also provided herein are processed plant products that comprise a solid substance with *Methylobacterium* that inhibit plant pathogenic fungi adhered thereto.

In certain embodiments, seeds are treated by exposing the seeds to the fermentation broths, fermentation broth products, fermentation products, and compositions that comprise *Methylobacterium* that inhibit plant pathogenic fungi, or combinations thereof. Seeds can be treated with the fermentation broths, fermentation broth products, and compositions provided herein by methods including, but not limited to, imbibition, coating, spraying, and the like. Seed treatments can be effected with both continuous and/or a batch seed treaters. In certain embodiments, the coated seeds can be prepared by slurrying seeds with a coating composition containing a fermentation broth, fermentation broth product, or compositions that comprise the solid substance with *Methylobacterium* that inhibit plant pathogenic fungi and air drying the resulting product. Air drying can be accomplished at any temperature that is not deleterious to the seed or the *Methylobacterium*, but will typically not be greater than 30 degrees Centigrade. The proportion of coating that comprises a solid substance and *Methylobacterium* that inhibit plant pathogenic fungi includes, but is not limited to, a range of 0.1 to 25% by weight of the seed, 0.5 to 5% by weight of the seed, and 0.5 to 2.5% by weight of seed. In certain embodiments, a solid substance used in the seed coating or treatment will have *Methylobacterium* that inhibit plant pathogenic fungi adhered thereon. In certain embodiments, a solid substance used in the seed coating or treatment will be associated with *Methylobacterium* that inhibit plant pathogenic fungi and will be a fermentation broth, fermentation broth product, or composition obtained by the methods provided herein. Various seed treatment compositions and methods for seed treatment disclosed in U.S. Pat. Nos. 5,106,648; 5,512,069; and 8,181,388 are incorporated herein by reference in their entireties and can be adapted for use with fermentation products or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with a fermentation products or compositions provided herein.

Provided herein are compositions that comprise *Methylobacterium* that inhibit plant pathogenic fungi and that provide control of plant pathogenic fungal infections of plants, plant parts, and plants obtained therefrom relative to untreated plants, plant parts, and plants obtained therefrom that have not been exposed to the compositions. In certain embodiments, plant parts, including, but not limited to, a seed, a leaf, a fruit, a stem, a root, a tuber, or a coleoptile can be treated with the compositions provided herein to control fungal disease. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for fungal disease inhibition in a plant or plant part in comparison to an untreated plant or plant part. Such fungal disease inhibition includes, but is not limited to decreases in fungal growth and/or the adverse effects of fungal growth relative to untreated plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Amounts of the compositions that comprise *Methylobacterium* that inhibit plant pathogenic fungi that are sufficient to provide for an inhibition of fungal infection of a plant or plant part can thus be determined by measuring any or all fungal growth and/or the adverse effects of fungal growth in treated plants or plant parts relative to untreated plants or plant parts. Adverse effects of fungal growth in a plant that can be measured include any type of plant tissue damage or necrosis, any type of plant yield reduction, any reduction in the value of the crop plant product, and/or production of undesirable fungal metabolites or fungal growth by-products including, but not limited to, mycotoxins. Mycotoxins comprise a number of toxic molecules produced by fungal species, including, but not limited to, polyketides (including aflatoxins, demethylsterigmatocystin, O-methylsterigmatocystin etc.), fumonisins, alperisins (e.g., $A_1$, $A_2$, $B_1$, $B_2$), sphingofungins (A, B, C and D), trichothecenes, fumifungins, and the like. Methods of quantitating mycotoxin levels are widely documented. Moreover, commercial kits for measurement of the mycotoxins such as aflatoxin, fumonisin, deoxynivalenol, and zearalenone are also available (VICAM, Watertown, Mass., USA).

Compositions provided herein comprising *Methylobacterium* that inhibit plant pathogenic fungi are therefore expected to be useful in inhibiting fungal growth and/or infection in a wide variety of plant pathogenic fungi, including, but not limited to the anamorphic and/or teleomorphic stages of those phytopathogenic fungi in the following genera and species: *Blumeria* (*Blumeria graminis* f. sp. *tritici*), *Cercospora* (*Cercospora kikuchii*; *Cercospora sojina*; *Cercospora zeae-maydis*); *Cochliobolus* (*Colchliobolus maydis*; *Cochliobolus heterostrophus*; *Cochliobolus carbonum*); *Colletotrichum* (*Colletotrichum* lindemuthianum; *Colletotrichum* graminicola; *Colletotrichum cereale*); *Diplodia* (*Diplodia maydis*); *Exserohilum* (*Exserohilum turcicum*); *Fusarium* (*Fusarium nivale*; *Fusarium oxysporum*; *Fusarium graminearum*; *Fusarium culmorum*; *Fusarium solani*; *Fusarium moniliforme*; *Fusarium virguliforme*); *Macrophomina* (*Macrophomina phaseolina*); *Magnaporthe* (*Magnaporthe oryzae*; *Magnaporthe grisea*); *Phakopsora* (*Phakopsora pachyrhizi*); *Phialopora* (*Phialophora gregata*); *Phymatotrichum* (*Phymatotrichum omnivorum*); *Phytophthora* (*Phytophthora cinnamomi*; *Phytophthora cactorum*; *Phytophthora phaseoli*; *Phytophthora parasitica*; *Phytophthora citrophthora*; *Phytophthora megasperma* f. sp. *sojae*; *Phytophthora infestans*); *Puccinia* (*Puccinia sorghi*; *Puccinia striiformis*; *Puccinia graminis* fsp. *tritici*; *Puccinia asparagi*; *Puccinia recondita*; *Puccinia arachidis*; *Puccinia coronata*); *Pythium* (*Pythium aphanidermatum*; *Pythium ultimum*; *Pythium sylvaticum*; *Pythium torulosum*;

*Pythium lutarium; Pythium oopapillum*); *Pyrenophora* (*Pyrenophora tritici-repentis*); *Rhizoctonia* (*Rhizoctonia solani; Rhizoctonia cerealis*); *Sclerotium* (*Sclerotium rolfsii*); *Sclerotinia* (*Sclerotinia sclerotiorum; Sclerotinia homoeocarpa*); *Septoria* (*Septoria lycopersici; Septoria glycines; Septoria nodorum; Septoria tritici*); *Setosphaeria* (*Setosphaeria turcica*); *Stagonospora* (*Stagonospora nodorum*); *Verticillium* (*Verticillium dahliae; Verticillium alboatrum*). Compositions provided herein comprising *Methylobacterium* that inhibit plant pathogenic fungi are also expected to be useful in inhibiting fungal growth and/or infection by *Fusarium graminearum, Fusarium verticillioides, Fusarium virguliforme*, and/or *Fusarium proliferatum*. Compositions provided herein comprising *Methylobacterium* that inhibit fungal growth and/or infection by *Fusarium graminearum, Fusarium verticillioides, Fusarium virguliforme*, and/or *Fusarium proliferatum* can be used to control infections of cereal plants infected by these fungi. Infections of cereal plants selected from the group consisting of a rice, wheat, corn, barley, millet, sorghum, oat, and rye plants by *Fusarium* sp can be controlled by the compositions provided herein. In any of the aforementioned embodiments, the plant pathogenic fungus that is inhibited can be in its anamorphic form, its teleomorphic form, or in both its anamorphic and teleomorphic forms. Certain *Methylobacterium* isolates or combinations of isolates can also be used to inhibit certain plant pathogenic fungi in certain crops as disclosed in Table 3. In certain embodiments where a combination of isolates are used (e.g., NLS0109, a derivative thereof, or a *Methylobacterium* sp. related thereto and at least one additional *Methylobacterium* strain selected from the group consisting of NLS0017, NLS0020, NLS0021, NLS0042, NLS0064, NLS0066, NLS0089, a derivative thereof, and a *Methylobacterium* sp. related thereto), the isolates can be applied either simultaneously or sequentially. In certain embodiments where a combination of isolates are used (e.g., or NLS0109, a derivative thereof, or a *Methylobacterium* sp. related thereto and at least one additional *Methylobacterium* strain selected from the group consisting of NLS0017, NLS0020, NLS0021, NLS0042, NLS0064, NLS0066, NLS0089, a derivative thereof, and a *Methylobacterium* sp. related thereto), the isolates can be applied in either the same mode(s) (e.g., via a seed treatment, a foliar application, or in furrow) or by distinct modes.

TABLE 3

*Methylobacterium* isolates and combinations of isolates for use in compositions and methods for controlling certain plant pathogenic fungi in certain crops (including derivatives of the *Methylobacterium* isolates or *Methylobacterium* spp. related thereto)

| NLS Isolate(s) | Crop | Pathogen | Disease Common Name(s) | Mode(s) of Application |
|---|---|---|---|---|
| NLS0109 | Wheat | *Fusarium graminearum* | *Fusarium* head blight; seedling blight | Seed treatment; foliar; or both |
| | | *Pythium* spp | *Pythium* root rot | |
| | | *Septoria tritici*; *Stagonospora nodorum* | *Septoria*/*Stagonospora* blotch | |
| | | *Rhizoctonia solani* | *Rhizoctonia* root rot | |
| | | *Fusarium* spp. | *Fusarium* root, crown, and foot rot | |
| | | *Magnaporthe grisea* | Head blast | |
| | | *Pyrenophora tritici-repentis* | Tan Spot | |
| | | *Microdochium nivale* | Snow mold | |
| | | *Blumeria graminis* f. sp. *tritici* | Powdery mildew | |
| NLS0109 | Corn | *Cercospora zeae-maydis* | Gray leaf spot | Seed treatment; In-furrow; foliar; or both in-furrow and foliar |
| | | *Colletotrichum graminicola* | Anthracnose (foliar and stalk rot) | |
| | | *Fusarium graminearum* | *Fusarium* stalk rot; ear rot | |
| | | *Fusarium verticillioides* | *Fusarium* ear rot | |
| | | *Rhizoctonia solani* | *Rhizoctonia* crown and root rot | |
| | | *Stenocarpella maydis* | *Diplodia* stalk and ear rot | |
| | | *Pythium* spp. | *Pythium* root rot | |
| | | *Sclerospora graminicola*; *Sclerophthora macrospora* | Downy mildew; Crazy top | |
| NLS0109 | Soybean | *Cercospora sojina* | Frogeye leaf spot | Seed treatment; in-furrow; foliar; or any combination thereof |
| | | *Cercosporia kikuchii* | Purple leaf blotch and seed stain | |
| | | *Septoria glycines* | Brown spot | |
| | | *Pythium* spp. | *Pythium* root rot | |
| | | *Fusarium* spp. | *Fusarium* seed rot, blight/wilt, root rot, and pod and collar rot | |
| | | *Sclerotinia sclerotiorum* | White mold | |
| | | *Fusarium virguliform* | Sudden death syndrome | |
| | | *Rhizoctonia solani* | *Rhizoctonia* damping off and root rot | |

TABLE 3-continued

*Methylobacterium* isolates and combinations of isolates for use in compositions and methods for controlling certain plant pathogenic fungi in certain crops (including derivatives of the *Methylobacterium* isolates or *Methylobacterium* spp. related thereto)

| NLS Isolate(s) | Crop | Pathogen | Disease Common Name(s) | Mode(s) of Application |
|---|---|---|---|---|
| | | *Peronospora manshurica* | Downy mildew | |
| | | *Phytophthora sojae* | Root and stem rot | |
| NLS0109 + NLS0089 | Wheat | *Fusarium graminearum* | *Fusarium* head blight; seedling blight | Seed treatment; in-furrow; foliar; or any combination thereof where isolates are used alone or in combination for each treatment. |
| | | *Septoria tritici*; *Stagonospora nodorum* | *Septoria/Stagonospora* blotch | |
| | | *Pythium* spp. | *Pythium* root rot | |
| | | *Rhizoctonia solani* | *Rhizoctonia* root rot | |
| | | *Fusarium* spp. | *Fusarium* root, crown, and foot rot | |
| | | *Blumeria graminis* f. sp. *tritici* | Powdery mildew | |
| | | *Magnaporthe grisea* | Head blast | |
| | | *Pyrenophora tritici-repentis* | Tan Spot | |
| | | *Microdochium nivale* | Snow mold | |
| NLS0109 + NLS0089 | Soybean | *

TABLE 3-continued

*Methylobacterium* isolates and combinations of isolates for use in compositions and methods for controlling certain plant pathogenic fungi in certain crops (including derivatives of the *Methylobacterium* isolates or *Methylobacterium* spp. related thereto)

| NLS Isolate(s) | Crop | Pathogen | Disease Common Name(s) | Mode(s) of Application |
|---|---|---|---|---|
| | | *Peronospora manshurica* | Downy mildew | and NLS0109 applied foliar. |
| | | *Rhizoctonia solani* | *Rhizoctonia* damping off and root rot | |
| | | *Phytophthora sojae* | Root and stem rot | |
| | | *Fusarium virguliform* | Sudden death syndrome | |
| NLS0020 + NLS0109 | Corn | *Cercospora zeae-maydis* | Gray leaf spot | Seed treatment; in-furrow; foliar; or any combination thereof, where isolates are used alone or in combination for any treatment, including NLS0020 applied in-furrow and NLS0109 applied foliar. |
| | | *Colletotrichum graminicola* | Anthracnose (foliar and stalk rot) | |
| | | *Fusarium graminearum* | *Fusarium* stalk rot; ear rot | |
| | | *Fusarium verticillioides* | *Fusarium* ear rot | |
| | | *Rhizoctonia solani* | *Rhizoctonia* crown and root rot | |
| | | *Stenocarpella maydis* | *Diplodia* stalk and ear rot | |
| | | *Pythium* spp. | *Pythium* root rot | |
| | | *Sclerospora graminicola*; *Sclerophthora macrospora* | Downy mildew; Crazy top | |
| NLS0017 + NLS0109 | Corn | *Pythium* spp. | *Pythium* root and stalk rot | Seed treatment; in-furrow; foliar; or any combination thereof, where isolates are used alone or in combination for any treatment, including NLS0017 applied in-furrow and NLS0109 applied foliar. |
| | | *Rhizoctonia solani* | *Rhizoctonia* crown and root rot | |
| | | *Stenocarpella maydis* | *Diplodia* stalk and ear rot | |
| | | *Sclerospora graminicola*; *Sclerophthora macrospora* | Downy mildew; Crazy top | |
| | | *Fusarium* spp. | *Fusarium* root and stalk rot | |
| | | *Colletotrichum graminicola* | Anthracnose leaf blight and stalk rot | |
| | | *Cercospora zeae-maydis* | Gray leaf spot | |
| NLS0017 + NLS0109 | Soybean | *Sclerotinia sclerotiorum* | White mold | Seed treatment; in-furrow; foliar; or any combination thereof, where isolates are used alone or in combination for any treatment. |
| | | *Cercospora sojina* | Frogeye leaf spot | |
| | | *Cercospora kikuchii* | Purple leaf blotch and seed stain | |
| | | *Septoria glycines* | Brown spot | |
| | | *Pythium* spp. | *Pythium* root rot | |
| | | *Fusarium* spp. | *Fusarium* seed rot, blight/wilt, root rot, and pod and collar rot | |
| | | *Peronospora manshurica* | Downy mildew | |
| | | *Rhizoctonia solani* | *Rhizoctonia* damping off and root rot | |
| | | *Phytophthora sojae* | Root and stem rot | |
| | | *Fusarium virguliform* | Sudden death syndrome | |
| NLS0017 + NLS0109 | Wheat | *Fusarium graminearum* | *Fusarium* head blight; seedling blight | Seed treatment; foliar; or both |
| | | *Pythium* spp | *Pythium* root rot | |
| | | *Septoria tritici*; *Stagonospora nodorum* | *Septoria/Stagonospora* blotch | |
| | | *Rhizoctonia solani* | *Rhizoctonia* root rot | |
| | | *Fusarium* spp. | *Fusarium* root, crown, and foot rot | |
| | | *Magnaporthe grisea* | Head blast | |
| | | *Pyrenophora tritici-repentis* | Tan Spot | |
| | | *Microdochium nivale* | Snow mold | |
| | | *Blumeria graminis* f. sp. *tritici* | Powdery mildew | |
| NLS0064 + NLS0109 | Soybean | *Sclerotinia sclerotiorum* | White mold | Seed treatment; in-furrow; foliar; or any combination |
| | | *Cercospora sojina* | Frogeye leaf spot | |

TABLE 3-continued

Methylobacterium isolates and combinations of isolates for use in compositions and methods for controlling certain plant pathogenic fungi in certain crops (including derivatives of the Methylobacterium isolates or Methylobacterium spp. related thereto)

| NLS Isolate(s) | Crop | Pathogen | Disease Common Name(s) | Mode(s) of Application |
|---|---|---|---|---|
| | | Cercospora kikuchii | Purple leaf blotch and seed stain | thereof, where isolates are used alone or in combination for any treatment. |
| | | Septoria glycines | Brown spot | |
| | | Pythium spp. | Pythium root rot | |
| | | Fusarium spp. | Fusarium seed rot, blight/wilt, root rot, and pod and collar rot | |
| | | Peronospora manshurica | Downy mildew | |
| | | Rhizoctonia solani | Rhizoctonia damping off and root rot | |
| | | Phytophthora sojae | Root and stem rot | |
| | | Fusarium virguliform | Sudden death syndrome | |
| NLS0021 + NLS0109 | Corn | Pythium spp. | Pythium root and stalk rot | Seed treatment; in-furrow; foliar; or any combination thereof, where isolates are used alone or in combination for any treatment, including NLS0021 applied in-furrow and NLS0109 applied foliar. |
| | | Rhizoctonia solani | Rhizoctonia crown and root rot | |
| | | Stenocarpella maydis | Diplodia stalk and ear rot | |
| | | Sclerospora graminicola; Sclerophthora macrospora | Downy mildew; Crazy top | |
| | | Fusarium spp. | Fusarium root and stalk rot | |
| | | Colletotrichum graminicola | Anthracnose leaf blight and stalk rot | |
| | | Cercospora zeae-maydis | Gray leaf spot | |

In certain embodiments, an amount of a composition provided herein that is sufficient to provide for inhibition of fungal infection in a plant or plant part can be a composition with Methylobacterium that inhibit plant pathogenic fungi at a titer of at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an amount of a composition provided herein that is sufficient to provide for inhibition of fungal disease in a plant or plant part can be a composition with Methylobacterium that inhibit plant pathogenic fungi at a titer of about $5 \times 10^8$ colony-forming units per milliliter to at least about $6 \times 10^{10}$ colony-forming units per milliliter. In certain embodiments, an amount of a composition provided herein that is sufficient to provide for inhibition of fungal disease in a plant or plant part can be a fermentation broth product with a Methylobacterium that inhibit plant pathogenic fungi titer of a solid phase of that product is at least about $1 \times 10^7$, $5 \times 10^7$, $1 \times 10^8$, or $5 \times 10^8$ colony-forming units per gram to at least about $6 \times 10^{10}$, $1 \times 10^{13}$, or $5 \times 10^{13}$ colony-forming units of Methylobacterium per gram of the solid phase wherein a mono-culture or co-culture of Methylobacterium that inhibit plant pathogenic fungi is adhered thereto. In certain embodiments, an amount of a composition provided herein that is sufficient to provide for inhibition of fungal disease in a plant or plant part can be a composition with a Methylobacterium titer of at least about $1 \times 10^7$, $5 \times 10^7$, $1 \times 10^8$, or $5 \times 10^8$ colony-forming units per gram to at least about $6 \times 10^{10}$, $1 \times 10^{13}$, or $5 \times 10^{13}$ colony-forming units of Methylobacterium per gram of particles in the composition containing the particles that comprise a solid substance wherein a mono-culture or co-culture of Methylobacterium that inhibit plant pathogenic fungi is adhered thereto. In any of the aforementioned compositions, the indicated concentrations can be fungal inhibitory concentrations.

In certain embodiments, the compositions, plants and plant parts treated with the compositions, and methods provided herein can comprise fungicides in addition to the Methylobacterium strains for enhanced disease control. In certain embodiments, the fungicides are provided in compositions comprising the Methylobacterium, for example as seed treatments, as slurries for in furrow treatment or in foliar sprays. In certain embodiments, the fungicides are provided as separate compositions for use in the methods provided herein. Examples of fungicides that can be used in the compositions and methods provided herein for enhanced control of plant pathogenic fungi are provided in Table 4.

TABLE 4

| Crop | Pathogen | Disease Common Name(s) | Chemicals to Combine with Methylobacterium for Enhanced Disease Control |
|---|---|---|---|
| Wheat | Fusarium graminearum | Fusarium head blight; seedling blight | tebuconazole, triticonazole, metconazole, ipconazole, prothioconazole |

TABLE 4-continued

| Crop | Pathogen | Disease Common Name(s) | Chemicals to Combine with *Methylobacterium* for Enhanced Disease Control |
|---|---|---|---|
| Wheat | *Pythium* spp | *Pythium* root rot | metalaxyl, mefenoxam, oxathiapiprolin, ethaboxam, thiram, thiophanate-methyl |
| Wheat | *Blumeria graminis* f. sp. *tritici* | Powdery mildew | propiconazole, triadimenfon, fluxapyroxad, (trifloxystrobin, fluopyram specialty crops) |
| Wheat | *Septoria tritici*; *Stagonospora nodorum* | *Septoria*/*Stagonospora* blotch | tebuconazole, triticonazole, metconazole, ipconazole, prothioconazole |
| Wheat | *Rhizoctonia solani* | *Rhizoctonia* root rot | tebuconazole, triticonazole, metconazole, ipconazole, prothioconazole, thiram, captan, penflufen, carboxin, fluxapyroxad |
| Wheat | *Fusarium* spp. | *Fusarium* root, crown, and foot rot | tebuconazole, triticonazole, metconazole, ipconazole, prothioconazole, thiram, captan, penflufen, imazalil, carboxin, thiabendazole, fluxapyroxad |
| Wheat | *Magnaporthe grisea* | Head blast | prothioconazole, trifloxystrobin |
| Wheat | *Pyrenophora tritici-repentis* | Tan Spot | tebuconazole, triticonazole, metconazole, ipconazole, prothioconazole |
| Wheat | *Microdochium nivale* | Snow mold | dimethomorph, boscalid |
| Corn | *Cercospora zeae-maydis* | Gray leaf spot | azoxystrobin, pyraclostrobin, fluoxastrobin, and trifloxystrobin, fenamidone |
| Corn | *Colletotrichum graminicola* | Anthracnose (foliar and stalk rot) | ipconazole, prothioconazole, propiconazole, azoxystrobin, pyraclostrobin, fluoxastrobin, and trifloxystrobin |
| Corn | *Fusarium graminearum* | *Fusarium* stalk rot; ear rot | tebuconazole, triticonazole, metconazole, ipconazole, prothioconazole, thiram, captan, penflufen, imazalil, carboxin, thiabendazole, fluxapyroxad |
| Corn | *Fusarium verticillioides* | *Fusarium* ear rot | tebuconazole, triticonazole, metconazole, ipconazole, prothioconazole, thiram, captan, penflufen, imazalil, carboxin, thiabendazole, fluxapyroxad |
| Corn | *Fusarium* spp. | *Fusarium* root and stalk rot | tebuconazole, triticonazole, metconazole, ipconazole, prothioconazole, thiram, captan, penflufen, imazalil, carboxin, thiabendazole, fluxapyroxad |
| Corn | *Stenocarpella maydis* | *Diplodia* stalk and ear rot | tebuconazole, triticonazole, metconazole, ipconazole, prothioconazole, thiram, captan, penflufen, carboxin, fluxapyroxad |
| Corn | *Pythium* spp. | *Pythium* root and stalk rot | metalaxyl, mefenoxam, oxathiapiprolin, ethaboxam, thiram, thiophanate-methyl |
| Corn | *Sclerospora graminicola*; *Sclerophthora macrospora* | Downy mildew; Crazy top | propamocarb, dimethomorph, metalaxyl, mefenoxam |
| Corn | *Rhizoctonia solani* | *Rhizoctonia* crown and root rot | tebuconazole, triticonazole, metconazole, ipconazole, prothioconazole, thiram, captan, penflufen, carboxin, fluxapyroxad |
| Soybean | *Cercospora sojina* | Frogeye leaf spot | azoxystrobin, pyraclostrobin, fluoxastrobin, and trifloxystrobin |
| Soybean | *Cercosporia kikuchii* | Purple leaf blotch and seed stain | azoxystrobin, pyraclostrobin, fluoxastrobin, and trifloxystrobin, fenamidone |
| Soybean | *Septoria glycines* | Brown spot | azoxystrobin, pyraclostrobin, fluoxastrobin, and trifloxystrobin, fluopyram |
| Soybean | *Pythium* spp. | *Pythium* root rot | metalaxyl, mefenoxam, oxathiapiprolin, ethaboxam |
| Soybean | *Sclerotinia sclerotiorum* | White mold | tebuconazole, prothioconazole, fluopyram |

TABLE 4-continued

| Crop | Pathogen | Disease Common Name(s) | Chemicals to Combine with *Methylobacterium* for Enhanced Disease Control |
|---|---|---|---|
| Soybean | *Fusarium* spp. | *Fusarium* seed rot, blight/wilt, root rot, and pod and collar rot | tebuconazole, triticonazole, metconazole, ipconazole, prothioconazole, thiram, captan, penflufen, imazalil, carboxin, thiabendazole, fluxapyroxad |
| Soybean | *Fusarium virguliform* | Sudden death syndrome | fluopyram |
| Soybean | *Rhizoctonia solani* | *Rhizoctonia* damping off and root rot | tebuconazole, triticonazole, metconazole, ipconazole, prothioconazole, thiram, captan, penflufen, carboxin, fluxapyroxad |
| Soybean | *Phytophthora sojae* | Root and stem rot | metalaxyl, mefenoxam, oxathiapiprolin |

When chemicals are used in combination with *Methylobacterium*, application rates of the chemicals may be reduced compared to standard commercial application rates for a given plant species, while providing the same or increased level of protection to the plant from plant pathogenic fungal pathogens. In certain embodiments, *Methylobacterium* strains provided here provide enhanced activity in combination with fungicides as the result of activity against particular fungal strains for which the chemical fungicides provide no or incomplete control. In certain embodiments, the *Methylobacterium* is NLS0109 or NL0089, the fungus is *Cercospora*, the crop is corn, the disease is grey leaf spot, and the chemical is a strobilurin, such as pyraclostrobin, or an azole, such as tebuconazole. In certain embodiments, the fungicide application rate or numbers of applications of the fungicide can be reduced as the result of antifungal activity of the applied *Methylobacterium*. In certain embodiments, the *Methylobacterium* is NLS0109, the fungus is *Pythium*, the crop is soybean or corn, the disease is *Pythium* root rot, and the chemical is metalaxyl, mefenoxam, oxathiapiprolin or ethaboxam. In certain embodiments, the fungicide application rate or numbers of applications of the fungicide can be reduced as the result of antifungal activity of the applied *Methylobacterium*.

EXAMPLES

The following examples are included to demonstrate various embodiments. It will be appreciated by those of skill in the art that the techniques disclosed in the following examples represent techniques discovered by the Applicants to function well. However, those of skill in the art should, in light of the instant disclosure, appreciate that many changes can be made in the specific embodiments that are disclosed, while still obtaining like or similar results, without departing from the scope of the disclosure.

Example 1. Corn and Soybean Field Trials Summer of 2015

In the summer of 2015, field trials to evaluate disease suppression in corn and soybeans by PPFMs were performed at two independent locations: Bethel, Mo. and Troy, Ohio. Both trial locations were managed by contract research organizations. NewLeaf Symbiotics personnel visited each site at least twice to ensure proper trial implementation. The same strains and application rates were tested at both locations. The trials were arranged as a split-plot within an RCBD (randomized complete block design) with six replications at the Bethel site and four replications at the Troy site. Treatments for corn are described in Table 5 and treatments for soybean are described in Table 6. In-furrow treatments were applied at a rate of 1,250 mL 10×PPFM concentrate per acre and foliar treatments were applied at a rate of 5,000 mL 10×PPFM concentrate per acre. The split-plot design allowed for the evaluation of in-furrow treatment, foliar treatment, response to sequential PPFM treatments, and interactions between different PPFMs. Data from the Troy, Ohio soybean trial were not analyzed.

TABLE 5

2015 Pathology Corn Field Trial Treatments

| Treatment Number | Whole-plot treatment | Sub-plot treatment |
|---|---|---|
| 1 | Mock | Mock |
| 2 | NLS0020 | Mock |
| 3 | Mock | NLS0020 |
| 4 | NLS0020 | NLS0020 |
| 5 | Mock | NLS0109 |
| 6 | NLS0020 | NLS0109 |
| 7 | Mock | NLS0066 |
| 8 | NLS0020 | NLS0066 |

TABLE 6

2015 Pathology Soybean Field Trial Treatments

| Treatment Number | Whole-plot treatment | Sub-plot treatment |
|---|---|---|
| 1 | Mock | Mock |
| 2 | NLS0089 | Mock |
| 3 | Mock | NLS0020 |
| 4 | NLS0089 | NLS0020 |
| 5 | Mock | NLS0109 |
| 6 | NLS0089 | NLS0109 |
| 7 | Mock | NLS0066 |
| 8 | NLS0089 | NLS0066 |

At each site, conventional row spacing was used and standard agronomic practices were followed. Corn and soy hybrids with similar genetics but suitable for the specific trial locations were supplied for each site. Sub-plot sizes were no less than four 20' rows. A five-foot border was left between sub-plot to mitigate neighbor effects. Additionally, observations were taken from only the center two rows of each plot. Whole-plots consisted of the four sub-plots plus five foot borders between plots. Trial locations were selected in areas with natural disease pressure and no artificial inoculations were made. As a result, the same diseases were not evaluated at each location. Diseases rated in corn were anthracnose (*Colletotrichum graminicola*), grey leaf spot (*Cercospora zeae-maydis*), and common rust (*Puccinia sorghi*). Diseases rated in soybean were brown spot (*Septoria glycines*) and various foliar diseases, particularly frogeye leafspot (*Cercospora sojina*). For each disease present, incidence and/or severity ratings were collected and analyzed to determine treatment effects.

Disease ratings and statistical analysis results are reported in Tables 7-9. Due to the different disease ratings and replication number at each site, data from the two trial locations were analyzed separately. Data analyses were performed using SAS JMP software v11.2 (SAS Institute, Cary, N.C.). Data were analyzed according to JMP guidelines for split-plot analysis within the 'Fit Model' function, which uses the REML technique for mixed models. Student's T and Tukey's HSD post hoc tests were applied to determine differences between treatment groups ($\alpha$=0.05). Contrasts were used to make comparisons between specific groups of interest.

TABLE 7

Soybean Foliar Disease-Bethel, Missouri

| Whole-plot (in-furrow) Treatment | Sub-plot (foliar) Treatment | Brown spot severity early (%) | Brown spot severity late (%) | Leaf spot severity early (%) | Leaf spot severity late (%) |
|---|---|---|---|---|---|
| Mock | Mock | 3.00 | 8.33 | 1.67 | 5.50 |
| Mock | NLS0020 | $1.33^T$ | $4.17^{T,H}$ | $0.17^{T,H}$ | $2.00^{T,H}$ |
| Mock | NLS0066 | $1.67^T$ | $4.83^T$ | $0.67^T$ | 4.17 |
| Mock | NLS0109 | $1.67^T$ | $5.67^T$ | $0.50^{T,H}$ | $4.00^T$ |
| NLS0089 | Mock | $1.17^T$ | $5.00^T$ | $0.17^{T,H}$ | $2.50^{T,H}$ |
| NLS0089 | NLS0020 | $1.17^T$ | $5.17^T$ | $0.33^{T,H}$ | $2.50^{T,H}$ |
| NLS0089 | NLS0066 | 1.67 | $5.17^T$ | $0.33^{T,H}$ | 4.33 |
| NLS0089 | NLS0109 | 2.00 | $5.00^T$ | $0.33^{T,H}$ | $3.00^T$ |

$^T$Treatment significantly different from control (Mock, Mock) by Student's T-test ($\alpha$ = 0.05)
$^H$Treatment significantly different from control (Mock, Mock) by Tukey's HSD ($\alpha$ = 0.05)

TABLE 8

Corn Foliar Disease-Bethel, Missouri

| Whole-plot (in-furrow) Treatment | Sub-plot (foliar) Treatment | Anthracnose severity (%) | Gray leaf spot severity early (%) | Gray leaf spot severity late (%) | Common rust severity (%) |
|---|---|---|---|---|---|
| Mock | Mock | 21.17 | 3.17 | 13.00 | 12.17 |
| Mock | NLS0020 | 18.83 | $2.00^{T,H}$ | 11.33 | 11.67 |
| Mock | NLS0066 | $9.50^{T,H}$ | $1.83^{T,H}$ | $10.83^T$ | 10.50 |
| Mock | NLS0109 | $9.67^{T,H}$ | $2.50^T$ | $11.00^T$ | $10.00^T$ |
| NLS0020 | Mock | 18.67 | $2.17^T$ | 11.83 | 10.67 |
| NLS0020 | NLS0020 | 17.83 | $2.00^T$ | 11.50 | 11.33 |
| NLS0020 | NLS0066 | $9.17^T$ | $1.00^{T,H}$ | $9.50^{T,H}$ | $9.67^T$ |
| NLS0020 | NLS0109 | $9.17^T$ | $1.17^{T,H}$ | $9.83^{T,H}$ | $9.17^{T,H}$ |

$^T$Treatment significantly different from control by Student's T-test ($\alpha$ = 0.05)
$^H$Treatment significantly different from control by Tukey's HSD ($\alpha$ = 0.05)

TABLE 9

Corn Foliar Disease-Troy, Ohio

| Whole-plot (in-furrow) Treatment | Sub-plot (foliar) Treatment | Gray leaf spot severity (%) | Tip dieback severity (%) | Tip dieback incidence (%) | Stalk rot severity (%) |
|---|---|---|---|---|---|
| Mock | Mock | 67.50 | $11.00^1$ | $0.17^1$ | 1.55 |
| Mock | NLS0020 | 67.50 | 8.25 | 0.14 | 1.60 |
| Mock | NLS0066 | 62.50 | 12.50 | 0.18 | 1.45 |
| Mock | NLS0109 | 60.00 | 11.75 | 0.19 | 1.40 |
| NLS0020 | Mock | 65.00 | 7.50* | 0.12* | 1.85 |
| NLS0020 | NLS0020 | 67.50 | 10.00 | 0.16 | 1.55 |
| NLS0020 | NLS0066 | 60.00 | 9.00 | 0.14 | 1.45 |
| NLS0020 | NLS0109 | 62.50 | 9.25 | 0.14 | 1.85 |

[1]The average across all mock in-furrow treatments was significantly different from the average across all NLS0020 in-furrow treatments by contrast ($\alpha$ = 0.05)
*Treatment significantly different from control (Mock, Mock) by contrast ($\alpha$ = 0.10)

All treatments applied to soybeans demonstrated disease suppression against both brown spot (*Septoria glycines*) and other foliar leaf spot diseases. Foliar application of NLS0020 without in-furrow treatment resulted in the lowest rating for all diseases and was the most effective treatment for suppression of disease relative to the control. Foliar application of NLS0020 following NLS0089 in-furrow treatment also demonstrated disease suppression across all treatments. Foliar treatment of NLS0109 significantly reduced all diseases and provided greater suppression when applied after in-furrow treatment with NLS0089 for all applications except the early brown spot rating. In-furrow treatment with NLS0089 alone significantly reduced all diseases and had a particularly strong effect against foliar leaf spot diseases.

In corn at the Bethel, Mo. site, foliar applications of NLS0066 and NLS0109 significantly suppressed all diseases, with the exception of NLS0066 against common rust. In-furrow application of NLS0020 improved the disease suppression provided by NLS0066 and NLS0109 foliar applications in all examples. This demonstrates enhanced efficacy through multiple applications of these specific PPFM strains. Application of NLS0020 alone, including foliar, in-furrow, and in-furrow followed by foliar, resulted in reduction of early Gray leaf spot severity, but had no significant impact on the other diseases tested.

At the Troy, Ohio location, the NLS0066 and NLS0109 foliar applications provided the lowest gray leaf spot severity ratings. This was in agreement with the treatment effects observed in Missouri. In-furrow application of NLS0020 alone suppressed both the severity and incidence of tip dieback, which can be indicative of an effect on disease and abiotic stressors. Additionally, all applications of in-furrow NLS0020 combined suppressed tip dieback metrics relative to all mock in-furrow treatments combined, indicating an overall positive effect of NLS0020 in-furrow treatment.

Example 2. Suppression of White Mold by *Methylobacterium*

*Sclerotinia sclerotiorum* is a polyphagous ascomycete fungus, with a host range that encompasses thousands of dicot plants. White mold on soybean and other leguminous crops is of particular agronomic importance. Under cool, moist environmental conditions, white mold causes premature senescence and drastically reduced yields. There is no available complete genetic resistance to white mold and partial resistance is only marginally effective. Further, fungicide applications specifically for white mold are only applied in years when disease is highly likely and must be applied within a narrow window in order to provide effective protection. Application of beneficial bacteria that colonize the plant and provide enhanced disease resistance could mitigate effects of white mold and increase the efficacy of genetic and chemical disease management tactics.

Frozen PPFM stock solutions at a 10× concentration of approximately $1 \times 10^8$ CFU/mL were thawed to room temperature directly prior to foliar treatment. PPFM cells were washed by centrifuging to pellet the cells, pouring off the resulting supernatant, re-suspending the cells in one mL sterile distilled water, centrifuging and pouring off the supernatant a second time, then re-suspending a second time in 1 mL of sterile distilled water. Re-suspended, washed cells were then diluted to a 1× concentration. Within two hours of PPFM preparation, an airbrush calibrated to 20 psi was used to apply 10 mL of 1×PPFM solution evenly across each flat of treatment plants. PPFMs were applied to three-week old plants and inoculations were performed the following week when plants were approximately one-month old.

Seeds were planted into either potting media, field soil, or a 50/50 mix of potting media and field soil, depending on the specific experiment. In all experiments, flats holding 18 pots each were used and the pots containing individual treatments were organized into randomized complete blocks either at planting or just prior to inoculation. Immediately after planting, pots were moved to a greenhouse (75-80° F.; RH 40-90%; 16 h day-length) and grown there for one month. Plants were watered daily and received supplemental fertilizer two times per week.

One-month old plants were inoculated with 5-7 day-old cultures of *Sclerotinia sclerotiorum* grown on PDA in the dark. A modified version of the cut petiole inoculation technique was used (Hoffman et al. 2002. Plant Dis. 86:971-980). Briefly, the petiole of the third trifoliate was cut with scissors approximately one inch from the stem. The broad end of a 1000 uL pipet tip was used to excise an agar disk from the outer edge of an *S. sclerotiorum* culture. The tip was then placed over the cut petiole such that the broad end of the pipet tip was in contact with the stem and petiole base and the cut end of the petiole was in contact with the mycelium side of the agar plug. A small piece of parafilm was wrapped around the tip and stem to prevent the tip from falling off. Inoculated plants were incubated in the greenhouse for 7-10 days to allow for disease development prior to rating.

Lesion length and wilt severity were collected as disease metrics. Length of brown or bleached lesions was measured using a ruler. Wilt severity was rated on a 0-5 scale with 0 indicating a completely health plant and 5 indicating a dead plant.

A total of 12 different PPFM strains in five individual experiments, each replicated three times, were tested for suppression of white mold following foliar PPFM application (Table 10). Of these strains, only NLS0020 and NLS0109, both of which were in the first two experiments, had a significant effect on either lesion length or severity of wilt caused by pathogen infection (Table 11). In the first experiment, which had a lower sample size, no significant effects were detected but both NLS0020 and NLS0109 decreased white mold lesion length and wilt severity by at least 20% relative to the mock-treated control. In the second experiment, NLS0020 decreased lesion length by approximately 30% (P=0.04) but did not have a significant effect on wilt severity (10% reduction; P=0.76). NLS0109 decreased lesion length by approximately 40% (P<0.01) and wilt by approximately 40% (P=0.06). For analysis, a Dunnett's test was conducted in the 'Fit Y by X' function of SAS JMP v12.0 statistical analysis software. The mock-foliar treatment application group, which received a bacterial growth medium only foliar application, was designated as the control group.

TABLE 10

Lesion Length (LL) and Wilt Severity of White Mold Following Foliar Application of PPFM Strains

| Strain | LL ± SE | LL RTC (%) | Wilt ± SE | Wilt RTC (%) |
|---|---|---|---|---|
| Experiment 1 | | | | |
| Control | 100.42 ± 9.55 | 100.00 | 4.46 ± 0.26 | 100.00 |
| NLS0020 | 74.50 ± 10.65 | 74.19 | 3.33 ± 0.39 | 74.67 |
| NLS0071 | 84.79 ± 12.66 | 84.44 | 3.54 ± 0.41 | 79.37 |
| NLS0109 | 79.17 ± 09.90 | 78.84 | 3.58 ± 0.41 | 80.26 |
| Experiment 2 | | | | |
| Control | 106.04 ± 11.18 | 100.00 | 4.13 ± 0.34 | 100.00 |
| NLS0020 | 74.17 ± 8.67 | 69.94 | 3.71 ± 0.35 | 89.90 |
| NLS0071 | 94.38 ± 10.77 | 89.00 | 4.12 ± 0.32 | 101.01 |
| NLS0109 | 64.38 ± 10.81 | 60.71 | 2.92 ± 0.45 | 70.71 |
| Experiment 3 | | | | |
| Control | 45.00 ± 6.12 | 100.00 | 2.19 ± 0.33 | 100.00 |
| NLS0017 | 55.33 ± 7.12 | 123.00 | 2.83 ± 0.32 | 129.00 |
| NLS0037 | 50.63 ± 7.02 | 112.50 | 2.19 ± 0.38 | 100.00 |
| NLS0089 | 45.16 ± 6.52 | 100.35 | 1.94 ± 0.33 | 88.57 |
| Experiment 4 | | | | |
| Control | 63.75 ± 8.16 | 100.00 | 3.22 ± 0.33 | 100.00 |
| NLS0046 | 54.22 ± 9.33 | 85.05 | 2.34 ± 0.33 | 72.82 |
| NLS0064 | 67.81 ± 9.07 | 106.37 | 2.88 ± 0.34 | 89.32 |
| NLS0066 | 59.38 ± 9.03 | 93.13 | 2.56 ± 0.35 | 79.61 |
| Experiment 5 | | | | |
| Control | 79.38 ± 7.52 | 100.00 | 3.72 ± 0.30 | 100.00 |
| IP0021 | 97.26 ± 7.35 | 122.53 | 4.39 ± 0.21 | 117.97 |
| IP0121 | 95.78 ± 6.77 | 120.67 | 4.16 ± 0.17 | 111.76 |
| IP0237 | 84.38 ± 6.58 | 106.30 | 4.16 ± 0.24 | 111.76 |

TABLE 11

Analysis of White Mold Control by PPFM Strains

| Strain | LL (% control) | LL p-value | Wilt (% control) | Wilt p-value |
|---|---|---|---|---|
| NLS0071 | 11.00 | 0.6975 | −1.01 | 0.9996 |
| NLS0020 | 30.06 | 0.0429 | 10.10 | 0.7625 |
| NLS0109 | 39.29 | 0.0053 | 29.29 | 0.0589 |

Foliar applications of PPFM strain NLS0109 reduced symptoms of both lesion length and wilt on soybean caused by the white mold pathogen *Sclerotinia sclerotiorum*. Applications of this strain could be used as a standalone treatment for suppression of white mold. Further, NLS0109 could be mixed with chemical or biological disease management tools as part of an integrated disease management approach. Such combinations could be leveraged to increase and/or prolong product efficacy and as part of a resistance management program.

Example 3. Suppression of Gray Leaf Spot by *Methylobacterium* spp. in Combination and Comparison with Conventional Fungicides Gray leaf spot, caused by the ascomycete fungal pathogen *Cercospora zeae-maydis*, is a serious disease of field corn. While varying levels of resistance to this disease are present in commercial germplasm, no complete resistance is available. Gray leaf spot is a perennial problem and is particularly severe during summers with high relative humidity. The summer of 2016 was favorable for gray leaf spot, with disease pressure starting in June and persisting throughout the growing season.

In this trial, a greenhouse study was conducted to determine the efficacy of PPFM strains when applied alone, in combination with each other, or in combination with low label rates of the foliar fungicide Headline™ (active ingredient—pyraclostrobin; BASF Corporation, Research Triangle, NC, USA). These treatments were compared against Headline application alone, as well as other agriculturally relevant fungicide treatment and treatment combinations containing pyraclostrobin as an active ingredient (Table 12).

TABLE 12

PPFM/Industry Standard Greenhouse Trial Treatments

| No. | Treatment | Rate | Timing |
|---|---|---|---|
| 1 | Untreated control | 0 fl oz/A | N/A |
| 2 | Headline ™-Foliar | 6 fl oz/A | VT |
| 3 | Fortix ™ [1]-Foliar | 4 fl oz/A | VT |
| 4 | Xanthion ™ [2]-In-furrow | 0.6 fl oz/A Component A<br>3.0 fl oz/A Component B | Planting |
| 5 | Xanthion ™ In-furrow<br>Headline ™-Foliar | 0.6 fl oz/A Component A<br>3.0 fl oz/A Component B<br>6 fl oz/A | Planting<br><br>VT |
| 6 | NLS0020-In-furrow | 1,250 mL/A | Planting |
| 7 | NLS0020-In-furrow<br>Headline ™-Foliar | 1,250 mL/A<br>6 fl oz/A | Planting<br>VT |
| 8 | NLS0109-Foliar | 5,000 mL/A | VT |
| 9 | NLS0109-Foliar<br>Headline ™-Foliar | 5,000 mL/A<br>6 fl oz/A | VT<br>VT |
| 9 | NLS0020-In-furrow<br>NLS0109-Foliar | 1,250 mL/A<br>5,000 mL/A | Planting<br>VT |
| 10 | NLS0020-In-furrow<br>NLS0109-Foliar<br>Headline ™-Foliar | 1,250 mL/A<br>5,000 mL/A<br>6 fl oz/A | Planting<br>VT<br>VT |

[1] Fortix ™ (Arysta Life Sciences, Cary, North Carolina, USA)
[2] Xanthion ™ (BASF Corporation, Research Triangle, NC, USA)

The trial was conducted in Spring-Summer 2016 with corn planted in early April and inoculated two-weeks prior to anthesis. Inoculum was applied by placing pathogen-infected corn debris around the base of each plant and then increasing relative humidity within the greenhouse to 60-90% during the day and greater than 90% at night, with the temperature ranging from 70-82° F. To promote infection, a gray leaf spot susceptible corn hybrid (Sun Prairie 617RR) was used for the trial. Disease ratings were taken at 14, 21, and 28 days post-inoculation and a final ear weight was collected for each plant.

The trial was arranged as an RCBD with 10 replications. In-furrow treatments were applied at planting using a hand-held sprayer and application volumes were scaled down to the total pot area. Fungicides were mixed and applied in accordance with label instructions. PPFMs were supplied as frozen concentrate that was thawed just prior to application. Extra seeds were planted and treated for each treatment group to ensure a total of ten replicates were available for inoculation. Two weeks after germination, corn seedlings were transferred from seedlings trays to 2.5 gallon pots, in which they grown for the remainder of the experiment. Foliar applications were performed at the VT growth-stage using a backpack sprayer. To prevent drift within the greenhouse, plants in each treatment group were brought outside and the treatment was applied to the entire group. Plants were then returned to the greenhouse and randomized into the ten experimental replicates.

Disease data were analyzed in JMP version 12.0 (SAS Institute, Cary, N.C.). Disease incidence and severity values collected at each sampling data were used to calculate disease index [(incidence*severity)/100] and a cumulative area under the disease progress curve (AUDPC) was calculated the three disease index values for each treatment. Data were analyzed using the 'Fit Model' function in JMP with 'Rep' as a random effect and 'Treatment' as a fixed effect. A post-hoc Tukey test at an alpha level of 0.05 was applied to perform means separation between treatments (Table 13).

PPFM treatments alone did not perform differently from the UTC or from in-furrow treatment with Xanthion™. Xanthion™ is a combination product of pyraclostrobin and the *Bacillus subtilis* microbial inoculant strain MBI600; thus, PPFM strains alone performed similarly to a currently available commercial product that combines a chemical fungicide with a microbial agent. The combination of NL0020-IF/NL0109-F reduced disease relative to the UTC and disease levels under this treatment were not significantly different from those of either foliar-applied pyraclostrobin-based fungicide (Headline™ and Fortix™). NL0020-IF/Headline-F™ suppressed disease to levels similar to those of Xanthion-IF™/Headline-F™, Headline-F™, and Fortix-F™. As the Xanthion™/Headline™ combination requires two applications of pyraclostrobin, similar performance by NLS0020/Headline indicates that an application of this active ingredient could be dropped in favor of a PPFM application without any adverse effects on disease severity.

Figure 4:
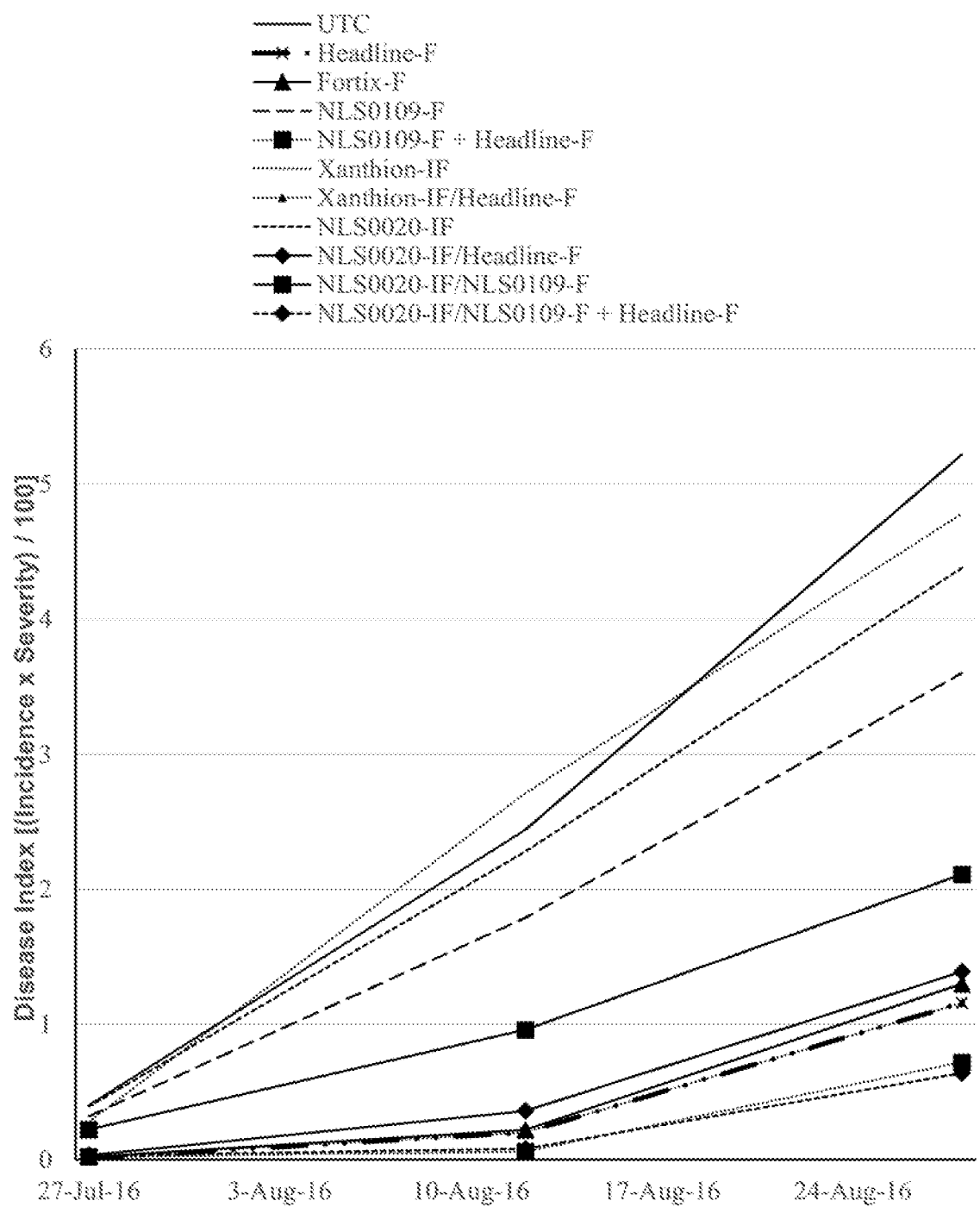
FIG. 4 is a line graph showing the progress of gray leaf spot disease severity over time in corn plants treated with PPFM strains, various commercial fungicides, and combinations thereof. Groups of ten plants were treated with various PPFM and fungicide treatments representing standard disease management practices or alternate PPFM treatment regimes alone or in combination with conventional chemistries. Disease incidence and severity data was collected at 14-, 21-, and 28-days post-inoculation and used to calculate disease index values [(incidence*severity)/100].

Of all treatments, NLS0109-F/Headline-F™ and NLS0020-IF/NLS0109-F+Headline-F™ had the greatest effects on disease suppression relative the UTC. In particular, these treatments numerically reduced disease to levels greater than Headline™ alone at the 21- and 14-day rating intervals (FIG. 4). This indicates the potential for PPFM applications, particularly NLS0109 foliar applications made in combination with Headline™, to extend the window of protection provided by conventional fungicides used for gray leaf spot mitigation.

In addition to disease suppression, PPFM application had a strong positive effect on ear weight (Table 12). The average weight for all treatments with PPFMs was 132.67 grams/ear, which is nearly ten grams higher than the 123.00 grams/ear average of the untreated control and fungicide-only treatments. Fortix™ alone was the only fungicide treatment to perform similarly to PPFM treatments and NLS0020 in-furrow application was particularly conducive to increased yield weight, garnering three of the four highest weights obtained.

This experiment demonstrates the potential for use of PPFMs in combination with conventional fungicides. PPFMs can be used to increase product efficacy by prolonging the window of effective protection offered by currently available chemistries and by offering an alternate product for use in resistance management. Additionally, PPFMs had a positive effect on ear weight, indicating a potential to boost yields when used alone or in combination with conventional fungicides.

TABLE 13

Gray Leaf Spot Greenhouse Evaluation Results

| Treatment | Yield (grams/ ear) | % Difference from UTC | AUDPC | % Difference from UTC | LSMeans Comparison (Tukey) |
|---|---|---|---|---|---|
| UTC | 120 | 0.00 | 39.55 | 0.00 | A |
| Headline-F ™ | 121 | 0.83 | 5.57 | −85.92 | BC |
| Fortix-F ™ | 135 | 12.50 | 6.3 | −84.07 | BC |

TABLE 13-continued

Gray Leaf Spot Greenhouse Evaluation Results

| Treatment | Yield (grams/ ear) | % Difference from UTC | AUDPC | % Difference from UTC | LSMeans Comparison (Tukey) |
|---|---|---|---|---|---|
| NLS0109-F | 127 | 5.83 | 28.49 | −27.96 | A |
| NLS0109-F + Headline-F ™ | 129 | 7.50 | 3.15 | −92.04 | C |
| Xanthion-IF ™ | 116 | −3.33 | 38.64 | −2.30 | A |
| Xanthion-IF ™/ Headline-F ™ | 123 | 2.50 | 5.67 | −85.66 | BC |
| NLS0020-IF | 135 | 12.50 | 35.39 | −10.52 | A |
| NLS0020-IF/ Headline-F ™ | 138 | 15.00 | 7.72 | −80.48 | BC |
| NLS0020-IF/ NLS0109-F | 131 | 9.17 | 16.44 | −58.43 | B |
| NLS0020-IF/ NLS0109-F + Headline-F ™ | 136 | 13.33 | 3.12 | −92.11 | C |

Example 4. Grey Leaf Spot Field Trials Summer 2016

A second year of corn pathology field trials was conducted in 2016. Trials were placed in sites with naturally high levels of gray leaf spot inoculum and a susceptible corn hybrid (Sun Prairie 617RR) was used to facilitate gray leaf spot infection. Two trial locations were included: Dana, Iowa and Bethel, Mo. At each site, the trial was conducted as a randomized complete block with six replicates. Standard local agronomic practices for fertilizer application, tillage, row spacing, population, and pest management were used. Standard weed and insect management practices were employed and seed was supplied to cooperators pre-treated with a standard fungicide/insecticide seed treatment package (Acceleron™ 2016 Corn, Monsanto, St. Louis, Mo., USA). Foliar fungicide applications were only made if specified in the trial protocol. Sixteen treatments were included in the trials, including PPFMs applied alone, PPFMs applied in combination, PPFMs applied alongside chemical fungicides, and fungicide alone standards (Table 14). PPFM compositions were diluted to a concentration of approximately $10^9$ CFU/ml and applied at the rates shown in Table 14. Assessments collected included early season stand and vigor, mid-season gray leaf spot incidence and severity, flowering date, stalk diameter, lodging, final stand at harvest, yield, and moisture content. Incidence and severity data from each rating date were combined to provide a disease index value [(incidence*severity)/100]. Data from each site were analyzed separately used JMP v12.0 (SAS Institute, Cary, N.C.). Treatment effects on response variables of interest were determined using the 'Fit Model' function with 'Treatment' specified as a fixed effect and 'Rep' as a random effect. Post-hoc means separation were performed using the lSMeans Differences Student's T option within 'Fit Model' and means are reported as LSMeans from the corresponding model. At the Bethel, Mo. site the Untreated check was the lowest yielding treatment and maintained the highest levels of gray leaf spot disease incidence and severity throughout the growing season (Table 15). Treatments with NLS0109 provided a greater than 10 bu/A yield increase over the Untreated check. Disease index values for both treatments with NLS0109 were significantly lower ($P<0.05$) than the Untreated check on the first two rating dates (August 12 and August 21) but on the final rating date (August 28) only the treatment combination of NLS0020 in-furrow followed by an NLS0109 foliar treatment suppressed disease relative to the Untreated check (Table 15).

TABLE 14

2016 Gray Leaf Spot Field Trial Treatments

| Trt No | Treatment(s) | Application Timing | Rate |
|---|---|---|---|
| 1 | Untreated Control | N/A | N/A |
| 2 | Headline ™ | VT[1] | 6.0 fl oz/A |
| 3 | Fortix ™ | VT | 4/0 fl oz/A |
| 4 | Xanthion ™ | In-furrow @ planting | 0.6 fl oz/A Component A 3.0 fl oz/A Component B |
|  | Headline ™ | VT | 6 fl oz/A |
| 5 | NLS0020 | In-furrow @ planting | 1.25 L/A |
| 6 | NLS0020 | In-furrow @ planting | 1.25 L/A |
|  | NLS0066 | VT | 5.0 L/A |
| 7 | NLS0020 | In-furrow @ planting | 1.25 L/A |
|  | NLS0089 | VT | 5.0 L/A |
| 8 | NLS0020 | In-furrow @ planting | 1.25 L/A |
|  | NLS0109 | VT | 5.0 L/A |
| 9 | NLS0020 | In-furrow @ planting | 1.25 L/A |
|  | Headline ™ | VT | 6 fl oz/A |
| 10 | NLS0020 | In-furrow @ planting | 1.25 L/A |
|  | Fortix ™ | VT | 4.0 fl oz/A |
| 11 | NLS0021 | In-furrow @ planting | 1.25 L/A |
| 12 | NLS0021 | In-furrow @ planting | 1.25 L/A |
|  | NLS0066 | VT | 5.0 L/A |
| 13 | NLS0021 | In-furrow @ planting | 1.25 L/A |
|  | NLS0089 | VT | 5.0 L/A |
| 14 | NLS0021 | In-furrow @ planting | 1.25 L/A |
|  | NLS0109 | VT | 5.0 L/A |
| 15 | NLS0021 | In-furrow @ planting | 1.25 L/A |
|  | Headline ™ | VT | 6.0 fl oz/A |
| 16 | NLS0021 | In-furrow @ planting | 1.25 L/A |
|  | Fortix | VT | 4.0 fl oz/A |

[1]VT stage of development: last branch of tassel completely visible but silks not visible.

TABLE 15

Summer 2016 Gray Leaf Spot Field Trial Results-Bethel, Missouri

| Treatment | Yield | Index_12 Aug. | Index_21 Aug. | Index_28 Aug. |
|---|---|---|---|---|
| Untreated Check | 141.77[1] C[2] | 7.25 A | 20.83 A | 24.83 A |
| NLS0020 | 149.93 BC | 4.85 B | 15.27 B | 21.33 AB |
| NLS0020/NLS0066 | 161.20 AB | 2.83 C | 12.28 BCD | 20.07 BC |
| NLS0020/NLS0089 | 159.88 AB | 2.08 CD | 12.37 BCD | 18.53 BC |
| NLS0020/NLS0109 | 155.15 ABC | 2.65 CD | 10.97 CD | 19.07 BC |
| NLS0020/Fortix ™ | 160.32 AB | 0.38 F | 1.78 E | 8.55 D |
| NLS0020/Headline ™ | 161.62 AB | 0.83 EF | 2.17 E | 5.88 D |
| NLS0021 | 157.32 AB | 4.00 B | 13.15 BC | 19.88 BC |
| NLS0021/NLS0066 | 159.47 AB | 1.57 DE | 8.87 D | 16.3 C |
| NLS0021/NLS0089 | 152.57 BC | 2.18 CD | 11.3 BCD | 20.58 ABC |
| NLS0021/NLS0109 | 153.40 ABC | 2.45 CD | 11.62 BCD | 20.88 AB |

TABLE 15-continued

Summer 2016 Gray Leaf Spot Field Trial Results-Bethel, Missouri

| Treatment | Yield | | Index_12 Aug. | | Index_21 Aug. | | Index_28 Aug. | |
|---|---|---|---|---|---|---|---|---|
| NLS0021/Fortix ™ | 164.22 | AB | 0.25 | F | 1.03 | E | 6.28 | D |
| NLS0021/Headline ™ | 167.23 | A | 0.23 | F | 1.57 | E | 4.83 | D |
| Fortix ™ | 161.62 | AB | 0.4 | F | 1.5 | E | 7.23 | D |
| Headline ™ | 163.78 | AB | 0.42 | F | 1.2 | E | 5.57 | D |
| Xanthion ™ | 167.27 | A | 0.17 | F | 0.9 | E | 5.52 | D |

[1]Values reported are means from six replicated plots per treatment
[2]Means followed by the same capital letter are not significantly different from one another by LSMeans Differences Student's T post-hoc means comparison test (alpha = 0.05)

Example 5 Detection of *Methylobacterium* Isolates on Target Crops

Assays are disclosed for detection of specific *Methylobacterium* strains and closely related derivatives on target crops.

A qPCR Locked Nucleic Acid (LNA) based assay for NLS109 is developed as follows. NLS109 genomic DNA sequence is compared by BLAST analysis of approximately 300 bp fragments using a sliding window of from 1-25 nucleotides to whole genome sequences of over 1000 public and proprietary *Methylobacterium* isolates. Genomic DNA fragments were identified that had weak BLAST alignments, indicative of approximately 60-95% identity over the entire fragment, to corresponding fragments from NLS0109. Target fragments from the NLS0109 genome corresponding to the identified weak alignments regions that were selected for assay development are provided as SEQ ID NOS:9-11

TABLE 16

Target Fragment Sequences of NLS0109

| Fragment | SEQ ID NO | Sequence |
|---|---|---|
| ref1_135566 | 9 | ACGGTCACCCCACGGACTGGGCGAGTACCTCACCGGTGTTC TATCATAACGCCGAGTTAGTTTTCGACCGTCCCTTATGCGA TGTACCACCGGTGTCGGCAGCCGATTTCGTCCCACCGGGAG CTGGCGTTCCGGTTCAGACCACCATCATCGGTCACGATGTC TGGATTGGACACGGGGCCTTCATCTCCCCCGGCGTGACTAT AGGAAACGGCGCGATCGTCGGGGCCCAGGCGGTCGTCACA AGAGATGTCCCACCCTATGCGGTAGTTGCTGGCGTCCCCGC GACCGTACGACGAT |
| ref1_135772 | 10 | CCAATAAAAGCGTTGGCCGCCTGGGCAACCCGATCCGAGC CTAAGACTCAAAGCGCAAGCGAACACTTGGTAGAGACAGC CCGCCGACTACGGCGTTCCAGCACTCTCCGGCTTTGATCGG ATAGGCATTGGTCAAGGTGCCGGTGGTGATGACCTCGCCC GCCGCAAGCGGCGAATTACTCGGATCAGCGGCCAGCACCT CGACCAAGTGTCGGAGCGCGACCAAAGGGCCACGTTCGAG GACGTTTGAGGCGCGACCAGTCTCGATAGTCTCATCGTCGC GGCGAAGCTGCACCTCGA |
| ref1_169470 | 11 | CGATGGCACCGACCTGCCATGCCTCTGCCGTCCGCGCCAGA ATGGTAAAGAGGACGAAGGGGGTAAGGATCGTCGCTGCAG TGTTGAGCAGCGACCAGAGAAGGGGGCCGAACATCGGCAT CAAACCTCGATTGCCACTCGGACGCGAAGCGCGTCTTGAA GGAGGGATGGAAGCGAAACGGCCGCAGAGTAACCGCCGA CGAAAGATTGCACCCCTCATCGAGCAGGATCGGAGGTGAA GGCAAGCGTGGGTTATTGGTAAGTGCAAAAAATATAATGG TAGCGTCAGATCTAGCGTTC |

Regions in SEQ ID NOS:9-11 where corresponding regions in other *Methylobacterium* strains were identified as having one or more nucleotide mismatches from the NLS109 sequence were selected, and qPCR primers designed using Primer3 software (Untergasser et al., 2012, Koressaar et al., 2007) to flank the mismatch regions, have a melting temperature (Tm) in the range of 53-58 degrees, and to generate a PCR DNA fragment of approximately 100 bp. The probe sequence was designed with a 5' FAM reporter dye, a 3' Iowa Black FQ quencher, and contains one to six LNA bases (Integrated DNA Technologies, Coralville, Iowa). At least 1 of the LNA bases is in the position of a mismatch, while the other LNA bases are used to raise the Tm. The Tm of the probe sequence is targeted to be 10 degrees above the Tm of the primers.

Primer and probe sequences for detection of specific detection of NLS0109 are provided as SEQ ID NOS: 12-20 in Table 17. Each of the probes contains a 5' FAM reporter dye and a 3' Iowa Black FQ quencher.

TABLE 17

Primer and Probe Sequences for Specific Detection of NLS0109

| Primer/Probe | SEQ ID NO | Sequence* |
|---|---|---|
| NLS0109_ref1_135566_forward | 12 | CCTCACCGGTGTTCTATCATAAC |
| NLS0109_ref1_135566_reverse | 13 | CCGATGATGGTGGTCTGAAC |
| NLS0109_ref1_135566_probe | 14 | CGTCCCTTATGCGATGTACCA |
| NLS0109_ref1_135772_forward | 15 | GATCCGAGCCTAAGACTCAAAG |
| NLS0109_ref1_135772_reverse | 16 | GACCAATGCCTATCCGATCAA |
| NLS0109_ref1_135772_probe | 17 | AACACTTGGTAGAGACAGCC |
| NLS0109_ref1_169470_forward | 18 | AAGGAGGGATGGAAGCGAAAC |
| NLS0109_ref1_169470_reverse | 19 | ATAACCCACGCTTGCCTTC |
| NLS0109_ref1_169470_probe | 20 | CGCAGAGTAACCGCCGACGAA |

*Bold and underlined letters represent the position of an LNA base

Use of Primer/Probe Sets on Isolated DNA to Detect NLS0109 and Distinguish from Related *Methylobacterium* Isolates A qPCR reaction is conducted in 20 ul and contains 10 ul of 2× KiCqStart™ Probe qPCR ReadyMix™, Low ROX™ from Sigma (Cat# KCQS05-1250RXN), 1 ul of 20× primer-probe mix (final concentration of primers is 0.5 uM each and final concentration of probe is 0.25 uM), and 9 ul of DNA template/water. Approximately 30-40 ng of DNA template is used per reaction. The reaction is conducted in a Stratagene Mx3005P qPCR machine with the following program: 95° C. for 3 min, then 40 cycles of 95° C. for 15 sec and 60° C. for 1 min. The MxPro software on the machine calculates a threshold and Ct value for each sample. Each sample was run in triplicate on the same qPCR plate. A positive result is indicated where the delta Ct between positive and negative controls is at least 5.

Use of the three primer/probe sets to distinguish NLS0109 from closely related isolates by analysis of isolated DNA is shown in Table 18 below. The similarity score shown for the related isolates takes into account both the average nucleotide identity and the alignment fraction between the isolates and NLS0109. One of the tested strains, NLS0730, was used as an additional positive control. It was isolated from a culture of NLS0109, was confirmed by full genome sequencing as identical to NLS0109, and scored positive in all three reactions. The similarity score of greater than 1.000 for this strain is likely the result of a slightly different assembly of the genome for this isolate compared to NLS0109. The delta Ct of approximately 15 or more between the NLS0109 and NLS0730 isolates and the water only control is consistent with the sequence confirmation of the identity of these isolates. Analysis of other isolates that are less closely related to NLS0109 results in delta Ct values similar to those for the water only control.

TABLE 18

| NLS# | Similarity score to NLS0109 | Average Ct Value |||
|---|---|---|---|---|
| | | Ref1_135566 | Ref1_135772 | Ref1_169470 |
| NLS0730 | 1.005 | 21.08 | 21.31 | 20.35 |
| NLS0109 | 1 | 21.97 | 22.62 | 22.08 |
| NLS0731 | 0.181 | No Ct | 37.85 | >37.91 |
| NLS0644 | 0.87 | >36.8 | >38.31 | No Ct |
| NLS0700 | 0.88 | >38.36 | >38.36 | >38.44 |
| NLS0710 | 0.894 | No Ct | >37.47 | >38.13 |
| NLS0834 | 0.852 | 37.81 | No Ct | 37.97 |
| NLS0939 | 0.862 | 37.94 | 38.37 | >38.35 |
| NLS0947 | 0.807 | 38.44 | No Ct | No Ct |
| NLS1015 | 0.894 | 38.77 | No Ct | >37.91 |
| NLS1217 | 0.872 | 37.64 | 37.20 | 37.96 |
| H2O only | | >38.14 | >35.92 | >37.12 |

Use of Primer/Probes for Detection of NLS109 on Treated Plant Materials.

Detection of NLS0109 on Seed Washes from Treated Soybean Seeds.

NLS0109 can be detected and distinguished from other *Methylobacterium* isolates on treated soybean seeds as follows. Soybean seeds were treated with *Methylobacterium* isolates from 10× frozen glycerol stock to obtain a final concentration of $10^6$ CFU/seed. Becker Underwood Flo Rite 1706 polymer is used to improve adhesion. An uninoculated control containing polymer and water is used. DNA is isolated from the seeds as follows. Approximately 25 ml of treated seeds are submerged for 5 minutes in 20 ml 0.9% sterile saline. Tubes are vortexed for 15 minutes, then the seed wash is removed to a new tube. An additional 10 ml 0.9% sterile saline is added to the same seeds, vortexed briefly, and combined with the previous seed wash. The seed wash liquid is centrifuged. The loose pellet is saved and transferred to smaller tubes, while the supernatant is discarded. The sample is centrifuged again, and the final sample obtained as an approximately 100 ul loose pellet. The 100 ul pellet is used as the input for DNA extraction using MOBio UltraClean Microbial DNA Extraction kit Cat#12224-250. As shown in Table 19, NLS0109 and NLS0730, are detected in seed washes from treated soybean seeds using all 3 primer probe sets, as demonstrated by delta Ct of greater than 10 as compared to Ct values of negative controls.

TABLE 19

| Treatment | Similarity score to NLS0109 | Average Ct Value |||
|---|---|---|---|---|
| | | Ref1_135566 | Ref1_135772 | Ref1_169470 |
| NLS0109 | 1 | 18.07 | 17.49 | 17.95 |
| control (polymer only) | N/A | 34.80 | 33.72 | 33.59 |
| NLS0730 | 1.005 | 17.76 | 17.03 | 17.54 |
| NLS0731 | 0.181 | 33.67 | 32.70 | 32.43 |

Detection of NLS0109 on Leaves from Plants Grown from Treated Soybean Seeds.

Soybean seeds were treated with *Methylobacterium* isolates NLS0109, NS0730, and NLS0731 from 10× frozen glycerol stock to obtain a final concentration of $10^6$ CFU/seed. Becker Underwood Flo Rite 1706 polymer is used to improve adhesion. An uninoculated control contained polymer and water. Seeds were planted in field soil mix, placed in a growth chamber for approximately two weeks, and watered with unfertilized RO water every 1-2 days to keep soil moist. After 2 weeks of growth, true leaves from about 9 plants were harvested into sterile tubes. Each treatment had at least 2 reps in each experiment, and each experiment was grown at least 3 times.

DNA from bacteria on the harvested leaves is isolated as follows. Leaves are submerged for 5 minutes in buffer containing 20 mM Tris, 10 mM EDTA, and 0.024% Triton X-100. Tubes are vortexed for 10 minutes, and then sonicated in two 5 minute treatments (10 minutes total). Leaf tissue is removed, and the remaining liquid centrifuged. The loose pellet is saved and transferred to smaller tubes, while the supernatant is discarded. The sample is centrifuged again, and the final sample obtained as an approximately 100 ul loose pellet. The 100 ul pellet is used as the input for DNA extraction using MOBio UltraClean Microbial DNA Extraction kit Cat#12224-250. The average yield of DNA is 50-60 ng/ul in 30 ul. As shown in Table 20, NLS0109 and NLS0730, are detected on leaves harvested from plants grown from soybean seeds treated with the *Methylobacterium* strains using all 3 primer probe sets, as demonstrated by delta Ct values of around 5.

TABLE 20

Average of 3 experiments each with 3 biological replicates

| Treatment | Similarity score to NLS0109 | Average Ct Value |||
|---|---|---|---|---|
| | | Ref1_135566 | Ref1_135772 | Ref1_169470 |
| NLS0109 | 1.000 | 35.00 | 34.67 | 34.00 |
| control (polymer only) | N/A | 39.67 | 39.67 | 39.33 |
| NLS0730 | 1.005 | 35.00 | 35.00 | 34.00 |
| NLS0731 | 0.181 | 40.00 | 39.67 | 40.00 |

For Detection of NLS0109 Foliar Spray Treatment on Corn:

Untreated corn seeds were planted in field soil in the growth chamber, and watered with non-fertilized R.O. water. After plants germinated and grew for approximately 3 weeks, they were transferred to the greenhouse. At V5 stage, plants were divided into 3 groups for treatment: foliar spray of NLS0109, mock foliar spray, and untreated. Plants receiving the foliar spray of NLS0109 were treated with 10× glycerol stock at the rate of 71.4 ul per plant using Solo sprayers. This converts to the rate of 10 L/acre in the field. Mock treated plants were sprayed with 71.4 ul water/plant. Untreated plants received no foliar spray treatment. Leaves were harvested two weeks after foliar spray treatment into sterile tubes and DNA from bacteria on the harvested leaves is isolated as described above. Each experiment was grown at least 2 times. As shown in Table 21, NLS0109 is detected on leaves harvested from corn plants treated by a foliar spray application of the *Methylobacterium* strains using all 3 primer probe sets, as demonstrated by delta Ct values of approximately 10 between the sample and the negative controls.

TABLE 21

| | Average Ct Value | | |
|---|---|---|---|
| Treatment | Ref1_135566 | Ref1_135772 | Ref1_169470 |
| Control (no application) | 32.43 | 32.10 | 31.55 |
| Control (mock application) | 35.54 | 35.34 | 34.80 |
| NLS0109 (10 L/acre equivalent) | 23.36 | 22.88 | 22.66 |

The above results demonstrate the use of genome specific primers and probes to detect *Methylobacterium* strain NLS0109 on various plant tissues following treatment with the strains, and provide methods to distinguish NLS0109 from closely related isolates. Similar methods are developed for additional *Methylobacterium* strains, NLS0020, NLS0017 and NLS0089 using target sequence fragments and primer/probe pairs as shown in Tables 22-27 below.

TABLE 22

Target Fragment Sequences of NLS0020

| Fragment | SEQ ID NO | Sequence |
|---|---|---|
| ref3_25009 | 21 | GCCCTTCTGTCAGGCGATATTGTATAATGGCGTTGCCCCAA TAGAAGCAGCCATTCGTGCGAGGGCAGCAGCGACGCTAGG TCGAAAGAGCATCCTAATCTCGATCAAGATGCGACTGAGA TTTCTGATGAAAATATCTAGACACAAGCAAAGCTGGTGAA ATTACAACGATCATGGCGACAATTGCGGCCAATTCGGCCG GAACTTGAAGGAACATAAAAATGAATATTACAAATATACC GCAAAGCATGTAGAGTTGCTACACCAAGGGTCGGGACGTC CAAAAAAACTCACTGAGGA |
| ref3_25219 | 22 | GGAACATAAAAATGAATATTACAAATATACCGCAAAGCAT GTAGAGTTGCTACACCAAGGGTCGGGACGTCCAAAAAAAC TCACTGAGGAAGTCGACTGGAAGCACGAGGCGCCCCCCCC AGGAGCGGGGCGACCGGCAAGGGGGCCCGCAATTGTCGCC ATGATCGACCAGCTTAGGTAGGATCCTCTTTCGACCTAACG AATGGCTGCTTCTATTGGGGCAACGCCATTATACAATATCG CCTGACCATCTGGAACGCGGCCCGGTCCACCGGCAGGTTG GCGACGACAGCGTCGGAG |
| ref1_4361220 | 23 | CGGCGTCGACCAGCCGGGCGAACTGCTTGGGCATGCTCTCC CGCGACGCCGGCCACAGCCGCGTCCCCGTCCCTCCGCACA GGATCATCGGGTGGATTTGAAAGGCAAAACGGGACATCAG GATAGGCCGCTCAGGCGTTGGCGCTGAGGCGCTTGATGTC GGCGTCGACCATCTCGGTGATCAGCGCCTCGAGGCTGGTCT CGGCCTCCCAGCCGAAGGTCGCCTTGGCCTTGGCGGGGTTG CCCAGCAGCACCTCGACCTCTGCCGGCCGGAACAGCGCCG GGTCGACGATCAGGTGG |
| ref1_4602420 | 24 | CTGGACATGCGCCCACCCCGGCCAAGTCCGACCGCACCGG CAACCGCTCCTGTAGTCGTCGTCATCGTTCTCACCCCTGAG GCGGAGACCGTCCGCTAACGGGGTGTCTCAAGCAACCGTG GGGCGGAGGAACACGCACGTAGTCGCGTTTCAAGGTTCGC ACGAACGCCTCGGCCATGCCGTTGCTCTGCGGGCTCTCCAG CGGCGTCGTTTTTGGCACCAAACCAAGGTCGCGGGCGAAG CGGCGCGTGTCGCGGGGACTGTCAGGAATTTCGTGTGGGG GCGGCCATAGTGGATCCG |

TABLE 23

Primer and Probe Sequences for Specific Detection of NLS0020

| Primer/Probe | SEQ ID NO | Sequence* |
|---|---|---|
| NLS0020_ref3_25009_5' | 25 | CACAAGCAAAGCTGGTGA |
| NLS0020_ref3_25009_3' | 26 | AAGATATGCTTTGCGGGTA |
| NLS0020_ref3_25009_probe | 27 | CGATCATGGCGACAA**TTG |
| NLS0020_ref3_25219_5' | 28 | CAATATCGCCTGACAGAAGG |
| NLS0020_ref3_25219_3' | 29 | CACTTCAACAAAGGCGATCA |
| NLS0020_ref3_25219_probe | 30 | TTGGCGACGACAGC |
| NLS0020_ref1_4361220_5' | 31 | ACTGCTTGGGCATGCTCTC |
| NLS0020_ref1_4361220_3' | 32 | CCTATCCTGATGTCCCGTTT |
| NLS0020_ref1_4361220_probe | 33 | AGGATCATCGGGTGGATTTG |
| NLS0020_ref1_4602420_5' | 34 | AGGAACACGCACGTAGTC |
| NLS0020_ref1_4602420_3' | 35 | CCACACGAAATTCCTGAC |
| NLS0020_ref1_4602420_probe | 36 | TGGCACCAAACCAA |

*Bold and underlined letters represent the position of an LNA base

TABLE 24

Target Fragment Sequences of NLS0017

| Fragment | SEQ ID NO | Sequence |
|---|---|---|
| ref4_930 | 37 | GCAAAACGACCTAATAGTTCTACAGCGGCATGCGCCAAGTCAGCGCGGTGAACAGTATACCTGGGAGCAACTTGTCCTCCGAAACCCACATAAAACAAATTACTCCTGGCAGTGCCCAGTCCATCAAAATCGAATACAATATTTCTCGAGGAGGCATCTGTAATAGCCTGCCAAAGCAACAAAGCTATGGCGCCGTTATGACTTTCATTGCTTCTGGTAGACATAAAATAATATGCCGATTTGTGATCCCAAATGTAGAATATTGCCGCATCAATTGCGCCAAGTTTATTTCGGATCGAT |
| ref1_142021 | 38 | GGCGCCAACGGTATGATCGCATGATTTTCCTGCGGCATAGCTTGCGGGAATGGCGTATTTGGCGCTCTCCTCAGGAATTTCTAAGGGCATACGCAGGAACTCTACAGCACTTTTACTGGTATTTTGTAGTGACAGCGGAGGAGGCTGGTGCTCAAGGTAATCGTGATGAAGTGATCCGGGCCATTCGGGGCGCGTTTCTAGTCTTTCCAATCCGCGCCCTGTACCACGTATTACGCCGGACCGGTCTGCGCCGCGCCGCCCTCTTGACCGCCCTAAATGTCTAAGAGCGTCTAACAAAGC |
| ref1_142636 | 39 | GACGATATCGCTCATCTTCACTGCATTGAAGCTGGTGCCGTACTGCATAGGGATGAAAAAGTGATGCGGATAGACGGCTGACGGGAAAGCGCCTGGTCGATCGAAGACTTTGCTGACGAGGTTGTGGTAGCCCCGGATATAGGCATCGAAGGCCGGGACGTTGATCCCATCCTTTGCCTTATCTTGACTGGCGTCGTCGCGTGCCGTCAGAACGGGCACGTCGCAGGTCATCGAGGCCAGCACCTTGCGGAACCTGCGTTCCGCCGTTGGGATTATCGACGGCGAACGCGGTGGCCGC |

TABLE 25

Primer and Probe Sequences for Specific Detection of NLS0017

| Primer/Probe | SEQ ID NO | Sequence* |
|---|---|---|
| NLS0017_ref4_930_forward | 40 | GTCCTCCGAAACCCACATAAA |
| NLS0017_ref4_930_reverse | 41 | CTACCAGAAGCAATGAAAGTCAT |
| NLS0017_ref4_930_probe | 42 | TCTGTAATAGCCTGCCAAAGCA |
| NLS0017_ref1_142021_forward | 43 | GGCTGGTGCTCAAGGTAAT |
| NLS0017_ref1_142021_reverse | 44 | ACATTTAGGGCGGTCAAGAG |
| NLS0017_ref1_142021_probe | 45 | ATGAAGTGATCCGGGCCAT |
| NLS0017_ref1_142636_forward | 46 | CCGTACTGCATAGGGATGAAA |
| NLS0017_ref1_142636_reverse | 47 | TAAGGCAAAGGATGGGATCAA |
| NLS0017_ref1_142636_probe | 48 | TTGCTGACGAGGTTGTGGTAG |

*Bold and underlined letters represent the position of an LNA base

TABLE 26

Target Fragment Sequences of NLS0089

| Fragment | SEQ ID NO | Sequence |
|---|---|---|
| ref1_194299 | 49 | GGAAATCGGCTTCAAGTACGACGTCACGCCGGCCATGCAGGTCACGGGTGCACTGTTCAATCTCGAGCGCGACAACCAGCCGTTCCCCTCGAACGTGGAGTCCGGCCTCGTCCTTGGCGCAGGTCAGACACGCACCCAGGGCGCGGAAATCGGCCTGGCCGGCTATCTAACCGATTGGTGGCAGGTCTTTGGCGGCTACGCTTATACCGAGGCACGCGTACTCTCGCCACTGGAAGACGATGGAGACGTGATCGCAGCAGGTAATCTCGTCGGCAACGTTCCGCTAAATACTTTCAGTCT |
| ref1_194305 | 50 | CGGCCTGGCCGGCTATCTAACCGATTGGTGGCAGGTCTTTGGCGGCTACGCTTATACCGAGGCACGCGTACTCTCGCCACTGGAAGACGATGGAGACGTGATCGCAGCAGGTAATCTCGTCGCAACGTTCCGCTAAATACTTTCAGTCTGTTCAACAAGTTCGATATCAACGAGAATTTCTCCGTTGCTCTGGGCTATTACTATCAGGATGCCAGCTTTGCCTCCTCAGACAATGCAGTGCGTTTGCCAAGTTATTCGCGGTTCGATGGCGGGTTGTTCTATCGATTCGACGAGTTGAC |
| ref1_194310 | 51 | ACGTTCCGCTAAATACTTTCAGTCTGTTCAACAAGTTCGATATCAACGAGAATTTCTCCGTTGCTCTGGGCTATTACTATCAGGATGCCAGCTTTGCCTCCTCAGACAATGCAGTGCGTTTGCCAAGTTATTCGCGGTTCGATGCGGGTTGTTCTATCGATTCGACGAGTTGACACGCGTTCAGCTTAGCGTCGAGAACATTTTCGACAGGCGTTACATCATCAACTCCAACAACAACAACAACCTCACGCCTGGCGCGCCGAGAACAGTCCGCGTGCAATTGATCGCTCGGTTCTAAA |

TABLE 27

Primer and Probe Sequences for Specific Detection of NLS0089

| Primer/Probe | SEQ ID NO | Sequence* |
|---|---|---|
| NLS0089_ref1_194299_forward | 52 | TTTGGCGGCTACGCTTATAC |
| NLS0089_ref1_194299_reverse | 53 | AACGTTGCCGACGAGATTAC |
| NLS0089_ref1_194299_probe | 54 | AGACGATGGAGACGTGATCGCA |
| NLS0089_ref1_194305_forward | 55 | GGCAACGTTCCGCTAAATAC |
| NLS0089_ref1_194305_reverse | 56 | AAAGCTGGCATCCTGATAGT |
| NLS0089_ref1_194305_probe | 57 | CGAGAATTTCTCCGTTGCTCTG |
| NLS0089_ref1_194310_forward | 58 | CGATGGCGGGTTGTTCTAT |
| NLS0089_ref1_194310_reverse | 59 | AGGCGTGAGGTTGTTGTT |
| NLS0089_ref1_194310_probe | 60 | AGGCGTTACATCATCAACTCCA |

*Bold and underlined letters represent the position of an LNA base

Example 6 Grey Leaf Spot Field Trials Summer 2017

The effect of *Methylobacterium* treatment on grey leaf spot disease of corn was evaluated in corn field trials. The trials were conducted as a randomized complete block with six replicates. Standard local agronomic practices for fertilizer application, tillage, row spacing, population, and pest management were used. Standard weed and insect management practices were employed and seed was supplied to cooperators pre-treated with a standard fungicide/insecticide seed treatment package (Acceleron™ 2016 Corn, Monsanto, St. Louis, Mo., USA). Foliar fungicide applications were only made if specified in the trial protocol and shown in the tables below. When seed was pretreated with *Methylobacterium*, it was provided from a composition comprising from $10^9$-$10^{10}$ CFU/ml to provided approximately $10^6$ CFU/seed. For in furrow or foliar applications, PPFM compositions were diluted to a concentration of approximately $10^9$ CFU/ml and applied at the rates shown in the tables below.

In one trial, treatments with NLS0109 in combination with NLS0017 or NLS0020 were evaluated. *Methylobacterium* strains were applied either as seed treatment or in furrow applications. Disease severity and yield results are provided in Table 28 below. Treatment with NLS0109/NLS0017 in furrow provided a 15 bu/acre yield increase over the untreated check. Treatment with NLS0109/NLS0020 as a seed treatment provided a greater than 10 bu/acre yield increase over the untreated check. Each of these treatments resulted in a yield that was approximately the same (or slightly increased) as for corn treated with Fortix (strobilurin plus triazole).

TABLE 28

Reduction of Grey Leaf Spot Disease with Combinations of PPFM Strains

| GSF-04 2017 | Application | Yield (bu/A) | GLS Severity |
|---|---|---|---|
| UNT | | 221 | 6.3 |
| NLS 17/109 0.625 liter/A | In furrow | 236 | 7.9 |
| NLS 20/109 0.625 liter/A | In furrow | 222 | 7 |
| NLS 17/109 | Seed treatment | 222 | 7.9 |
| NLS 20/109 | Seed treatment | 232 | 7.6 |
| Fortix 4.5 fl oz/A | In furrow | 228 | 5.9 |
| Monsoon 4.5 fl oz/A | Foliar @ VT | 237 | 6.7 |
| Headline 10 fl. Oz/A | Foliar @ VT | 254 | 4.9 |
| Average | | 231 | 6.775 |

In a second trial, NLS0089 and NLS0109 were applied at different application rates alone or in combination with commercial fungicides also applied at various rates. All applications were by foliar spray at the VT stage of development. Disease severity and yield results are provided in Tables 29 and 30 below.

TABLE 29

NLS 89 and 109 Applied in Combination With Headline (Pyraclostrobin)

| | Application Rate | bu/A | GLS Severity |
|---|---|---|---|
| UNT | | 241 | 42.3 |
| Headline 0.5 | 4 oz/A | 253 | 17.7 |
| Headline 1.0 | 8 oz/A | 257 | 19.4 |
| NLS 89 1.0 | 2.5 Liters/A | 232 | 32.9 |
| Headline 0.5/NLS 89 1.0 | 4 oz/A 2.5 Liters/A | 248 | 20.2 |
| Headline 1.0/NLS 89 1.0 | 8 oz/A 2.5 Liters/A | 249 | 21.1 |
| NLS 89 0.5 | 1.25 Liters/A | 238 | 41.9 |
| Headline 0.5/NLS 89 0.5 | 4 oz/A 1.25 Liters/A | 249 | 21.4 |

TABLE 29-continued

NLS 89 and 109 Applied in Combination With Headline (Pyraclostrobin)

| | Application Rate | bu/A | GLS Severity |
|---|---|---|---|
| Headline 1.0/NLS 89 0.5 | 8 oz/A 1.25 Liters/A | 258 | 18.9 |
| NLS 109 1.0 | 2.5 Liters/A | 241 | 40.6 |
| Headline 0.5/NLS 109 1.0 | 4 oz/A 2.5 Liters/A | 254 | 20.8 |
| Headline 1.0/NLS 109 1.0 | 8 oz/A 2.5 Liters/A | 258 | 18.4 |
| NLS 109 0.5 | 1.25 Liters/A | 229 | 43.4 |
| Headline 0.5/NLS 109 0.5 | 4 oz/A 1.25 Liters/A | 254 | 23.8 |
| Headline 1.0/NLS 109 0.5 | 8 oz/A 1.25 Liters/A | 243 | 17.1 |

TABLE 30

NLS 89 and 109 Applied in Combination With Monsoon (Tebuconazole)

| | | bu/A | GLS Severity % |
|---|---|---|---|
| UNT | | 231 | 49.9 |
| Monsoon 0.5 | 2 oz/A | 231 | 43.0 |
| Monsoon 1.0 | 4 oz/A | 237 | 43.2 |
| NLS 89 1.0 | 2.5 Liters/A | 231 | 41.3 |
| Mon 0.5/89 1.0 | 2 oz/A 2.5 Liters/A | 236 | 37.8 |
| Mon 1.0/89 1.0 | 4 oz/A 2.5 Liters/A | 239 | 40.8 |
| NLS 89 0.5 | 1.25 Liters/A | 234 | 47.6 |
| Mon 0.5/89 0.5 | 2 oz/A 1.25 Liters/A | 232 | 45.2 |
| Mon 1.0/89 0.5 | 4 oz/A 1.25 Liters/A | 234 | 34.2 |
| NLS 109 1.0 | 2.5 Liters/A | 238 | 41.1 |
| Mon 0.5/109 1.0 | 2 oz/A 2.5 Liters/A | 232 | 41.3 |
| Mon 1.0/109 1.0 | 4 oz/A 2.5 Liters/A | 233 | 40.5 |
| NLS 109 0.5 | 1.25 Liters/A | 234 | 42.7 |
| Mon 0.5/109 0.5 | 2 oz/A 1.25 Liters/A | 228 | 41.5 |
| Mon 1.0/109 0.5 | 4 oz/A 1.25 Liters/A | 237 | 42.9 |

Example 7 Greenhouse Assay to Determine Activity of *Methylobacterium* Strains Against *Pythium* Species A greenhouse experiment was conducted is to evaluate the ability of *Methylobacterium* strains to suppress *Pythium* disease in soybean. *Methylobacterium* treatments were compared to treatments with metalaxyl at various rates to determine if *Methylobacterium* strains can provide protection beyond and in addition to the level of protection provided by commonly used agronomic seed treatments. The experiment was designed to allow for growth of plants for in the presence of moderate levels of *Pythium*. spp. to determine impacts on emergence, % dead seed and root rot incidence and severity.

*Pythium* inoculants were prepared by mixing 453 g of parboiled rice and 323 mL of distilled water, placing the rice in a vented autoclavable plastic bag, and autoclaving 2×40 minutes with each cycle separated by 24 hours. Rice was inoculated with 3-4-day-old *Pythium* cultures and incubated for 7-10 days at 230 C in the dark. The inoculum was then dried for 2 days.

A 20 ml layer of rice inoculum is placed on soil in cups and additional soil layered on top of the inoculum to position the inoculum approximately 2-3 cm below the seeds to be planted. Water is added to the soil and 10 seeds are planted in each cup. Domes are placed over the cups and the cups are placed in growth chambers with temperature set at 230 C, and on a diurnal cycle of 16 h light and 8 h dark. The seeds are incubated for 14 days at 230 C. For experiments to assess activity of *Methylobacterium* strains against a consortium of 4 *Pythium* species, the seeds are incubated for 14 days at 130 C and for an additional 7 days at 230 C.

Plants are rated when the first trifoliate is fully emerged and open to determine total plant weight, number of seedlings and number of dead seeds. Disease incidence is evaluated as percent plants with rotted roots and disease severity as percent rotted root tissue for each seedling. Results of the analysis are provided in Tables 31-36 below.

Results from inoculation with *Pythium sylvaticum* at 230 C are shown in Tables 31-32 below.

TABLE 31

| Treatment | Emergence | % Dead Seed |
| --- | --- | --- |
| UTC | 65 | 35 |
| 0.35 Fl. oz/cwt metalaxyl | 82 | 18 |
| NLS0089 | 88 | 12 |
| NLS0109 | 87 | 13 |

NLS0109 and NLS0089 improved emergence and reduced % dead seed better than 7 gm/100 kg metalaxyl active ingredient

TABLE 32

| Treatment | Mean Emergence (%) | Mean Root Rot Severity (%) |
| --- | --- | --- |
| UTC | 60 | 11 |
| 1.25 Fl. oz/cwt metalaxyl | 78 | 21 |
| 0.75 Fl. oz/cwt metalaxyl | 92 | 18 |
| 0.35 Fl. oz/cwt metalaxyl | 78 | 17 |
| *Bacillus subtilis* | 83 | 6 |
| NLS0109 | 85 | 5 |

NLS0109 improved emergence and reduced root rot severity better than 7, 15 or 25 gm/100 kg metalaxyl active ingredient Results from inoculation with *Pythium lutarium* at 230 C are shown in Tables 33-34 below.

TABLE 33

| Treatment | Mean Emergence (%) | % Dead Seed |
| --- | --- | --- |
| UTC | 83 | 17 |
| 1.25 Fl. oz/cwt metalaxyl | 93 | 67 |
| 0.75 Fl. oz/cwt metalaxyl | 97 | 3 |
| NLS0109 | 97 | 3 |

NLS0109 improved emergence and reduced percent dead seed better than 25 gm/100 kg metalaxyl active ingredient and performed as well as 15 gm/100 kg metalaxyl active ingredient

TABLE 34

| Treatment | Mean Root Rot Incidence (%) | Mean Root Rot Severity (%) |
| --- | --- | --- |
| 1.25 Fl. oz/cwt metalaxyl | 93 | 11 |
| 0.75 Fl. oz/cwt metalaxyl | 95 | 10 |
| 0.35 Fl. oz/cwt metalaxyl | 95 | 13 |
| *Bacillus subtilis* | 93 | 13 |
| NLS0109 | 92 | 9 |

NLS0109 improved emergence and reduced root rot severity better than 7, 15 or 25 gm/100 kg metalaxyl active ingredient Results from inoculation with a consortium of 4 *Pythium* species at alternating temperature of 130 C and 230 C are shown in Tables 35-36 below. The four species, which are all important pathogens of corn and soybean, are *P. torulosum, P. oopapillum, P. sylvaticum* and *P. lutarium*.

TABLE 35

| Treatment | Mean Emergence (%) | Mean Dead Seed (%) |
| --- | --- | --- |
| UTC | 75 | 25 |
| 0.35 Fl. oz/cwt metalaxyl | 94 | 6 |
| NLS0089 | 100 | 2 |
| NLS0109 | 94 | 2 |
| 1.25 Fl. oz/cwt metalaxyl | 94 | 2 |
| 0.75 Fl. oz/cwt metalaxyl | 100 | 2 |

NLS0109 and NLS0089 improved emergence and NLS0089 reduced % dead seed better than 7 gm/100 kg metalaxyl active ingredient.

TABLE 36

| Treatment | Root Rot INC (%) | Root Rot Severity (%) |
| --- | --- | --- |
| UTC | 71 | 12 |
| 1.25 Fl. oz/cwt metalaxyl | 94 | 9 |
| 0.75 Fl. oz/cwt metalaxyl | 100 | 12 |
| 0.35 Fl. oz/cwt metalaxyl | 94 | 13 |
| NLS0089 | 94 | 8 |
| NLS0109 | 90 | 7 |

NLS0109 and NLS0089 reduced the incidence and severity of root rot when applied to untreated seed better than 7, 15 or 25 gm/100 kg metalaxyl active ingredient Example 8 Analysis of Effect of *Methylobacterium* Strains on *Rhizoctonia* and *Fusarium* Soil Diseases The effect of *Methylobacterium* treatment on emergence was evaluated in soy and corn field trials. Improved emergence is evidence of activity of the *Methylobacterium* treatment against common *Fusarium* and *Rhizoctonia* soil pathogens. The trials were conducted as a randomized complete block with four replicates. Standard local agronomic practices for fertilizer application, tillage, row spacing, population, and pest management were used. Standard weed and insect management practices were employed and seed was supplied to cooperators pre-treated with a standard fungicide/insecticide seed treatment. Seed treatment compositions for soybean contained ipconazole, metalaxyl, imidacloprid and a seed coating in addition to the *Methylobacterium* strains. Seed treatment compositions for corn contained ipconazole, metalaxyl, trifloxystrobin and clothianidin. Stand counts were made at 21 days after first emergence or about 27 days after planting. Effect of *Methylobacterium* treatment on emergence in corn was evaluated with *Methylobacterium* provided as a seed treatment or by in furrow application. Results are shown in Tables 37-39 below.

TABLE 37

Soybean Emergence

| Treatment | Stand Count |
| --- | --- |
| NLS 20/109 | 118432 |
| NLS 109 | 118170 |
| Integral ™ (*B. subtilis*) | 114456 |
| PPST 2030 | 114431 |
| NLS 64/109 | 112965 |
| UNT | 110376 |
| NLS 17/109 | 109652 |
| NLS 20/109 | 105465 |

Seed treatment with NLS0109 improved soybean stand count in comparison to treatment with Integral™ (*B. subtilis*, BASF), PPST 2030 (Pioneer Premium Seed Treatment) and untreated control.

TABLE 38

Corn Emergence following *Methylobacterium* seed treatment

| Treatment | Stand Count |
| --- | --- |
| NLS 17/109 | 34272 |
| UNT | 34141 |
| NLS 20/109 | 32638 |

TABLE 39

Corn Emergence following *Methylobacterium* in furrow application

| Treatment | Stand Count |
| --- | --- |
| NLS 17/109 | 34445 |
| NLS 20/109 | 33302 |
| UNT | 33186 |

Seed treatment with NLS0109 in combination with NLS0017 improved corn emergence in comparison to untreated control.

REFERENCES

Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.

Broekaert W F, Terras F R, Cammue B P, Vanderleyden J (1990) An automated quantitative assay for fungal growth inhibition. FEMS Microbiology Letters 69: 55-60

Cappellini R A, Peterson J L (1965) Macroconidium formation in submerged cultures by a non-sporulating strain of *Gibberella zeae*. Mycologia 57: 962-966.

Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.

Cappellini R A, Peterson J L (1965) Macroconidium formation in submerged cultures by a non-sporulating strain of *Gibberella zeae*. Mycologia 57: 962-966

Corpe, W. A., and D. V. Basile. 1982. Methanol-utilizing bacteria associated with green plants. Devel. Industr. Microbiol. 23: 483-493.

Corpe, W. A., and S. Rheem. 1989. Ecology of the methylotrophic bacteria on living leaf surfaces. FEMS Microbiol. Ecol. 62: 243-250.

Correll J C, Klittich C J R, Leslie J F (1987) Nitrate nonutilizing mutants of *Fusarium graminearum* and their use in vegetative compatibility tests. Phytopathology 77: 1640-1646.

Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.

Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.

Holland, M. A. 1997. *Methylobacterium* and plants. Recent. Res. Devel. in Plant Physiol. 1: 207-213.

Holland, M. A., and J. C. Polacco. 1994. PPFMs and other covert contaminants: Is there more to plant physiology than just plant? Annu. Rev. Plant Physiol. Plant Mol. Biol. 45: 197-209.

Kutschera, U. 2007. Plant-associated methylobacteria as co-evolved phytosymbionts. A hypothesis. Plant Signal Behav. 2: 74-78.

Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.

Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.

Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar CO-47 (*Oryza sativa* L.) by *Methylobacterium* spp. Bot. Bull. Acad. Sin. 45: 315-324.

Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10):1645-54.

Ringler, G. A. 1995. Reaction of soybean to inoculation with *Fuusarium solani*. M S thesis. Univ. of Illinois, Urbana-Champaign.

Roy, K. W., J. C. Rupe, D. E. Hershman, and T. S. Abney. 19997. Sudden death syndrome of soybean, Plant Dis. 81:1100-1111.

Rupe, J. C, E. E. Gbur, and D. M. Marx. 1991. Cultivar responses to sudden death syndrome of soybean. Plant Dis. 75:47-50.

Spelbrink R G, Dilmac N, Allen A, Smith T J, Shah D M, et al. (2004) Differential antifungal and calcium channel-blocking activity among structurally related plant defensins. Plant Physiol 135: 2055-2067.

Stanier, R. Y., N. J. Palleroni, and M. Doudoroff. 1966. The aerobic pseudomonads: A taxonomic study. J. Gen. Microbiol. 43: 159-271.

Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220, Sy, A., A. C. J. Timmers, C. Knief, and J. A. Vorholt. 2005. Methylotrophic metabolism is advantageous for *Methylobacterium extorquens* during colonization of *Medicago truncatula* under competitive conditions. Appl. Environ. Microbiol. 71: 7245-7252.

Vogel, H. J., and D. M. Bonner. 1956. Acetylornithinase of *Escherichia coli*: Partial purification and some properties. J. Biol. Chem. 218: 97-106.

Vogel, H. J. 1956. A convenient growth medium for *Neurospora* (Medium N). Microbial Genet Bull 13: 42-43

Whittenbury, R., S. L. Davies, and J. F. Wilkinson. 1970. Enrichment, isolation and some properties of methane-utilizing bacteria. J. Gen. Microbiol. 61: 205-218.

Wrather, J. A. 2010. Soybean disease loss estimates for the United States 1996-2010. Missouri Agric. Res. Sta., Delta Research Center. At the http internet site "aes.missouri.edu/delta/research/soyloss.htm"

The inclusion of various references herein is not to be construed as any admission by the Applicant that the references constitute prior art. Applicants expressly reserve their right to challenge any allegations of unpatentability of inventions disclosed herein over the references included herein.

Having illustrated and described the principles of the present disclosure, it should be apparent to persons skilled in the art that the disclosure can be modified in arrangement and detail without departing from such principles.

Although the materials and methods of this disclosure have been described in terms of various embodiments and illustrative examples, it will be apparent to those of skill in the art that variations can be applied to the materials and methods described herein without departing from the concept, spirit and scope of the disclosure. All such similar substitutes and modifications apparent to those skilled in the art are deemed to be within the spirit, scope and concept of the disclosure as defined by the appended claims or otherwise disclosed herein.

What is claimed is:

1. A composition comprising:
   (i) a fermentation product comprising a *Methylobacterium* strain that inhibits growth of a plant pathogenic fungus, wherein said fermentation product is essentially free of contaminating microorganisms, and wherein the *Methylobacterium* strain is NLS0109 (NRRL B-67340) or a derivative thereof having a sequence of any one of SEQ ID NOS: 9-11; and
   (ii) at least one of an agriculturally acceptable excipient and/or an agriculturally acceptable adjuvant,
   wherein the agriculturally acceptable excipient comprises at least one component selected from the group consisting of woodflours, clays, activated carbon, diatomaceous earth, fine-grain inorganic solids, calcium carbonate, calcium bentonite, kaolin, china clay, talc, perlite, mica, vermiculite, silicas, quartz powder, montmorillonite, and mixtures thereof, and
   wherein the agriculturally acceptable adjuvant comprises at least one component selected from the group consisting polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses, ethylcelluloses, methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, polychloroprene, and syrups or mixtures thereof.

2. The composition of claim 1, wherein the composition comprises the agriculturally acceptable excipient selected from the group consisting of woodflours, clays, activated carbon, diatomaceous earth, fine-grain inorganic solids, calcium carbonate, calcium bentonite, kaolin, china clay, talc, perlite, mica, vermiculite, silicas, quartz powder, montmorillonite, and mixtures thereof.

3. A method for suppressing a disease caused by a plant pathogenic fungus that comprises applying a composition comprising *Methylobacterium* NLS0109 (NRRL B-67340) or a *Methylobacterium* strain derived therefrom or related thereto to a plant, a plant part, to soil where a plant is grown, or any combination thereof in an amount that provides for a decrease in adverse effects caused by growth of said plant pathogenic fungus in said plant, plant part, a plant obtained from said plant part, or a plant grown in said soil, relative to adverse effects of said plant pathogenic fungus in a control plant, plant part, or plant that had not received an application of said composition or been grown in soil treated with the composition, wherein said *Methylobacterium* strain derived from or related to NLS0109 has a sequence of any one of SEQ ID NOS: 9-11.

4. The method of claim 3, wherein application of said composition provides for at least a 40% inhibition of a plant pathogenic fungal infection in said plant, plant part, or a plant derived therefrom relative to infection of the control plant, plant part, or plant.

5. The method of claim 4, wherein said plant part is a seed.

6. The method of claim 3, wherein the plant or plant part is a cereal plant or plant part.

7. The method of claim 6, wherein the cereal plant or plant part is selected from the group consisting of a rice, wheat, corn, barley, millet, sorghum, oat, and rye plant or plant part.

8. The method of claim 3, wherein said plant pathogenic fungus is a *Blumeria* sp., a *Cercospora* sp., a *Cochliobolus* sp., a *Colletotrichum* sp., a *Diplodia* sp., an *Exserohilum* sp., a *Fusarium* sp., *Gaeumanomyces* sp., *Macrophomina* sp., a *Magnaporthe* sp., a *Microdochium* sp., a *Peronospora* sp., a *Phakopsora* sp., a *Phialophora* sp., a *Phoma* sp., a *Phymatotrichum* sp., a *Phytophthora* sp., a *Pyrenophora* sp., a *Pyricularia* sp, a *Pythium* sp., a *Rhizoctonia* sp., a *Sclerophthora*, a *Sclerospora* sp., a *Sclerotium* sp., a *Sclerotinia* sp., a *Septoria* sp., a *Stagonospora* sp., a *Stenocarpella* sp. or a *Verticillium* sp.

9. The method of claim 8, wherein said *Fusarium* sp. is *Fusarium graminearum*, *Fusarium verticillioides*, *Fusarium oxysporum*, or *Fusarium solani*; wherein said *Rhizoctonia* sp. is *Rhizoctonia solani* or *Rhizoctonia cerealis*; wherein said *Colletotrichum* sp. is *Colletotrichum graminicola*; wherein said *Cercospora* sp. is *Cercospora zeae-maydis*, *Cercospora sojina*, or *Cercospora kikuchii*; wherein said *Septoria* sp. is *Septoria glycines* or *Septoria tritici*; wherein said *Pythium* sp. is *Pythium sylvaticum*, *Pythium aphanidermatum*, *Pythium ultimum*, *Pythium torulosum*, *Pythium lutarium* or *Pythium oopapillum*; wherein said *Puccinia* sp. is *Puccinia sorghi*; or wherein said *Sclerotinia* sp. is *Sclerotinia sclerotiorum* or *Sclerotinia homoeocarpa*.

10. The method of claim 3, wherein the composition further comprises a second *Methylobacterium* strain selected from the group consisting of NLS0017 (NRRL B-50931), NLS0020 (NRRL B-50930), and *Methylobacterium* strains derived from or related to NLS0017 or NLS0020 and having a sequence of any one of SEQ ID NOS: 21-24 or 37-39.

11. The method of claim 3, wherein the composition further comprises a fungicide.

12. The method of claim 11 wherein said fungicide is selected from a group consisting of a strobilurin fungicide selected from azoxystrobin, pyraclostrobin, fluoxystrobin, and trifloxystrobin; a triazole, a phenylamide, thiazolecarboxamide, and piperidinyl thiazole isoxazoline fungicide.

13. The method of claim 11, wherein the fungicide is selected from a group consisting of metalaxyl, ipconazole, prothioconazole, mefenoxam, ethaboxam and oxathiapiprolin.

14. The method of claim 12, wherein the triazole fungicide is tebuconazole.

15. A plant, plant part or seed that is at least partially coated with a coating comprising a composition comprising (i) a fermentation product comprising *Methylobacterium* NLS0109 (NRRL B-67340) or a *Methylobacterium* strain derived therefrom or related thereto having a sequence of any one of SEQ ID NOS: 9-11, wherein said fermentation product is essentially free of contaminating microorganisms, and wherein said coating is not naturally occurring on said plant, plant part, or seed.

16. The plant, plant part or seed of claim 15, wherein said *Methylobacterium* NLS0109 or derivative thereof provides for inhibition of a plant pathogenic fungus infection of said coated plant or plant part, or a plant grown from said coated seed.

17. The plant, plant part, or seed of claim 16, wherein said plant pathogenic fungus is a *Fusarium* sp., a *Rhizoctonia* sp., a *Colletotrichum* sp., a *Cercospora* sp., a *Septoria* sp., a *Pythium* sp., a *Puccinia* sp. or a *Sclerotinia* sp.

18. The plant, plant part or seed of claim 16, wherein said composition further comprises an antifungal compound.

19. The plant, plant part, or seed of claim 15, wherein *Methylobacterium* NLS0109 is at a titer of at least about $5 \times 10^8$ colony-forming units per milliliter or at least about $5 \times 10^8$ colony-forming units per gram.

20. The plant, plant part, or seed of claim 15, wherein said composition further comprises a second *Methylobacterium* strain selected from the group consisting of NLS0017 (NRRL B-50931), NLS0020 (NRRL B-50930), and a *Methylobacterium* strain derived from or related to NLS0017 or NLS0020 having a sequence of any one of SEQ ID NOS: 21-24 or 37-39.

* * * * *

SEQUENCE LISTING

<160> NUMBER OF SEQ ID NOS: 60

<210> SEQ ID NO 1
<211> LENGTH: 1471
<212> TYPE: DNA
<213> ORGANISM: Methylobacterium sp.

<400> SEQUENCE: 1

```
ggtgatccag ccgcaggttc ccctacggct accttgttac gacttcaccc cagtcgctga      60
ccctaccgtg gtcgcctgcc tccttgcggt tggcgcagcg ccgtcgggta agaccaactc     120
ccatggtgtg acgggcggtg tgtacaaggc ccgggaacgt attcaccgtg gcatgctgat     180
ccacgattac tagcgattcc gccttcatgc actcgagttc cagagtgcaa tccgaactga     240
gacggctttt ggggatttgc tccagatcgc tccttcgcct cccactgtca ccgccattgt     300
agcacgtgtg tagcccatcc cgtaagggcc atgaggactt gacgtcatcc acaccttcct     360
cgcggcttat caccggcagt ctccctagag tgcccaactg aatgatggca actaaggacg     420
tgggttgcgc tcgttgcggg acttaaccca acatctcacg acacgagctg acgacagcca     480
tgcagcacct gtgtgcgcgc caccgaagtg gaccccaaat ctctctgggt aacacgccat     540
gtcaaaggat ggtaaggttc tgcgcgttgc ttcgaattaa accacatgct ccaccgcttg     600
tgcgggcccc cgtcaattcc tttgagtttt aatcttgcga ccgtactccc caggcggaat     660
gctcaaagcg ttagctgcgc tactgcggtg caagcacccc aacagctggc attcatcgtt     720
tacggcgtgg actaccaggg tatctaatcc tgtttgctcc ccacgctttc gcgcctcagc     780
gtcagtaatg gtccagttgg ccgccttcgc caccggtgtt cttgcgaata tctacgaatt     840
tcacctctac actcgcagtt ccaccaacct ctaccatact caagcgtccc agtatcgaag     900
gccattctgt ggttgagcca caggctttca cccccgactt aaaacgccgc ctacgcgccc     960
tttacgccca gtgattccga gcaacgctag ccccttcgt attaccgcgg ctgctggcac    1020
gaagttagcc ggggcttatt cctccggtac cgtcattatc gtcccggata aaagagcttt    1080
acaaccctaa ggccttcatc actcacgcgg catggctgga tcaggcttgc gcccattgtc    1140
caatattccc cactgctgcc tcccgtagga gtctgggccg tgtctcagtc ccagtgtggc    1200
tgatcatcct ctcagaccag ctactgatcg tcgccttggt aggccgttac cccaccaact    1260
```

| | |
|---|---:|
| agctaatcag acgcgggccg atcttccggc agtaaaccttt tccccaaaag gcgtatccg | 1320 |
| gtattagccc tagtttccca gggttattcc gaaccagaag gcacgttccc acgcgttact | 1380 |
| cacccgtccg ccgctgaccc cgaaaggccc gctcgacttg catgtgttaa gcctgccgcc | 1440 |
| agcgttcgct ctgagccagg atcaaactct c | 1471 |

<210> SEQ ID NO 2
<211> LENGTH: 1471
<212> TYPE: DNA
<213> ORGANISM: Methylobacterium sp.

<400> SEQUENCE: 2

| | |
|---|---:|
| ggtgatccag ccgcaggttc ccctacggct accttgttac gacttcaccc cagtcgctga | 60 |
| ccctaccgtg gtcgcctgcc tccttgcggt tggcgcagcg ccgtcgggta agaccaactc | 120 |
| ccatggtgtg acgggcggtg tgtacaaggc ccgggaacgt attcaccgtg gcatgctgat | 180 |
| ccacgattac tagcgattcc gccttcatgc actcgagttg cagagtgcaa tccgaactga | 240 |
| gacggctttt ggggatttgc tccagatcgc tccttcgcgt cccactgtca ccgccattgt | 300 |
| agcacgtgtg tagcccatcc cgtaagggcc atgaggactt gacgtcatcc acaccttcct | 360 |
| cgcggcttat caccggcagt ctccctagag tgcccaacta aatgatggca actaaggacg | 420 |
| tgggttgcgc tcgttgcggg acttaaccca acatctcacg acacgagctg acgacagcca | 480 |
| tgcagcacct gtgtgcgcgc caccgaagtg accccaaat ctctctgggt aacacgccat | 540 |
| gtcaaaggat ggtaaggttc tgcgcgttgc ttcgaattaa accacatgct ccaccgcttg | 600 |
| tgcgggcccc cgtcaattcc tttgagtttt aatcttgcga ccgtactccc caggcggaat | 660 |
| gctcaaagcg ttagctgcgc tactgcggtg caagcacccc aacagctggc attcatcgtt | 720 |
| tacggcgtgg actaccaggg tatctaatcc tgtttgctcc ccacgctttc gcgcctcagc | 780 |
| gtcagtaatg gtccagttgg ccgccttcgc caccggtgtt cttgcgaata tctacgaatt | 840 |
| tcacctctac actcgcagtt ccaccaacct ctaccatact caagcgtccc agtatcgaag | 900 |
| gccattctgt ggttgagcca caggctttca ccccgactt aaaacgccgc ctacgcgccc | 960 |
| tttacgccca gtgattccga gcaacgctag ccccccttcgt attaccgcgg ctgctggcac | 1020 |
| gaagttagcc ggggcttatt cctccggtac cgtcattatc gtcccggata aaagagcttt | 1080 |
| acaaccctaa ggccttcatc actcacgcgg catggctgga tcaggcttgc gcccattgtc | 1140 |
| caatattccc cactgctgcc tcccgtagga gtctgggccg tgtctcagtc ccagtgtggc | 1200 |
| tgatcatcct ctcagaccag ctactgatcg tcgccttggt aggccgttac cccaccaact | 1260 |
| agctaatcag acgcgggccg atcttccggc agtaaaccttt tccccaaaag gcgtatccg | 1320 |
| gtattagccc tagtttccca gggttattcc gaaccagaag gcacgttccc acgcgttact | 1380 |
| cacccgtccg ccgctgaccc cgaagggccc gctcgacttg catgtgttaa gcctgccgcc | 1440 |
| agcgttcgct ctgagccagg atcaaactct c | 1471 |

<210> SEQ ID NO 3
<211> LENGTH: 1472
<212> TYPE: DNA
<213> ORGANISM: Methylobacterium sp.

<400> SEQUENCE: 3

| | |
|---|---:|
| gagtttgatc ctggctcaga gcgaacgctg gcggcaggct taacacatgc aagtcgaacg | 60 |
| ggcttcttcg gaagtcagtg gcagacgggt gagtaacacg tggaacgtg cccttcggtt | 120 |
| cggaataact cagggaaact tgagctaata ccggatacgc ccttatgggg aaaggttac | 180 |

```
tgccgaagga tcggcccgcg tctgattagc ttgttggtgg ggtaacggcc taccaaggcg      240
acgatcagta gctggtctga gaggatgatc agccacactg ggactgagac acggcccaga      300
ctcctacggg aggcagcagt ggggaatatt ggacaatggg cgcaagcctg atccagccat      360
gccgcgtgag tgatgaaggc cttagggttg taaagctctt ttgtccggga cgataatgac      420
ggtaccggaa gaataagccc cggctaactt cgtgccagca gccgcggtaa tacgaagggg      480
gctagcgttg ctcggaatca ctgggcgtaa agggcgcgta ggcggccgat taagtcgggg      540
gtgaaagcct gtggctcaac cacagaattg ccttcgatac tggttggctt gagaccggaa      600
gaggacagcg gaactgcgag tgtagaggtg aaattcgtag atattcgcaa gaacaccagt      660
ggcgaaggcg gctgtctggt ccggttctga cgctgaggcg cgaaagcgtg gggagcaaac      720
aggattagat accctggtag tccacgccgt aaacgatgaa tgccagccgt tggtctgctt      780
gcaggtcagt ggcgccgcta acgcattaag cattccgcct ggggagtacg gtcgcaagat      840
taaaactcaa aggaattgac gggggcccgc acaagcggtg gagcatgtgg tttaattcga      900
agcaacgcgc agaaccttac catcccttga catggcatgt acctcgaga gatcggggat       960 cctcttcgga ggcgtgcaca caggtgctgc atggctgtcg tcagctcgtg tcgtgagatg     1020
ttgggttaag tcccgcaacg agcgcaaccc acgtccttag ttgccatcat tcagttgggc     1080
actctaggga gactgccggt gataagccgc gaggaaggtg tggatgacgt caagtcctca     1140
tggcccttac gggatgggct acacacgtgc tacaatggcg gtgacagtgg gacgcgaaac     1200
cgcgaggttg agcaaatccc caaaagccgt ctcagttcgg attgcactct gcaactcggg     1260
tgcatgaagg cggaatcgct agtaatcgtg gatcagcacg ccacggtgaa tacgttcccg     1320
ggccttgtac acaccgcccg tcacaccatg ggagttggtc ttacccgacg gcgctgcgcc     1380
aaccgcaagg gggcaggcga ccacggtagg gtcagcgact ggggtgaagt cgtaacaagg     1440
tagccgtagg ggaacctgcg gctggatcac ct                                   1472
```

<210> SEQ ID NO 4
<211> LENGTH: 1473
<212> TYPE: DNA
<213> ORGANISM: Methylobacterium sp.

<400> SEQUENCE: 4

```
ggtgatccag ccgcaggttc ccctacggct accttgttac gacttcaccc cagtcgctga       60
ccctaccgtg gtcgcctgcc tccttgcggt tggcgcagcg ccgtcgggta agaccaactc      120
ccatggtgtg acgggcggtg tgtacaaggc ccgggaacgt attcaccgtg gcgtgctgat      180
ccacgattac tagcgattcc gccttcatgc acccgagttg cagagtgcaa tccgaactga      240
gacggttttt ggggatttgc tccacctcgc ggcttcgcgt cccactgtca ccgccattgt      300
agcacgtgtg tagcccatcc cgtaagggcc atgaggactt gacgtcatcc acaccttcct      360
cgcggcttat caccggcagt ctccctagag tgcccaactg aatgatggca actaaggacg      420
tgggttgcgc tcgttgcggg acttaaccca acatctcacg acacgagctg acgacagcca      480
tgcagcacct gtgtgcacgc ctccgaagag gatccccgat ctctcgaggt aacatgccat      540
gtcaagggat ggtaaggttc tgcgcgttgc ttcgaattaa accacatgct ccaccgcttg      600
tgcgggcccc cgtcaattcc tttgagtttt aatcttgcga ccgtactccc caggcggaat      660
gcttaatgcg ttagcggcgc cactgacctg caagcaggcc aacggctggc attcatcgtt      720
tacggcgtgg actaccaggg tatctaatcc tgtttgctcc ccacgctttc gcgcctcagc      780
```

```
gtcagaaccg gaccagacag ccgccttcgc cactggtgtt cttgcgaata tctacgaatt        840
tcacctctac actcgcagtt ccgctgtcct cttccggtct caagccaacc agtatcgaag        900
gcaattctgt ggttgagcca caggctttca cccccgactt aatcggccgc ctacgcgccc        960
tttacgccca gtgattccga gcaacgctag ccccttcgt attaccgcgg ctgctggcac        1020
gaagttagcc ggggcttatt cttccggtac cgtcattatc gtcccggaca aaagagcttt       1080
acaaccctaa ggccttcatc actcacgcgg catggctgga tcaggcttgc gcccattgtc       1140
caatattccc cactgctgcc tcccgtagga gtctgggccg tgtctcagtc ccagtgtggc       1200
tgatcatcct ctcagaccag ctactgatcg tcgccttggt aggccgttac cccaccaaca       1260
agctaatcag acgcgggccg atccttcggc agtaaacctt tccccaaaag ggcgtatccg       1320
gtattagctc aagtttccct gagttattcc gaaccgaagg gtacgttccc acgtgttact       1380
cacccgtctg ccactgacac ccgaaggtgc ccgttcgact tgcatgtgtt aagcctgccg       1440
ccagcgttcg ctctgagcca ggatcaaact ctc                                    1473

<210> SEQ ID NO 5
<211> LENGTH: 1484
<212> TYPE: DNA
<213> ORGANISM: Methylobacterium sp.

<400> SEQUENCE: 5
ggtgatccag ccgcaggttc ccctacggct accttgttac gacttcaccc cagtcgctga         60
ccctaccgtg gtcgcctgcc tccagtcgag caagctcgat ttggttggcg cagcgccgtc        120
gggtaagacc aactcccatg gtgtgacggg cggtgtgtac aaggcccggg aacgtattca        180
ccgtggcatg ctgatccacg attactagcg attccgcctt catgcacgcg agttgcagcg        240
tgcaatccga actgagacgg cttttggaga ttggctccgg gtcacccctt cgcgtcccac        300
tgtcaccgcc attgtagcac gtgtgtagcc catcccgtaa gggccatgag gacttgacgt        360
catccacacc ttcctcgcgg cttatcaccg gcagtctccc tagagtgccc aaccaaatga        420
tggcaactaa ggacgtgggt tgcgctcgtt gcgggactta acccaacatc tcacgacacg        480
agctgacgac agccatgcag cacctgtgtg cgcgccccg aagggggacct ggaatctctc        540 ccagtaacac gccatgtcaa aggatggtaa ggttctgcgc gttgcttcga attaaaccac        600
atgctccacc gcttgtgcgg gcccccgtca attccttga gttttaatct tgcgaccgta        660
ctccccaggc ggaatgctta atgcgttagc tgcgctactg cggtgcatgc accccaacag       720
ctagcattca tcgtttacgg cgtggactac cagggtatct aatcctgttt gctccccacg       780 cttttcgcgcc tcagcgtcag taatggtcca gttggccgcc ttcgccaccg tgttcttgc       840 gaatatctac gaatttcacc tctacactcg cagttccacc aacctctacc atactcaagc       900
gtcccagtat cgaaggccat tctgtggttg agccacaggc tttcacccccc gacttaaaac       960 gccgcctacg cgcccttac gcccagtgat tccgagcaac gctagccccc ttcgtattac       1020
cgcggctgct ggcacgaagt tagccggggc ttattcctcc ggtaccgtca ttatcgtccc       1080
ggagaaaaga gctttacaac cctaaggccg tcatcactca cgcggcatgg ctggatcagg       1140
cttgcgccca ttgtccaata ttccccactg ctgcctcccg taggagtctg gccgtgtct       1200 cagtcccagt gtggctgatc atcctctcag accagctact gatcgtcgcc ttggtaggcc       1260
gttaccccac caacaagcta atcagacgcg ggccgatcct ccggcagtaa acctttctgc       1320
caaagcacgt atccggtatt agccctagtt tcccagggtt atcccagacc ggagggcacg       1380
ttcccacgtg ttactcaccc gtctgccact caccttgcgg tgcgttcgac ttgcatgtgt       1440
```

```
taagcctgcc gccagcgttc gctctgagcc aggatcaaac tctc            1484
```

<210> SEQ ID NO 6
<211> LENGTH: 1484
<212> TYPE: DNA
<213> ORGANISM: Methylobacterium sp.

<400> SEQUENCE: 6

```
gagtttgatc ctggctcaga gcgaacgctg gcggcaggct taacacatgc aagtcgaacg   60
caccgcaagg tgagtggcag acgggtgagt aacacgtggg aacgtgccct ccggtctggg  120
ataaccctgg gaaactaggg ctaataccgg atacgtgctt tggcagaaag gtttactgcc  180
ggaggatcgg cccgcgtctg attagcttgt tggtggggta acggcctacc aaggcgacga  240
tcagtagctg gtctgagagg atgatcagcc acactgggac tgagacacgg cccagactcc  300
tacgggaggc agcagtgggg aatattggac aatgggcgca agcctgatcc agccatgccg  360
cgtgagtgat gacggcctta gggttgtaaa gctcttttct ccgggacgat aatgacggta  420
ccggaggaat aagccccggc taacttcgtg ccagcagccg cggtaatacg aaggggcta  480
gcgttgctcg gaatcactgg gcgtaaaggg cgcgtaggcg cgttttaag tcggggtga  540
aagcctgtgg ctcaaccaca gaatggcctt cgatactggg acgcttgagt atggtagagg  600
ttggtggaac tgcgagtgta gaggtgaaat tcgtagatat tcgcaagaac accggtggcg  660
aaggcggcca actggaccat tactgacgct gaggcgcgaa agcgtgggga gcaaacagga  720
ttagataccc tggtagtcca cgccgtaaac gatgaatgct agctgttggg gtgcatgcac  780
cgcagtagcg cagctaacgc attaagcatt ccgcctgggg agtacggtcg caagattaaa  840
actcaaagga attgacgggg gcccgcacaa gcggtggagc atgtggttta attcgaagca  900
acgcgcagaa ccttaccatc ctttgacatg gcgtgttact gggagagatt ccaggtcccc  960
ttcgggggcg cgcacacagg tgctgcatgg ctgtcgtcag ctcgtgtcgt gagatgttgg 1020
gttaagtccc gcaacgagcg caacccacgt ccttagttgc catcatttgg ttgggcactc 1080
tagggagact gccggtgata agccgcgagg aaggtgtgga tgacgtcaag tcctcatggc 1140
ccttacggga tgggctacac acgtgctaca atggcggtga cagtgggacg cgaagggtg 1200
acccggagcc aatctccaaa agccgtctca gttcggattg cacgctgcaa ctcgcgtgca 1260
tgaaggcgga atcgctagta atcgtggatc agcatgccac ggtgaatacg ttcccgggcc 1320
ttgtacacac cgcccgtcac accatgggag ttggtcttac ccgacggcgc tgcgccaacc 1380
aaatcgagct tgctcgactg gaggcaggcg accacgtag gtcagcgac tggggtgaag 1440
tcgtaacaag gtagccgtag gggaacctgc ggctggatca cctc               1484
```

<210> SEQ ID NO 7
<211> LENGTH: 1472
<212> TYPE: DNA
<213> ORGANISM: Methylobacterium sp.

<400> SEQUENCE: 7

```
gagtttgatc ctggctcaga gcgaacgctg gcggcaggct taacacatgc aagtcgaacg   60
ggcttcttcg gaagtcagtg gcagacgggt gagtaacacg tgggaacgtg cccttcggtt  120
cggaataact cagggaaact tgagctaata ccggatacgc ccttacgggg aaaggtttac  180
tgccgaagga tcgcccgcg tctgattagc ttgttggtgg ggtaacggcc taccaaggcg  240
acgatcagta gctggtctga ggatgatc agccacactg gactgagac acggcccaga  300
```

```
ctcctacggg aggcagcagt ggggaatatt ggacaatggg cgcaagcctg atccagccat      360
gccgcgtgag tgatgaaggc cttagggttg taaagctctt ttgtccggga cgataatgac      420
ggtaccggaa gaataagccc cggctaactt cgtgccagca gccgcggtaa tacgaagggg      480
gctagcgttg ctcggaatca ctgggcgtaa agggcgcgta ggcggccgat taagtcgggg      540
gtgaaagcct gtggctcaac cacagaattg ccttcgatac tggttggctt gagaccggaa      600
gaggacagcg gaactgcgag tgtagaggtg aaattcgtag atattcgcaa gaacaccagt      660
ggcgaaggcg ctgtctggt ccggttctga cgctgaggcg cgaaagcgtg gggagcaaac       720
aggattagat accctggtag tccacgccgt aaacgatgaa tgccagccgt tggtctgctt      780
gcaggtcagt ggcgccgcta acgcattaag cattccgcct ggggagtacg gtcgcaagat      840
taaaactcaa aggaattgac gggggcccgc acaagcggtg gagcatgtgg tttaattcga      900
agcaacgcgc agaaccttac catcccttga catggcatgt acctcgaga gatcgggat       960
cctcttcgga ggcgtgcaca caggtgctgc atggctgtcg tcagctcgtg tcgtgagatg     1020
ttgggttaag tcccgcaacg agcgcaaccc acgtccttag ttgccatcat tcagttgggc     1080
actctaggga gactgccggt gataagccgc gaggaaggtg tggatgacgt caagtcctca     1140
tggcccttac gggatgggct acacacgtgc tacaatggcg gtgacagtgg gacgcgaaac     1200
cgcgaggttg agcaaatccc caaaagccgt ctcagttcgg attgcactct gcaactcggg     1260
tgcatgaagg cggaatcgct agtaatcgtg gatcagcacg ccacggtgaa tacgttcccg     1320
ggccttgtac acaccgcccg tcacaccatg ggagttggtc ttacccgacg gcgctgcgcc     1380
aaccgcaagg gggcaggcga ccacggtagg gtcagcgact ggggtgaagt cgtaacaagg     1440
tagccgtagg ggaacctgcg gctggatcac ct                                   1472
```

<210> SEQ ID NO 8
<211> LENGTH: 1473
<212> TYPE: DNA
<213> ORGANISM: Methylobacterium sp.

<400> SEQUENCE: 8

```
ggtgatccag ccgcaggttc ccctacggct accttgttac gacttcaccc cagtcgctga      60
ccctaccgtg gtcgcctgct ccccttgcgg gtcggcgcag cgccgtcggg taagaccaac     120
tcccatggtg tgacgggcgg tgtgtacaag gcccgggaac gtattcaccg tggcatgctg     180
atccacgatt actagcgatt ccgccttcat gcactcgagt tgcagagtgc aatccgaact     240
gagacggctt ttggagattt gcttgccctc gcgggttcgc gtcccactgt caccgccatt     300
gtagcacgtg tgtagcccat cccgtaaggg ccatgaggac ttgacgtcat ccacaccttc     360
ctcgcggctt atcaccggca gtctccccag agtgcccaac tgaatgatgg caactgagga     420
cgtgggttgc gctcgttgcg ggacttaacc caacatctca cgacacgagc tgacgacagc     480
catgcagcac ctgtgtgcgc gctcccgaag gagaccgtgg atctctccac gtaacacgcc     540
atgtcaaagg atggtaaggt tctgcgcgtt gcttcgaatt aaaccacatg ctccaccgct     600
tgtgcgggcc ccgtcaatt cctttgagtt ttaatcttgc gaccgtactc cccaggcgga      660
atgctcaaag cgttagctgc gccactgaga ggcaagcccc caacggctg gcattcatcg      720
tttacggcgt ggactaccag ggtatctaat cctgtttgct ccccacgctt tcgcgcctca     780
gcgtcagtgt cggaccagtt ggccgccttc gccaccggtg ttcttgcgaa tatctacgaa     840
tttcacctct acactcgcag ttccaccaac ctcttccgaa ctcaagtctc ccagtatcga     900
aggcaattct gtggttgagc cacaggcttt cacccccgac ttaaaagacc gcctacgcgc     960
```

```
cctttacgcc cagtgattcc gagcaacgct agccccttc gtattaccgc ggctgctggc    1020
acgaagttag ccggggctta ttcctccggt accgtcatta tcgtcccgga taaaagagct   1080
ttacaaccct aaggccttca tcactcacgc ggcatggctg gatcaggctt gcgcccattg   1140
tccaatattc cccactgctg cctcccgtag gagtctgggc cgtgtctcag tcccagtgtg   1200
gctgatcatc ctctcagacc agctactgat cgtcgccttg gtaggccgtt accccaccaa   1260
ctagctaatc agacgcgggc cgatcttccg gcagtaaacc tttccccaaa agggcgtatc   1320
cggtattagc tcaagtttcc ctgagttatt ccgaaccaga aggcacgttc ccacgcgtta   1380
ctcacccgtc cgccgctgac accgaagtgc ccgctcgact tgcatgtgtt aagcctgccg   1440
ccagcgttcg ctctgagcca ggatcaaact ctc                                1473

<210> SEQ ID NO 9
<211> LENGTH: 300
<212> TYPE: DNA
<213> ORGANISM: Methylobacterium sp.

<400> SEQUENCE: 9
acggtcaccc cacggactgg gcgagtacct caccggtgtt ctatcataac gccgagttag    60
ttttcgaccg tcccttatgc gatgtaccac cggtgtcggc agccgatttc gtcccaccgg   120
gagctggcgt tccggttcag accaccatca tcggtcacga tgtctggatt ggacacgggg   180
ccttcatctc ccccggcgtg actataggaa acggcgcgat cgtcggggcc caggcggtcg   240
tcacaagaga tgtcccaccc tatgcggtag ttgctggcgt ccccgcgacc gtacgacgat   300

<210> SEQ ID NO 10
<211> LENGTH: 300
<212> TYPE: DNA
<213> ORGANISM: Methylobacterium sp.

<400> SEQUENCE: 10
ccaataaaag cgttggccgc ctgggcaacc cgatccgagc ctaagactca aagcgcaagc    60
gaacacttgg tagagacagc ccgccgacta cggcgttcca gcactctccg gctttgatcg   120
gataggcatt ggtcaaggtg ccggtggtga tgacctcgcc cgccgcaagc ggcgaattac   180
tcggatcagc ggccagcacc tcgaccaagt gtcggagcgc gaccaaaggg ccacgttcga   240
ggacgtttga ggcgcgacca gtctcgatag tctcatcgtc gcggcgaagc tgcacctcga   300

<210> SEQ ID NO 11
<211> LENGTH: 300
<212> TYPE: DNA
<213> ORGANISM: Methylobacterium sp.

<400> SEQUENCE: 11
cgatggcacc gacctgccat gcctctgccg tccgcgccag aatggtaaag aggacgaagg    60
gggtaaggat cgtcgctgca gtgttgagca gcgaccagag aagggggccg aacatcggca   120
tcaaacctcg attgccactc ggacgcgaag cgcgtcttga aggagggatg gaagcgaaac   180
ggccgcagag taaccgccga cgaaagattg caccccctcat cgagcaggat cggaggtgaa   240
ggcaagcgtg ggttattggt aagtgcaaaa aatataatgg tagcgtcaga tctagcgttc   300

<210> SEQ ID NO 12
<211> LENGTH: 23
<212> TYPE: DNA
<213> ORGANISM: Artificial Sequence
<220> FEATURE:
```

<223> OTHER INFORMATION: primer

<400> SEQUENCE: 12
cctcaccggt gttctatcat aac                                      23

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccgatgatgg tggtctgaac                                          20

<210> SEQ ID NO 14
<211> LENGTH: 21
<212> TYPE: DNA
<213> ORGANISM: Artificial Sequence
<220> FEATURE:
<223> OTHER INFORMATION: Probe

<400> SEQUENCE: 14
cgtcccttat gcgatgtacc a                                        21

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gatccgagcc taagactcaa ag                                       22

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gaccaatgcc tatccgatca a                                        21

<210> SEQ ID NO 17
<211> LENGTH: 20
<212> TYPE: DNA
<213> ORGANISM: Artificial Sequence
<220> FEATURE:
<223> OTHER INFORMATION: Probe

<400> SEQUENCE: 17
aacacttggt agagacagcc                                          20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
aaggagggat ggaagcgaaa c                                        21

```
<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
ataacccacg cttgccttc                                                    19

<210> SEQ ID NO 20
<211> LENGTH: 21
<212> TYPE: DNA
<213> ORGANISM: Artificial Sequence
<220> FEATURE:
<223> OTHER INFORMATION: Probe

<400> SEQUENCE: 20
cgcagagtaa ccgccgacga a                                                 21

<210> SEQ ID NO 21
<211> LENGTH: 300
<212> TYPE: DNA
<213> ORGANISM: Methylobacterium sp.

<400> SEQUENCE: 21
gcccttctgt caggcgatat tgtataatgg cgttgcccca atagaagcag ccattcgtgc        60
gagggcagca gcgacgctag gtcgaaagag catcctaatc tcgatcaaga tgcgactgag       120
atttctgatg aaaatatcta gacacaagca aagctggtga aattcaacg atcatggcga        180 caattgcggc caattcggcc ggaacttgaa ggaacataaa aatgaatatt acaaatatac       240
cgcaaagcat gtagagttgc tacaccaagg gtcgggacgt ccaaaaaaac tcactgagga      300

<210> SEQ ID NO 22
<211> LENGTH: 300
<212> TYPE: DNA
<213> ORGANISM: Methylobacterium sp.

<400> SEQUENCE: 22
ggaacataaa aatgaatatt acaaatatac cgcaaagcat gtagagttgc tacaccaagg       60
gtcgggacgt ccaaaaaaac tcactgagga agtcgactgg aagcacgagg cgccccccc       120 aggagcgggg cgaccggcaa gggggcccgc aattgtcgcc atgatcgacc agcttaggta      180
ggatcctctt tcgacctaac gaatggctgc ttctattggg gcaacgccat tatacaatat      240
cgcctgacca tctggaacgc ggcccggtcc accggcaggt tggcgacgac agcgtcggag      300

<210> SEQ ID NO 23
<211> LENGTH: 300
<212> TYPE: DNA
<213> ORGANISM: Methylobacterium sp.

<400> SEQUENCE: 23
cggcgtcgac cagccgggcg aactgcttgg gcatgctctc ccgcgacgcc ggccacagcc       60
gcgtccccgt ccctccgcac aggatcatcg ggtggatttg aaaggcaaaa cgggacatca     120
ggataggccg ctcaggcgtt ggcgctgagg cgcttgatgt cggcgtcgac catctcggtg      180
atcagcgcct cgaggctggt ctcggcctcc cagccgaagg tcgccttggc cttggcgggg     240
ttgcccagca gcacctcgac ctctgccggc cggaacagcg ccgggtcgac gatcaggtgg     300

<210> SEQ ID NO 24
```

```
<211> LENGTH: 300
<212> TYPE: DNA
<213> ORGANISM: Methylobacterium sp.

<400> SEQUENCE: 24
ctggacatgc gcccaccccg gccaagtccg accgcaccgg caaccgctcc tgtagtcgtc      60
gtcatcgttc tcaccoctga ggcggagacc gtccgctaac ggggtgtctc aagcaaccgt     120
ggggcggagg aacacgcacg tagtcgcgtt tcaaggttcg cacgaacgcc tcggccatgc     180
cgttgctctg cgggctctcc agcggcgtcg tttttggcac caaaccaagg tcgcgggcga     240
agcggcgcgt gtcgcgggga ctgtcaggaa tttcgtgtgg gggcggccat agtggatccg     300

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
cacaagcaaa gctggtga                                                    18

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
aagatatgct ttgcgggta                                                   19

<210> SEQ ID NO 27
<211> LENGTH: 18
<212> TYPE: DNA
<213> ORGANISM: Artificial Sequence
<220> FEATURE:
<223> OTHER INFORMATION: Probe

<400> SEQUENCE: 27
cgatcatggc gacaattg                                                    18

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
caatatcgcc tgacagaagg                                                  20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cacttcaaca aaggcgatca                                                  20

<210> SEQ ID NO 30
<211> LENGTH: 14
```

```
<212> TYPE: DNA
<213> ORGANISM: Artificial Sequence
<220> FEATURE:
<223> OTHER INFORMATION: Probe

<400> SEQUENCE: 30
ttggcgacga cagc                                                        14

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
actgcttggg catgctctc                                                   19

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
cctatcctga tgtcccgttt                                                  20

<210> SEQ ID NO 33
<211> LENGTH: 20
<212> TYPE: DNA
<213> ORGANISM: Artificial Sequence
<220> FEATURE:
<223> OTHER INFORMATION: Probe

<400> SEQUENCE: 33
aggatcatcg ggtggatttg                                                  20

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
aggaacacgc acgtagtc                                                    18

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
ccacacgaaa ttcctgac                                                    18

<210> SEQ ID NO 36
<211> LENGTH: 14
<212> TYPE: DNA
<213> ORGANISM: Artificial Sequence
<220> FEATURE:
<223> OTHER INFORMATION: Probe

<400> SEQUENCE: 36
```

```
tggcaccaaa ccaa                                                14
```

<210> SEQ ID NO 37
<211> LENGTH: 300
<212> TYPE: DNA
<213> ORGANISM: Methylobacterium sp.

<400> SEQUENCE: 37

```
gcaaaacgac ctaatagttc tacagcggca tgcgccaagt cagcgcggtg aacagtatac    60
ctgggagcaa cttgtcctcc gaaacccaca taaaacaaat tactcctggc agtgcccagt   120
ccatcaaaat cgaatacaat atttctcgag gaggcatctg taatagcctg ccaaagcaac   180
aaagctatgg cgccgttatg actttcattg cttctggtag acataaaata atatgccgat   240
ttgtgatccc aaatgtagaa tattgccgca tcaattgcgc caagtttatt tcggatcgat   300
```

<210> SEQ ID NO 38
<211> LENGTH: 300
<212> TYPE: DNA
<213> ORGANISM: Methylobacterium sp.

<400> SEQUENCE: 38

```
ggcgccaacg gtatgatcgc atgattttcc tgcggcatag cttgcgggaa tggcgtattt    60
ggcgctctcc tcaggaattt ctaagggcat acgcaggaac tctacagcac ttttactggt   120
attttgtagt gacagcggag gaggctggtg ctcaaggtaa tcgtgatgaa gtgatccggg   180
ccattcgggg cgcgtttcta gtcttttcaa tccgcgccct gtaccacgta ttacgccgga   240
ccggtctgcg ccgcgccgcc ctcttgaccg ccctaaatgt ctaagagcgt ctaacaaagc   300
```

<210> SEQ ID NO 39
<211> LENGTH: 300
<212> TYPE: DNA
<213> ORGANISM: Methylobacterium sp.

<400> SEQUENCE: 39

```
gacgatatcg ctcatcttca ctgcattgaa gctggtgccg tactgcatag ggatgaaaaa    60
gtgatgcgga tagacggctg acgggaaagc gcctggtcga tcgaagactt tgctgacgag   120
gttgtggtag ccccggatat aggcatcgaa ggccgggacg ttgatcccat cctttgcctt   180
atcttgactg gcgtcgtcgc gtgccgtcag aacgggcacg tcgcaggtca tcgaggccag   240
caccttgcgg aacacctgcg ttccgccgtt gggattatcg acggcgaacg cggtggccgc   300
```

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40

```
gtcctccgaa acccacataa a                                        21
```

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41

```
ctaccagaag caatgaaagt cat                                      23
```

<210> SEQ ID NO 42
<211> LENGTH: 22
<212> TYPE: DNA
<213> ORGANISM: Artificial Sequence
<220> FEATURE:
<223> OTHER INFORMATION: Probe

<400> SEQUENCE: 42
tctgtaatag cctgccaaag ca                                            22

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
ggctggtgct caaggtaat                                                19

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
acatttaggg cggtcaagag                                               20

<210> SEQ ID NO 45
<211> LENGTH: 19
<212> TYPE: DNA
<213> ORGANISM: Artificial Sequence
<220> FEATURE:
<223> OTHER INFORMATION: Probe

<400> SEQUENCE: 45
atgaagtgat ccgggccat                                                19

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
ccgtactgca tagggatgaa a                                             21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
taaggcaaag gatgggatca a                                             21

<210> SEQ ID NO 48
<211> LENGTH: 21
<212> TYPE: DNA
<213> ORGANISM: Artificial Sequence
<220> FEATURE:

<223> OTHER INFORMATION: Probe

<400> SEQUENCE: 48
ttgctgacga ggttgtggta g                                      21

<210> SEQ ID NO 49
<211> LENGTH: 300
<212> TYPE: DNA
<213> ORGANISM: Methylobacterium sp.

<400> SEQUENCE: 49
ggaaatcggc ttcaagtacg acgtcacgcc ggccatgcag gtcacgggtg cactgttcaa   60
tctcgagcgc gacaaccagc cgttcccctc gaacgtggag tccggcctcg tccttggcgc  120
aggtcagaca cgcacccagg gcgcggaaat cggcctggcc ggctatctaa ccgattggtg  180
gcaggtcttt ggcggctacg cttataccga ggcacgcgta ctctcgccac tggaagacga  240
tggagacgtg atcgcagcag gtaatctcgt cggcaacgtt ccgctaaata ctttcagtct  300

<210> SEQ ID NO 50
<211> LENGTH: 300
<212> TYPE: DNA
<213> ORGANISM: Methylobacterium sp.

<400> SEQUENCE: 50
cggcctggcc ggctatctaa ccgattggtg gcaggtcttt ggcggctacg cttataccga   60
ggcacgcgta ctctcgccac tggaagacga tggagacgtg atcgcagcag gtaatctcgt  120
cggcaacgtt ccgctaaata ctttcagtct gttcaacaag ttcgatatca acgagaattt  180
ctccgttgct ctgggctatt actatcagga tgccagcttt gcctcctcag acaatgcagt  240
gcgtttgcca agttattcgc ggttcgatgg cgggttgttc tatcgattcg acgagttgac  300

<210> SEQ ID NO 51
<211> LENGTH: 300
<212> TYPE: DNA
<213> ORGANISM: Methylobacterium sp.

<400> SEQUENCE: 51
acgttccgct aaatactttc agtctgttca acaagttcga tatcaacgag aatttctccg   60
ttgctctggg ctattactat caggatgcca gctttgcctc ctcagacaat gcagtgcgtt  120
tgccaagtta ttcgcggttc gatggcgggt tgttctatcg attcgacgag ttgacacgcg  180
ttcagcttag cgtcgagaac attttcgaca ggcgttacat catcaactcc aacaacaaca  240
acaacctcac gcctggcgcg ccgagaacag tccgcgtgca attgatcgct cggttctaaa  300

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tttggcggct acgcttatac                                        20

<210> SEQ ID NO 53
<211> LENGTH: 20
<212> TYPE: DNA
<213> ORGANISM: Artificial Sequence
<220> FEATURE:
<223> OTHER INFORMATION: Primer

```
<400> SEQUENCE: 53
aacgttgccg acgagattac                                                    20

<210> SEQ ID NO 54
<211> LENGTH: 22
<212> TYPE: DNA
<213> ORGANISM: Artificial Sequence
<220> FEATURE:
<223> OTHER INFORMATION: Probe

<400> SEQUENCE: 54
agacgatgga gacgtgatcg ca                                                 22

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ggcaacgttc cgctaaatac                                                    20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
aaagctggca tcctgatagt                                                    20

<210> SEQ ID NO 57
<211> LENGTH: 22
<212> TYPE: DNA
<213> ORGANISM: Artificial Sequence
<220> FEATURE:
<223> OTHER INFORMATION: Probe

<400> SEQUENCE: 57
cgagaatttc tccgttgctc tg                                                 22

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
cgatggcggg ttgttctat                                                     19

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
aggcgtgagg ttgttgtt                                                      18

<210> SEQ ID NO 60
```

```
<211> LENGTH: 22
<212> TYPE: DNA
<213> ORGANISM: Artificial Sequence
<220> FEATURE:
<223> OTHER INFORMATION: Probe

<400> SEQUENCE: 60
aggcgttaca tcatcaactc ca                                              22
```